United States Patent
Sayger et al.

(10) Patent No.: US 12,059,183 B2
(45) Date of Patent: Aug. 13, 2024

(54) BONE PLATES WITH DYNAMIC ELEMENTS AND SCREWS

(71) Applicant: CROSSROADS EXTREMITY SYSTEMS, LLC, Memphis, TN (US)

(72) Inventors: Daniel Sayger, Southaven, MS (US); Vernon R. Hartdegen, Collierville, TN (US); Michael Chad Hollis, Collierville, TN (US)

(73) Assignee: Crossroads Extremity Systems, LLC, Memphis, TN (US)

( * ) Notice: Subject to any disclaimer, the term of this patent is extended or adjusted under 35 U.S.C. 154(b) by 135 days.

(21) Appl. No.: 17/391,135

(22) Filed: Aug. 2, 2021

(65) Prior Publication Data

US 2022/0031371 A1    Feb. 3, 2022

Related U.S. Application Data

(60) Provisional application No. 63/059,844, filed on Jul. 31, 2020.

(51) Int. Cl.
*A61B 17/80* (2006.01)
*A61B 17/84* (2006.01)
(Continued)

(52) U.S. Cl.
CPC ...... *A61B 17/8004* (2013.01); *A61B 17/8057* (2013.01); *A61B 17/842* (2013.01);
(Continued)

(58) Field of Classification Search
CPC ... A61B 17/808; A61B 17/809; A61B 17/842; A61B 17/846; A61B 17/848;
(Continued)

(56) References Cited

U.S. PATENT DOCUMENTS 2,010,913 A    8/1935    Bruce
2,133,859 A    10/1938    Hawley
(Continued)

FOREIGN PATENT DOCUMENTS

CA    2063484    9/1993
CN    2404495    9/1993
(Continued)

OTHER PUBLICATIONS

DePuy Synthes, BME Elite Implant Technique Overview, (Oct. 25, 2017), 2 pp.
(Continued)

*Primary Examiner* — Anu Ramana
(74) *Attorney, Agent, or Firm* — BakerHostetler

(57) ABSTRACT

A bone plate assembly may include a bone plate with an obverse side, a reverse side, a fastener hole formed through the bone plate from the obverse side to the reverse side, a first draw hole formed through the bone plate from the obverse side to the reverse side, with a wire engagement surface, a fastener insertable through the fastener hole and into tissue, and a first wire insertable into the first draw hole, with a distal end anchorable in the tissue and a proximal end with a retention portion that is retainable in the first draw hole. The wire engagement surface may be oriented obliquely relative to a pilot hole formed in the tissue to receive the wire such that motion of the first wire through the first draw hole exerts a compressive force against the tissue.

20 Claims, 20 Drawing Sheets

(51) Int. Cl.
*A61B 17/86* (2006.01)
*A61B 17/00* (2006.01)
*A61B 17/56* (2006.01)

(52) U.S. Cl.
CPC ... *A61B 17/8605* (2013.01); *A61B 2017/00526* (2013.01); *A61B 2017/564* (2013.01)

(58) Field of Classification Search
CPC .............. A61B 17/861; A61B 17/8014; A61B 17/8019; A61B 17/8052; A61B 17/8057; A61B 2017/564; A61B 2017/681; A61B 17/0642; A61B 17/0643; A61B 17/7044
See application file for complete search history.

(56) References Cited

U.S. PATENT DOCUMENTS

| | | |
|---|---|---|
| 2,544,492 A | 3/1951 | Downing |
| 2,811,073 A | 10/1957 | Klopstock |
| 3,741,205 A | 6/1973 | Markolf et al. |
| 4,263,903 A | 4/1981 | Griggs |
| 4,278,091 A | 7/1981 | Borzone |
| 4,415,111 A | 11/1983 | McHarrie et al. |
| 4,438,769 A | 3/1984 | Pratt et al. |
| 4,454,875 A | 6/1984 | Pratt et al. |
| 4,484,570 A | 11/1984 | Sutter et al. |
| 4,655,222 A | 4/1987 | Florez et al. |
| 4,723,540 A | 2/1988 | Gilmer, Jr. |
| 4,805,617 A | 2/1989 | Bedi et al. |
| 4,848,328 A | 7/1989 | Laboureau et al. |
| 4,852,558 A | 8/1989 | Outerbridge |
| 4,874,122 A | 10/1989 | Froelich et al. |
| 5,013,315 A | 5/1991 | Barrows |
| 5,044,540 A | 9/1991 | Dulebohn |
| 5,209,756 A | 5/1993 | Seedhom et al. |
| 5,246,443 A | 9/1993 | Mai |
| 5,258,012 A | 11/1993 | Luscombe et al. |
| 5,352,229 A | 10/1994 | Goble et al. |
| 5,395,372 A | 3/1995 | Holt et al. |
| 5,425,489 A | 6/1995 | Shichman et al. |
| 5,449,359 A | 9/1995 | Groiso |
| 5,454,814 A | 10/1995 | Comte |
| 5,456,400 A | 10/1995 | Shichman et al. |
| 5,490,409 A | 2/1996 | Weber |
| 5,498,749 A | 3/1996 | Heise et al. |
| 5,520,700 A | 5/1996 | Beyar et al. |
| 5,578,034 A | 11/1996 | Estes |
| 5,607,425 A | 3/1997 | Rogozinski |
| 5,628,740 A | 5/1997 | Mullane |
| 5,634,926 A | 6/1997 | Jobe |
| 5,660,188 A | 8/1997 | Groiso |
| 5,662,655 A | 9/1997 | Laboureau et al. |
| 5,716,357 A | 2/1998 | Rogozinski |
| 5,749,564 A | 5/1998 | Malek |
| 5,779,707 A | 7/1998 | Bertholet et al. |
| 5,785,713 A | 7/1998 | Jobe |
| 5,788,698 A | 8/1998 | Savornin |
| 5,807,403 A | 9/1998 | Beyar et al. |
| 5,853,414 A | 12/1998 | Groiso |
| 5,904,682 A | 5/1999 | Rogozinski |
| 5,931,839 A | 8/1999 | Medoff |
| 5,947,968 A | 9/1999 | Rogozinski |
| 5,947,999 A | 9/1999 | Groiso |
| 5,972,000 A | 10/1999 | Beyar et al. |
| 5,993,476 A | 11/1999 | Groiso |
| 6,010,504 A | 1/2000 | Rogozinski |
| 6,017,343 A | 1/2000 | Rogozinski |
| 6,019,759 A | 2/2000 | Rogozinski |
| 6,059,787 A | 5/2000 | Allen |
| 6,089,435 A | 7/2000 | Malek |
| 6,105,936 A | 8/2000 | Malek |
| 6,120,503 A | 9/2000 | Michelson |
| 6,179,840 B1 | 1/2001 | Bowman |
| 6,187,009 B1 | 2/2001 | Herzog et al. |
| 6,281,262 B1 | 8/2001 | Shikinami |
| 6,322,562 B1 | 11/2001 | Wolter |
| 6,334,446 B1 | 1/2002 | Beyar |
| 6,336,927 B2 | 1/2002 | Rogozinski |
| 6,348,054 B1 | 2/2002 | Allen |
| 6,364,884 B1 | 4/2002 | Bowman et al. |
| 6,379,354 B1 | 4/2002 | Rogozinski |
| 6,387,041 B1 | 5/2002 | Harari et al. |
| 6,402,765 B1 | 6/2002 | Monassevitch et al. |
| 6,402,766 B2 | 6/2002 | Bowman et al. |
| 6,406,480 B1 | 6/2002 | Beyar et al. |
| 6,423,073 B2 | 7/2002 | Bowman |
| 6,436,110 B2 | 8/2002 | Bowman et al. |
| 6,447,517 B1 | 9/2002 | Bowman |
| 6,497,707 B1 | 12/2002 | Bowman et al. |
| 6,544,273 B1 | 4/2003 | Harari et al. |
| 6,575,984 B2 | 6/2003 | Beyar |
| 6,575,998 B2 | 6/2003 | Beyar |
| 6,582,435 B2 | 6/2003 | Wellisz et al. |
| 6,592,610 B2 | 7/2003 | Beyar |
| 6,635,058 B2 | 10/2003 | Beyar et al. |
| 6,652,531 B2 | 11/2003 | Wellisz et al. |
| 6,663,642 B2 | 12/2003 | Beyar et al. |
| 6,679,885 B2 | 1/2004 | Wellisz |
| 6,709,437 B2 | 3/2004 | Wellisz |
| 6,730,110 B1 | 5/2004 | Harari et al. |
| 6,746,455 B2 | 6/2004 | Beyar et al. |
| 6,783,531 B2 | 8/2004 | Allen |
| 6,896,684 B2 | 5/2005 | Monassevitch et al. |
| 6,966,911 B2 | 11/2005 | Groiso |
| 6,974,461 B1 | 12/2005 | Wolter |
| 7,044,951 B2 | 5/2006 | Medoff et al. |
| 7,090,676 B2 | 8/2006 | Huebner et al. |
| 7,147,640 B2 | 12/2006 | Huebner et al. |
| 7,153,309 B2 | 12/2006 | Huebner et al. |
| 7,179,260 B2 | 2/2007 | Gerlach et al. |
| 7,189,237 B2 | 3/2007 | Huebner |
| 7,214,232 B2 | 5/2007 | Bowman et al. |
| 7,226,408 B2 | 6/2007 | Harai et al. |
| 7,229,452 B2 | 6/2007 | Kayan |
| 7,235,079 B2 | 6/2007 | Jensen et al. |
| 7,250,054 B2 | 7/2007 | Allen et al. |
| 7,255,701 B2 | 8/2007 | Allen et al. |
| 7,311,712 B2 | 12/2007 | Dalton |
| 7,326,212 B2 | 2/2008 | Huebner |
| D574,956 S | 8/2008 | Grim |
| 7,438,209 B1 | 10/2008 | Hess et al. |
| 7,473,255 B2 | 1/2009 | McGarity et al. |
| 7,473,257 B2 | 1/2009 | Knopfle et al. |
| D586,915 S | 2/2009 | Grim |
| 7,500,979 B2 | 3/2009 | Hueil et al. |
| 7,506,791 B2 | 3/2009 | Omaits et al. |
| 7,537,596 B2 | 5/2009 | Jensen |
| 7,537,603 B2 | 5/2009 | Huebner et al. |
| 7,537,604 B2 | 5/2009 | Huebner |
| 7,556,647 B2 | 7/2009 | Drews et al. |
| 7,562,105 B2 | 7/2009 | Liu et al. |
| 7,578,825 B2 | 8/2009 | Huebner |
| 7,604,151 B2 | 10/2009 | Hess et al. |
| 7,618,441 B2 | 11/2009 | Groiso |
| 7,651,498 B2 | 1/2010 | Shifrin et al. |
| 7,665,647 B2 | 2/2010 | Shelton, IV et al. |
| 7,669,746 B2 | 3/2010 | Shelton, IV |
| 7,669,747 B2 | 3/2010 | Weisenburgh, II et al. |
| 7,673,781 B2 | 3/2010 | Swayze et al. |
| 7,673,782 B2 | 3/2010 | Hess et al. |
| 7,704,251 B2 | 4/2010 | Huebner et al. |
| 7,704,279 B2 | 4/2010 | Moskowitz et al. |
| 7,717,945 B2 | 5/2010 | Jensen et al. |
| 7,735,703 B2 | 6/2010 | Morgan et al. |
| 7,740,634 B2 | 6/2010 | Orbay et al. |
| 7,766,209 B2 | 8/2010 | Baxter, III et al. |
| 7,766,948 B1 | 8/2010 | Leung |
| 7,771,433 B2 | 8/2010 | Orbay et al. |
| 7,794,475 B2 | 9/2010 | Hess et al. |
| 7,832,612 B2 | 11/2010 | Baxter, III et al. |
| 7,846,188 B2 | 12/2010 | Moskowitz et al. |
| 7,857,186 B2 | 12/2010 | Baxter, III et al. |
| 7,857,836 B2 | 12/2010 | Huebner et al. |
| 7,867,265 B2 | 1/2011 | Beutter |

(56) References Cited

U.S. PATENT DOCUMENTS

| | | | |
|---|---|---|---|
| 7,905,381 B2 | 3/2011 | Baxter, III et al. |
| 7,905,910 B2 | 3/2011 | Gerlach et al. |
| 7,909,858 B2 | 3/2011 | Gerlach et al. |
| 7,914,532 B2 | 3/2011 | Shaver et al. |
| 7,918,879 B2 | 4/2011 | Yeung et al. |
| 7,927,332 B2 | 4/2011 | Huebner et al. |
| 7,934,630 B2 | 5/2011 | Shelton, IV et al. |
| 7,935,126 B2 | 5/2011 | Orbay et al. |
| 7,942,903 B2 | 5/2011 | Moskowitz et al. |
| 7,951,180 B2 | 5/2011 | Moskowitz et al. |
| 7,954,686 B2 | 6/2011 | Baxter, III et al. |
| 7,955,388 B2 | 6/2011 | Jensen et al. |
| 7,963,982 B2 | 6/2011 | Kirschman |
| 7,966,799 B2 | 6/2011 | Morgan et al. |
| 7,972,363 B2 | 7/2011 | Moskowitz et al. |
| 8,016,867 B2 | 9/2011 | Bowman |
| 8,043,346 B2 | 10/2011 | Markworth |
| 8,100,953 B2 | 1/2012 | White et al. |
| 8,105,367 B2 | 1/2012 | Austin et al. |
| 8,114,139 B2 | 2/2012 | Sournac et al. |
| 8,137,351 B2 | 3/2012 | Prandi |
| 8,141,762 B2 | 3/2012 | Bedi et al. |
| 8,172,886 B2 | 5/2012 | Castaneda et al. |
| 8,177,819 B2 | 5/2012 | Huebner et al. |
| 8,182,518 B2 | 5/2012 | Butler et al. |
| 8,186,560 B2 | 5/2012 | Hess et al. |
| 8,205,781 B2 | 6/2012 | Baxter, III et al. |
| 8,220,690 B2 | 7/2012 | Hess et al. |
| 8,231,627 B2 | 7/2012 | Huebner et al. |
| 8,231,662 B2 | 7/2012 | Huebner |
| 8,241,326 B2 | 8/2012 | Harari et al. |
| 8,241,338 B2 | 8/2012 | Castaneda et al. |
| 8,252,032 B2 | 8/2012 | White et al. |
| 8,257,370 B2 | 9/2012 | Moskowitz et al. |
| 8,262,711 B2 | 9/2012 | Hess |
| 8,287,543 B2 | 10/2012 | Medoff |
| 8,317,070 B2 | 11/2012 | Hueil et al. |
| 8,337,537 B2 | 12/2012 | Pelo et al. |
| 8,348,129 B2 | 1/2013 | Bedi et al. |
| 8,348,131 B2 | 1/2013 | Omaits et al. |
| 8,353,913 B2 | 1/2013 | Moskowitz et al. |
| 8,360,297 B2 | 1/2013 | Shelton, IV et al. |
| 8,365,976 B2 | 2/2013 | Hess et al. |
| 8,382,807 B2 | 2/2013 | Austin et al. |
| 8,393,517 B2 | 3/2013 | Milo |
| 8,398,717 B2 | 3/2013 | Kleinman |
| 8,413,872 B2 | 4/2013 | Patel |
| 8,425,574 B2 | 4/2013 | Huebner et al. |
| 8,425,575 B2 | 4/2013 | Huebner et al. |
| 8,425,576 B2 | 4/2013 | Anderson et al. |
| 8,430,292 B2 | 4/2013 | Patel et al. |
| 8,449,561 B2 | 5/2013 | Bowman |
| 8,453,908 B2 | 6/2013 | Bedi et al. |
| 8,464,923 B2 | 6/2013 | Shelton, IV |
| 8,475,504 B2 | 7/2013 | Gillard et al. |
| 8,485,412 B2 | 7/2013 | Shelton, IV et al. |
| 8,486,116 B2 | 7/2013 | Heilman |
| 8,496,693 B2 | 7/2013 | Robinson |
| 8,499,993 B2 | 8/2013 | Shelton, IV et al. |
| 8,518,090 B2 | 8/2013 | Huebner et al. |
| 8,523,919 B2 | 9/2013 | Huebner et al. |
| 8,540,129 B2 | 9/2013 | Baxter, III et al. |
| 8,540,133 B2 | 9/2013 | Bedi et al. |
| D691,720 S | 10/2013 | Cheney et al. |
| 8,545,540 B2 | 10/2013 | Castaneda et al. |
| 8,561,870 B2 | 10/2013 | Baxter, III et al. |
| 8,567,656 B2 | 10/2013 | Shelton, IV et al. |
| 8,574,270 B2 | 11/2013 | Hess et al. |
| 8,584,853 B2 | 11/2013 | Knight et al. |
| 8,585,743 B2 | 11/2013 | Ampuero et al. |
| 8,590,762 B2 | 11/2013 | Hess et al. |
| 8,596,514 B2 | 12/2013 | Miller et al. |
| 8,603,161 B2 | 12/2013 | Drews et al. |
| 8,636,187 B2 | 1/2014 | Hueil et al. |
| 8,652,142 B2 | 2/2014 | Geissler |
| 8,652,180 B2 | 2/2014 | Federspiel et al. |
| 8,657,820 B2 | 2/2014 | Kubiak et al. |
| 8,668,130 B2 | 3/2014 | Hess et al. |
| 8,672,208 B2 | 3/2014 | Hess et al. |
| 8,672,828 B2 | 3/2014 | Harari et al. |
| 8,679,123 B2 | 3/2014 | Kinmon et al. |
| D705,930 S | 5/2014 | Cheney |
| 8,720,766 B2 | 5/2014 | Hess et al. |
| 8,727,197 B2 | 5/2014 | Hess et al. |
| 8,728,128 B2 | 5/2014 | Hawkes |
| 8,728,129 B2 | 5/2014 | Fritzinger et al. |
| 8,734,516 B2 | 5/2014 | Moskowitz et al. |
| 8,740,915 B2 | 6/2014 | Niederberger et al. |
| 8,747,444 B2 | 6/2014 | Moskowitz et al. |
| 8,763,875 B2 | 7/2014 | Morgan et al. |
| 8,777,969 B2 | 7/2014 | Kayan |
| 8,779,927 B2 | 7/2014 | Bell et al. |
| 8,784,450 B2 | 7/2014 | Moskowitz et al. |
| 8,800,838 B2 | 8/2014 | Shelton, IV |
| 8,808,325 B2 | 8/2014 | Hess et al. |
| 8,808,335 B2 | 8/2014 | Biedermann |
| 8,814,915 B2 | 8/2014 | Hess et al. |
| 8,834,537 B2 | 9/2014 | Castaneda et al. |
| 8,858,562 B2 | 10/2014 | Orbay et al. |
| 8,870,882 B2 | 10/2014 | Kleiner |
| 8,882,812 B2 | 11/2014 | Hess et al. |
| 8,888,824 B2 | 11/2014 | Austin et al. |
| 8,888,826 B2 | 11/2014 | Kinmon et al. |
| 8,894,651 B2 | 11/2014 | Aflatoon |
| 8,899,465 B2 | 12/2014 | Shelton, IV et al. |
| 8,906,046 B2 | 12/2014 | Anderson |
| 8,925,788 B2 | 1/2015 | Hess et al. |
| 8,936,615 B2 * | 1/2015 | Pappalardo ......... A61B 17/863 |
| | | 606/105 |
| 8,940,028 B2 | 1/2015 | Austin et al. |
| 8,973,804 B2 | 3/2015 | Hess et al. |
| 8,974,504 B2 | 3/2015 | Hess et al. |
| 8,986,305 B2 | 3/2015 | Aflatoon et al. |
| 8,991,676 B2 | 3/2015 | Hess et al. |
| 8,992,581 B2 | 3/2015 | Austin et al. |
| 9,005,206 B2 | 4/2015 | Ampuero et al. |
| 9,005,293 B2 | 4/2015 | Moskowitz et al. |
| 9,017,331 B2 | 4/2015 | Fox |
| 9,017,380 B2 | 4/2015 | Mayer et al. |
| 9,034,037 B2 | 5/2015 | Fiere et al. |
| 9,072,554 B2 | 7/2015 | Reynolds et al. |
| 9,078,757 B2 | 7/2015 | Kleinman et al. |
| 9,095,338 B2 | 8/2015 | Taylor et al. |
| 9,095,388 B2 | 8/2015 | Hess et al. |
| 9,101,349 B2 | 8/2015 | Knight et al. |
| 9,107,661 B2 | 8/2015 | Euteneuer et al. |
| 9,125,650 B2 | 9/2015 | Euteneuer et al. |
| 9,138,233 B2 | 9/2015 | Anderson |
| 9,179,911 B2 | 11/2015 | Morgan et al. |
| 9,180,022 B2 | 11/2015 | Georges et al. |
| 9,204,932 B2 | 12/2015 | Knight et al. |
| 9,220,515 B2 | 12/2015 | Castaneda et al. |
| 9,237,891 B2 | 1/2016 | Shelton, IV |
| 9,247,978 B2 | 2/2016 | Euteneuer et al. |
| 9,265,649 B2 | 2/2016 | Pflueger et al. |
| D752,219 S | 3/2016 | Peterson et al. |
| 9,271,726 B2 | 3/2016 | Euteneuer |
| 9,283,006 B2 | 3/2016 | Fonte |
| 9,289,206 B2 | 3/2016 | Hess et al. |
| 9,289,210 B2 | 3/2016 | Baxter, III et al. |
| 9,301,854 B2 | 4/2016 | Moskowitz et al. |
| 9,307,988 B2 | 4/2016 | Shelton, IV |
| 9,308,033 B2 | 4/2016 | Huebner et al. |
| 9,326,768 B2 | 5/2016 | Shelton, IV |
| 9,326,771 B2 | 5/2016 | Baxter, III et al. |
| 9,339,268 B2 | 5/2016 | Fox |
| 9,370,355 B2 | 6/2016 | Anderson |
| 9,370,356 B2 | 6/2016 | Euteneuer et al. |
| 9,370,376 B2 | 6/2016 | Castaneda et al. |
| 9,387,020 B2 * | 7/2016 | Geissler ............ A61B 17/8061 |
| 9,387,116 B2 | 7/2016 | Pflueger et al. |
| 9,402,623 B2 | 8/2016 | Kayan |
| 9,402,624 B1 | 8/2016 | Scott et al. |
| 9,408,603 B2 | 8/2016 | Patel |

(56) References Cited

U.S. PATENT DOCUMENTS

| | | | |
|---|---|---|---|
| 9,408,604 B2 | 8/2016 | Shelton, IV et al. |
| 9,408,647 B2 | 8/2016 | Cheney |
| 9,414,841 B2 | 8/2016 | Euteneuer et al. |
| 9,414,871 B2 | 8/2016 | Huebner et al. |
| 9,421,013 B2 | 8/2016 | Patel et al. |
| 9,445,808 B2 | 9/2016 | Woodard, Jr. et al. |
| 9,451,957 B2 | 9/2016 | Fox |
| 9,463,015 B2 | 10/2016 | Hausen |
| 9,486,212 B2 | 11/2016 | Miller et al. |
| D773,665 S | 12/2016 | Cheney et al. |
| D773,666 S | 12/2016 | Cheney et al. |
| 9,532,821 B2 | 1/2017 | Moskowitz et al. |
| 9,539,023 B2 | 1/2017 | Marotte |
| 9,549,735 B2 | 1/2017 | Shelton, IV et al. |
| D780,311 S | 2/2017 | Cheney et al. |
| 9,561,032 B2 | 2/2017 | Shelton, IV et al. |
| 9,566,063 B2 | 2/2017 | Euteneuer et al. |
| 9,603,641 B2 | 3/2017 | Hulliger |
| 9,615,856 B2 | 4/2017 | Arnett et al. |
| 9,763,715 B2 | 9/2017 | Mather et al. |
| 9,839,458 B2 | 12/2017 | Bouduban et al. |
| 9,861,404 B2 | 1/2018 | Reiley |
| 9,918,762 B2 | 3/2018 | Federspiel et al. |
| 9,924,984 B2 | 3/2018 | Hartdegen et al. |
| 9,955,964 B2 | 5/2018 | Mayer et al. |
| 10,052,103 B2 | 8/2018 | Wahl |
| 10,117,647 B2 | 11/2018 | Cheney |
| 10,166,022 B2 | 1/2019 | Early et al. |
| 10,186,402 B2 | 1/2019 | Kamata et al. |
| 10,292,743 B2 | 5/2019 | Taylor et al. |
| 10,299,842 B2 | 5/2019 | Hollis et al. |
| 10,307,156 B1 | 6/2019 | Blair et al. |
| 10,357,986 B2 | 7/2019 | Zhou et al. |
| 10,433,885 B2 | 10/2019 | Hartdegen et al. |
| 10,448,979 B2 | 10/2019 | Fox |
| D870,284 S | 12/2019 | Hollis et al. |
| 10,492,841 B2 | 12/2019 | Hartdegen et al. |
| D892,331 S | 8/2020 | Hollis et al. |
| D895,113 S | 9/2020 | Blair et al. |
| 10,779,944 B2 | 9/2020 | Cousins et al. |
| 11,179,149 B2 | 11/2021 | Hartdegen et al. |
| 11,432,856 B2 * | 9/2022 | Biedermann ...... A61B 17/8042 |
| 11,547,458 B2 * | 1/2023 | Biedermann ...... A61B 17/8042 |
| 2001/0028148 A1 | 10/2001 | White |
| 2002/0095155 A1 | 7/2002 | Michelson |
| 2002/0095181 A1 | 7/2002 | Beyar |
| 2002/0111641 A1 | 8/2002 | Peterson et al. |
| 2003/0083663 A1 | 5/2003 | Goldhahn et al. |
| 2003/0158553 A1 | 8/2003 | Michelson |
| 2003/0225409 A1 | 12/2003 | Freid et al. |
| 2004/0073222 A1 | 4/2004 | Koseki |
| 2004/0127896 A1 | 7/2004 | Lombardo et al. |
| 2004/0172040 A1 | 9/2004 | Heggeness |
| 2004/0220570 A1 | 11/2004 | Frigg |
| 2005/0021032 A1 | 1/2005 | Koo |
| 2005/0021035 A1 | 1/2005 | Groiso |
| 2005/0043757 A1 | 2/2005 | Arad et al. |
| 2005/0049594 A1 * | 3/2005 | Wack ............... A61B 17/1728 |
| | | | 606/281 |
| 2005/0049600 A1 | 3/2005 | Groiso |
| 2005/0085818 A1 | 4/2005 | Huebner |
| 2005/0096660 A1 | 5/2005 | Allen |
| 2005/0101961 A1 | 5/2005 | Huebner et al. |
| 2005/0107796 A1 | 5/2005 | Gerlach et al. |
| 2005/0119667 A1 | 6/2005 | Leport et al. |
| 2005/0165400 A1 | 7/2005 | Fernandez |
| 2005/0171544 A1 | 8/2005 | Falkner |
| 2005/0234458 A1 | 10/2005 | Huebner |
| 2005/0240187 A1 | 10/2005 | Huebner et al. |
| 2006/0058796 A1 | 3/2006 | Hartdegen et al. |
| 2006/0058802 A1 | 3/2006 | Kofoed |
| 2006/0106391 A1 | 5/2006 | Huebner |
| 2006/0122604 A1 | 6/2006 | Gorhan et al. |
| 2006/0122605 A1 | 6/2006 | Suh et al. |
| 2006/0129151 A1 | 6/2006 | Allen et al. |
| 2006/0200147 A1 | 9/2006 | Ensign et al. |
| 2006/0241612 A1 | 10/2006 | Medoff |
| 2006/0241618 A1 | 10/2006 | Gasser et al. |
| 2006/0264936 A1 | 11/2006 | Partin et al. |
| 2007/0055249 A1 | 3/2007 | Jensen et al. |
| 2007/0173840 A1 | 7/2007 | Huebner |
| 2007/0191850 A1 | 8/2007 | Kim et al. |
| 2007/0208358 A1 | 9/2007 | Kayan |
| 2007/0233116 A1 | 10/2007 | Olerud |
| 2008/0147125 A1 | 6/2008 | Colleran et al. |
| 2008/0195099 A1 | 8/2008 | Minas |
| 2008/0200955 A1 | 8/2008 | Tepic |
| 2008/0255620 A1 | 10/2008 | Strauss et al. |
| 2008/0275510 A1 | 11/2008 | Schonhardt et al. |
| 2008/0288000 A1 | 11/2008 | Cawley |
| 2008/0319443 A1 | 12/2008 | Focht et al. |
| 2009/0054930 A1 | 2/2009 | Aflatoon |
| 2009/0138082 A1 | 5/2009 | Reah et al. |
| 2009/0177203 A1 | 7/2009 | Reiley |
| 2009/0182383 A1 | 7/2009 | Prybyla et al. |
| 2009/0187247 A1 | 7/2009 | Metcalf, Jr. et al. |
| 2009/0254090 A1 | 10/2009 | Lizee |
| 2009/0254126 A1 | 10/2009 | Orbay et al. |
| 2009/0281543 A1 | 11/2009 | Orbay et al. |
| 2010/0036430 A1 | 2/2010 | Hartdegen et al. |
| 2010/0076448 A1 | 3/2010 | Abdou |
| 2010/0082065 A1 | 4/2010 | Butler et al. |
| 2010/0100138 A1 | 4/2010 | Reynolds et al. |
| 2010/0106196 A1 | 4/2010 | Erikcson et al. |
| 2010/0133316 A1 | 6/2010 | Lizee et al. |
| 2010/0211116 A1 | 8/2010 | Suh et al. |
| 2010/0256765 A1 | 10/2010 | Butler et al. |
| 2010/0292715 A1 | 11/2010 | Nering et al. |
| 2010/0312280 A1 | 12/2010 | Overes et al. |
| 2011/0022049 A1 | 1/2011 | Huebner et al. |
| 2011/0022099 A1 | 1/2011 | Ashman |
| 2011/0029016 A1 | 2/2011 | Yeung et al. |
| 2011/0029023 A1 | 2/2011 | Tornier |
| 2011/0029025 A1 | 2/2011 | Medoff |
| 2011/0054542 A1 | 3/2011 | Kevin et al. |
| 2011/0092981 A1 | 4/2011 | Ng et al. |
| 2011/0098754 A1 | 4/2011 | Hulliger et al. |
| 2011/0118742 A1 | 5/2011 | Hulliger et al. |
| 2011/0118796 A1 | 5/2011 | Reiley et al. |
| 2011/0118840 A1 | 5/2011 | Huntsman et al. |
| 2011/0202092 A1 | 8/2011 | Frigg et al. |
| 2011/0270326 A1 | 11/2011 | Black et al. |
| 2011/0282393 A1 | 11/2011 | Gerlach et al. |
| 2011/0295324 A1 | 12/2011 | Donley et al. |
| 2011/0313421 A1 | 12/2011 | Sidebotham et al. |
| 2011/0319942 A1 | 12/2011 | Bottlang et al. |
| 2012/0022600 A1 | 1/2012 | Overes et al. |
| 2012/0024937 A1 | 2/2012 | Allen |
| 2012/0053638 A1 | 3/2012 | Rusch |
| 2012/0059425 A1 * | 3/2012 | Biedermann ........ A61B 17/861 |
| | | | 606/291 |
| 2012/0065690 A1 | 3/2012 | Perrow et al. |
| 2012/0078371 A1 | 3/2012 | Gamache et al. |
| 2012/0095513 A1 | 4/2012 | Humphreys |
| 2012/0136396 A1 | 5/2012 | Baker et al. |
| 2012/0143193 A1 | 6/2012 | Hulliger |
| 2012/0150240 A1 | 6/2012 | Medoff |
| 2012/0179207 A1 | 7/2012 | Mekhail et al. |
| 2012/0179208 A1 * | 7/2012 | Geissler ............. A61B 17/8042 |
| | | | 606/282 |
| 2012/0191141 A1 | 7/2012 | Costabile |
| 2012/0323284 A1 | 12/2012 | Baker et al. |
| 2013/0006247 A1 | 1/2013 | Weiner |
| 2013/0023938 A1 | 1/2013 | Huebner et al. |
| 2013/0023940 A1 | 1/2013 | Hansell et al. |
| 2013/0026206 A1 | 1/2013 | Fox |
| 2013/0030437 A1 | 1/2013 | Fox |
| 2013/0046346 A1 | 2/2013 | Thorwarth et al. |
| 2013/0109910 A1 | 5/2013 | Alexander et al. |
| 2013/0138154 A1 | 5/2013 | Reiley |
| 2013/0150900 A1 | 6/2013 | Haddad et al. |
| 2013/0218285 A1 | 8/2013 | Kleinman et al. |
| 2013/0226252 A1 | 8/2013 | Mayer |
| 2013/0238035 A1 | 9/2013 | Medoff |

(56) References Cited

U.S. PATENT DOCUMENTS

| | | |
|---|---|---|
| 2013/0267956 A1 | 10/2013 | Terrill et al. |
| 2013/0303071 A1 | 11/2013 | Seki |
| 2013/0325074 A1 | 12/2013 | Ziolo |
| 2013/0345752 A1 | 12/2013 | Hendren et al. |
| 2014/0014553 A1 | 1/2014 | Knight et al. |
| 2014/0018809 A1 | 1/2014 | Allen |
| 2014/0018862 A1 | 1/2014 | Koay et al. |
| 2014/0020333 A1 | 1/2014 | Knight et al. |
| 2014/0024002 A1 | 1/2014 | Knight et al. |
| 2014/0034702 A1 | 2/2014 | Miller et al. |
| 2014/0058461 A1 | 2/2014 | Black |
| 2014/0100652 A1 | 4/2014 | Drews et al. |
| 2014/0142628 A1 | 5/2014 | Traynelis et al. |
| 2014/0163621 A1 | 6/2014 | Huebner et al. |
| 2014/0163682 A1 | 6/2014 | Lott et al. |
| 2014/0163683 A1 | 6/2014 | Seifert et al. |
| 2014/0172026 A1 | 6/2014 | Biedermann et al. |
| 2014/0200670 A1 | 7/2014 | Chin et al. |
| 2014/0207195 A1 | 7/2014 | Appenzeller et al. |
| 2014/0222086 A1 | 8/2014 | Kuster |
| 2014/0276830 A1 | 9/2014 | Cheney |
| 2014/0296925 A1 | 10/2014 | Lawson et al. |
| 2014/0309639 A1 | 10/2014 | Averous et al. |
| 2014/0316470 A1 | 10/2014 | Hartdegen et al. |
| 2014/0358187 A1 | 12/2014 | Taber et al. |
| 2015/0012003 A1 | 1/2015 | Ryan et al. |
| 2015/0045804 A1 | 2/2015 | Orbay et al. |
| 2015/0066095 A1 | 3/2015 | Austin et al. |
| 2015/0080914 A1 | 3/2015 | Roundy et al. |
| 2015/0080969 A1 | 3/2015 | Holly et al. |
| 2015/0133940 A1 | 5/2015 | Palmer et al. |
| 2015/0142063 A1 | 5/2015 | Austin et al. |
| 2015/0148850 A1 | 5/2015 | Orbay et al. |
| 2015/0173749 A1 | 6/2015 | Shelton et al. |
| 2015/0173750 A1 | 6/2015 | Shelton et al. |
| 2015/0173751 A1 | 6/2015 | Shelton et al. |
| 2015/0173756 A1 | 6/2015 | Baxter et al. |
| 2015/0196333 A1 | 7/2015 | Austin et al. |
| 2015/0216570 A1 | 8/2015 | Hess et al. |
| 2015/0216573 A1 | 8/2015 | Chin et al. |
| 2015/0238191 A1 | 8/2015 | Schellin et al. |
| 2015/0282819 A1 | 10/2015 | Austin et al. |
| 2015/0313592 A1 | 11/2015 | Coillard-Lavirotte et al. |
| 2015/0320462 A1 | 11/2015 | Biedermann |
| 2015/0351762 A1 | 12/2015 | Vendely et al. |
| 2015/0351763 A1 | 12/2015 | Shelton et al. |
| 2015/0351764 A1 | 12/2015 | Shelton |
| 2016/0015384 A1 | 1/2016 | Roedl et al. |
| 2016/0066907 A1 | 3/2016 | Cheney et al. |
| 2016/0074037 A1 | 3/2016 | Cheney et al. |
| 2016/0089191 A1 | 3/2016 | Pak et al. |
| 2016/0100835 A1 | 4/2016 | Linder et al. |
| 2016/0157906 A1 | 6/2016 | Hollis et al. |
| 2016/0192930 A1 | 7/2016 | Finley et al. |
| 2016/0199060 A1 | 7/2016 | Morgan et al. |
| 2016/0242771 A1 | 8/2016 | Weinstein et al. |
| 2016/0242927 A1 | 8/2016 | Seifert et al. |
| 2016/0331372 A1 | 11/2016 | Nelson |
| 2016/0338697 A1 | 11/2016 | Biedermann et al. |
| 2016/0354117 A1 | 12/2016 | Nakaji |
| 2017/0000482 A1 | 1/2017 | Averous et al. |
| 2017/0000533 A1 | 1/2017 | Fallin et al. |
| 2017/0065276 A1 | 3/2017 | Weiner et al. |
| 2017/0065312 A1 | 3/2017 | Lauf et al. |
| 2017/0112553 A1 | 4/2017 | Hansell et al. |
| 2017/0119443 A1 | 5/2017 | Cawley et al. |
| 2017/0156776 A1 | 6/2017 | Weiman et al. |
| 2017/0164990 A1 | 6/2017 | Weiner et al. |
| 2017/0181779 A1 | 6/2017 | Leither et al. |
| 2017/0196606 A1 | 7/2017 | Cianfrani et al. |
| 2017/0202552 A1 | 7/2017 | Coleman et al. |
| 2017/0202585 A1 | 7/2017 | Leak et al. |
| 2017/0209193 A1 | 7/2017 | Hartdegen et al. |
| 2017/0231625 A1 | 8/2017 | Handie |
| 2017/0238974 A1 | 8/2017 | Konieczynski et al. |
| 2017/0245901 A1 | 8/2017 | Grigorian et al. |
| 2017/0281157 A1 | 10/2017 | Hartdegen et al. |
| 2017/0354509 A1 | 12/2017 | Finley et al. |
| 2018/0000592 A1 | 1/2018 | Mayer et al. |
| 2018/0296257 A1 | 10/2018 | Penzimer et al. |
| 2018/0317906 A1 | 11/2018 | Hollis et al. |
| 2018/0353172 A1 | 12/2018 | Hartdegen et al. |
| 2019/0000451 A1 | 1/2019 | Majors et al. |
| 2019/0046182 A1 | 2/2019 | Krumme |
| 2019/0046183 A1 | 2/2019 | Hartdegen et al. |
| 2019/0150921 A1 | 5/2019 | Fonte et al. |
| 2020/0000464 A1 | 1/2020 | Gaston et al. |
| 2020/0000465 A1 | 1/2020 | Maclure et al. |
| 2020/0008807 A1 | 1/2020 | Hollis |
| 2020/0275957 A1* | 9/2020 | Biedermann ........ A61B 17/809 |

FOREIGN PATENT DOCUMENTS

| | | |
|---|---|---|
| DE | 3119550 | 12/1982 |
| DE | 29721858 | 2/1998 |
| DE | 20001879 | 3/2000 |
| EP | 0092383 | 10/1983 |
| EP | 0682920 | 11/1995 |
| EP | 0768062 | 4/1997 |
| EP | 0826340 | 3/1998 |
| EP | 0857462 | 8/1998 |
| EP | 1870042 | 12/2007 |
| FR | 2628312 | 9/1989 |
| FR | 2694696 | 2/1994 |
| FR | 2725126 | 4/1996 |
| FR | 2874166 | 2/2006 |
| FR | 2874316 | 2/2006 |
| FR | 2927527 | 8/2009 |
| FR | 2935256 | 3/2010 |
| FR | 2980966 | 4/2013 |
| GB | 2471648 | 1/2011 |
| WO | WO1992017122 | 10/1992 |
| WO | WO2001056489 | 8/2001 |
| WO | WO2008129061 | 10/2008 |
| WO | WO2009091770 | 7/2009 |
| WO | WO2010004602 | 1/2010 |
| WO | WO2013186205 | 12/2013 |
| WO | WO2015004391 | 1/2015 |

OTHER PUBLICATIONS

DePuy Synthes, BME Elite Continuous Compression Implant, (May 2017), 3 pp.

MedShape, Inc., DynaClip Bone Fixation System Procedure Guide, (2018, Rev. May 2020), 2 pp.

MedShape, Inc., DynaClip Forte Bone Fixation System Product Information Sheet, (May 2020), 2 pp.

* cited by examiner
BONE PLATES WITH DYNAMIC ELEMENTS AND SCREWS

CROSS-REFERENCE TO RELATED APPLICATIONS

This application claims the benefit of U.S. Provisional Patent Application Ser. No. 63/059,844 filed on Jul. 31, 2020, entitled "Bone Plates with Dynamic Elements Screws", which is hereby incorporated by reference in its entirety.

TECHNICAL FIELD

The present disclosure relates to plates having dynamic elements, otherwise known as elastic elements. Plates with dynamic elements may be used to stabilize and apply continuous load to hard tissues such as bone, or to soft tissues such as cartilage or ligaments. More specifically, the present disclosure relates to plates with dynamic elements that provide continuous load across a joint, a resection, an osteotomy, a fracture, a tear, a laceration, or some other discontinuity between hard or soft tissue portions. The continuous load may be compressive or tensile.

BACKGROUND

There are many circumstances in which bones, bone fragments, or other tissue portions such as cartilage must be fused together, united, or otherwise permanently joined. Some examples include arthrodesis, corrective osteotomy, fracture, tear, or laceration. Bones, bone fragments, or other tissue portions heal better when they are stabilized with some mechanical load or stress across the discontinuity, for example when the bones, bone fragments, or other tissue portions are compressed together or distracted apart, with or without an intervening bone graft. This disclosure describes solutions to the problem of stabilizing bones, bone fragments, or other tissue portions while applying a therapeutic level of continuous mechanical load or stress across the discontinuity.

SUMMARY

The various systems and methods of the present technology have been developed in response to the present state of the art, and in particular, in response to the problems and needs in the art that have not yet been fully solved by currently available fixation systems. The systems and methods of the present technology may provide a means for dynamic loading while providing an overall stable construct.

In an embodiment, a bone plate assembly couplable to a tissue may include a bone plate that has an obverse side and a reverse side. In an embodiment, the bone plate may include one or more fastener holes formed through the bone plate from the obverse side to the reverse side. One or more draw holes may also be formed through the bone plate from the obverse side to the reverse side. These draw holes may include a wire engagement surface used to receive a wire therein. A fastener used to couple the bone plate to the tissue may include a distal end insertable through the fastener hole and into the tissue and a proximal end retainable in the fastener hole. The wires may be insertable into the one or more draw holes with each wire including a distal end anchorable in the tissue and a proximal end that is removable such that a retention portion of the wire is retainable in the one or more draw holes. The wire engagement surface of the one or more draw holes may be oriented obliquely such that motion of the wires through their respective draw holes exerts a compressive force against the tissue. The wire may include a sharpened tip at the distal end of the wire used to pass the wire a distance into the tissue. In this manner, a break, osteotomy, or other discontinuity in the tissue may be fixed allowing the tissue to recuperate.

In an embodiment, the bone plate may include the one or more draw holes formed through the bone plate from the obverse side to the reverse side, without a fastener, in order to secure the bone plate to the tissue. In this embodiment, the draw holes may include the wire engagement surfaces such that the wires may be insertable into the one or more draw holes. Again, each wire may include a distal end anchorable in the tissue and a proximal end that is removable such that a retention portion of the wire is retainable in the one or more draw holes. The wire engagement surface of the one or more draw holes, in this embodiment, may similarly be oriented obliquely to any holes formed in the tissue such that motion of the wires through their respective draw holes exerts a compressive force against the tissue.

In an embodiment, the fastener hole may include a threaded portion. This threaded portion allows the fastener, such as a locking screw, to engage the threaded portion with an engagement thread at the proximal end of the locking screw. This may allow the locking screw to be seated into the bone plate during assembly.

In an embodiment, the bone plate assembly may further include a leg. The leg may include a distal leg end insertable into the tissue and a proximal leg end that includes a wire channel formed from the proximal leg end toward the distal leg end. In these embodiments, the wire channel may be sized to receive the distal end of the wire. The leg may be used to provide additional support within the tissue to secure the wires into the tissue. The leg further may include an insertion tip formed into a tapered shape to initiate insertion into the tissue and retention features protruding outward from a longitudinal axis of the leg and shaped to increase the friction between the leg and the tissue when inserted into the tissue.

In an embodiment, the number of draw holes is two. In this embodiment, a second draw hole may include a second wire engagement surface wherein insertion of the first wire into the first draw hole and insertion of a second wire into a second draw hole causes a compression force to be placed against two pieces of tissue to draw and compress the two pieces of tissue together. In other embodiments, a draw plug may be formed and placed within a draw plug hole formed in the bone plate. In this embodiment, a first draw plug hole may be formed through the bone plate from the obverse side to the reverse side to receive a first draw plug. The first draw plug may include the first draw hole formed therethrough and may include a lip that interfaces with a recess formed on the bone plate to prevent the draw plug from exiting the first draw plug hole when the bone plate is installed. It is this draw hole, in this embodiment, that the wire is passed through and into the tissue. In an embodiment, the draw plug hole may include a non-circular cross-section shape that interfaces with an internal surface portion formed within the first draw plug hole to prevent the first draw plug from rotating within the first draw plug hole.

The present specification further describes a bone plate assembly to be coupled to a tissue that includes a bone plate, the bone plate. The bone plate may have an obverse side and a reverse side. The bone plate may also include a first fastener hole formed through the bone plate from the obverse side to the reverse side. The bone plate may further include a second fastener hole formed through the bone plate from the obverse side to the reverse side. The bone plate may also include a first draw hole formed through the bone plate from the obverse side to the reverse side with a first wire engagement surface. In this embodiment, the bone plate also includes a second draw hole formed through the bone plate from the obverse side to the reverse side with the second draw hole including a second wire engagement surface. In this embodiment, a first fastener is used to secure the bone plate to the tissue and includes a distal end insertable through the first fastener hole and into the tissue and a proximal end retainable in the first fastener hole. In this embodiment, a second fastener may also be used to secure the bone plate to the tissue and may include a distal end insertable through the second fastener hole and into the tissue and a proximal end retainable in the second fastener hole. A first wire is insertable into the first draw plug hole and includes a distal end anchorable in the tissue and a proximal end with a retention portion that is retainable in the first draw hole. A second wire is insertable into the second draw hole and may include a distal end anchorable in the tissue and a proximal end with a retention portion that is retainable in the second draw hole. Each of the first wire and second wire comprise a sharpened distal tip used to pass the second wire a distance into a tissue. In this embodiment, the distal ends of the first draw hole and second draw hole extend away from each other.

In an embodiment, the first fastener hole includes a first threaded portion with the second fastener hole also including a second threaded portion. In this embodiment, the first fastener and the second fastener are locking screws. The first fastener may include, in an embodiment, a first engagement thread at the proximal end of the first fastener and a second engagement thread at the proximal end of the second fastener. The first engagement thread and second engagement thread are to engage with the first threaded portion of the first fastener hole and second threaded portion of the second fastener hole, respectively.

In an embodiment the bone plate assembly may include a leg. The leg may include a distal leg end insertable into the tissue and a proximal leg end that includes a wire channel formed from the proximal leg end toward the distal leg end. In this embodiment, the wire channel is sized to receive the distal end of the first wire or second. In an embodiment, the leg further includes an insertion tip formed into a tapered shape to initiate insertion into the tissue and retention features protruding outward from a longitudinal axis of the leg and shaped to increase the friction between the leg and the tissue when inserted into the tissue.

In an embodiment, the bone plate may include a first draw plug hole formed through the bone plate from the obverse side to the reverse side to receive a first draw plug. Here, the first draw plug includes the first draw hole formed therethrough and a lip that interfaces with a recess formed on the bone plate to prevent the first draw plug from exiting the first draw plug hole when the bone plate is installed. The bone plate, in this embodiment, may also include a second draw plug hole formed through the bone plate from the obverse side to the reverse side to receive a second draw plug. Here, the second draw plug includes the second draw hole formed therethrough and a lip that interfaces with a recess formed on the bone plate to prevent the second draw plug from exiting the second draw plug hole when the bone plate is installed. In an embodiment, the first draw plug and a second draw plug further include a non-circular cross-sectional shape that interfaces with a non-circular cross-sectional shaped internal surface portion formed within the first draw plug hole and second draw plug hole to prevent the first draw plug and second draw plug, respectively, from rotating within the first draw plug hole and second draw plug hole.

The present specification further describes a method of assembling a bone plate assembly to be coupled to a tissue including placing a bone plate on a tissue. Here, the bone plate includes a first fastener hole formed through the bone plate from an obverse side of the bone plate to a reverse side of the bone plate and a first draw hole formed through the bone plate, the first draw plug hole comprising a wire engagement surface. The method also includes passing a first fastener through the first fastener hole. The first fastener may include a distal end insertable through the first fastener hole and into the tissue and a proximal end with a retention portion retainable in the first fastener hole. The method also includes passing a first wire through the first draw hole after the wire has been passed into the tissue.

In an embodiment, this method may also include trimming a portion of the first wire that extends above an obverse side. This may be conducted when the bone plate has been seated and abuts the tissue.

In an embodiment, this method may also include placing a wire template over a discontinuity in the tissue. Here the wire template may include a guide hole. The method further includes, in this embodiment, drilling a pilot hole at the location of the guide hole into the tissue and using the pilot hole to pass the first wire into the tissue.

This method may also include placing a leg into the pilot hole prior to passing the wire into the tissue. In this embodiment, the leg may include a distal leg end insertable into the tissue and a proximal leg end comprising a wire channel formed from the proximal leg end toward the distal leg end.

In an embodiment, this method may further include pressing the bone plate against the tissue to distort the first wire passing through the first draw hole as a result of the first draw hole being oblique relative to a pilot hole formed in the tissue.

To achieve the foregoing, and in accordance with the technology as embodied and broadly described herein, plate members provide stabilization and/or deformity correction in conjunction with dynamic elements that provide continuous dynamic load between tissue portions. The plate members may or may not be used with the dynamic elements. The dynamic elements may be separate parts that may be attached to the plate members, or they may be integrally formed with the plate members. The plate members and the dynamic elements may be made from the same materials or from different materials. The dynamic elements may be made from any elastic material, preferably a highly elastic metal, preferably a super-elastic metal, preferably nitinol.

These and other features and advantages of the present technology will become more fully apparent from the following description and appended claims, or may be learned by the practice of the technology as set forth hereinafter.

BRIEF DESCRIPTION OF THE DRAWINGS

Exemplary embodiments of the technology will become more fully apparent from the following description and appended claims, taken in conjunction with the accompanying drawings. Understanding that these drawings depict only exemplary embodiments and are, therefore, not to be considered limiting of the scope of the technology, the exemplary embodiments will be described with additional specificity and detail through use of the accompanying drawings in which:

DETAILED DESCRIPTION

Figure 1:
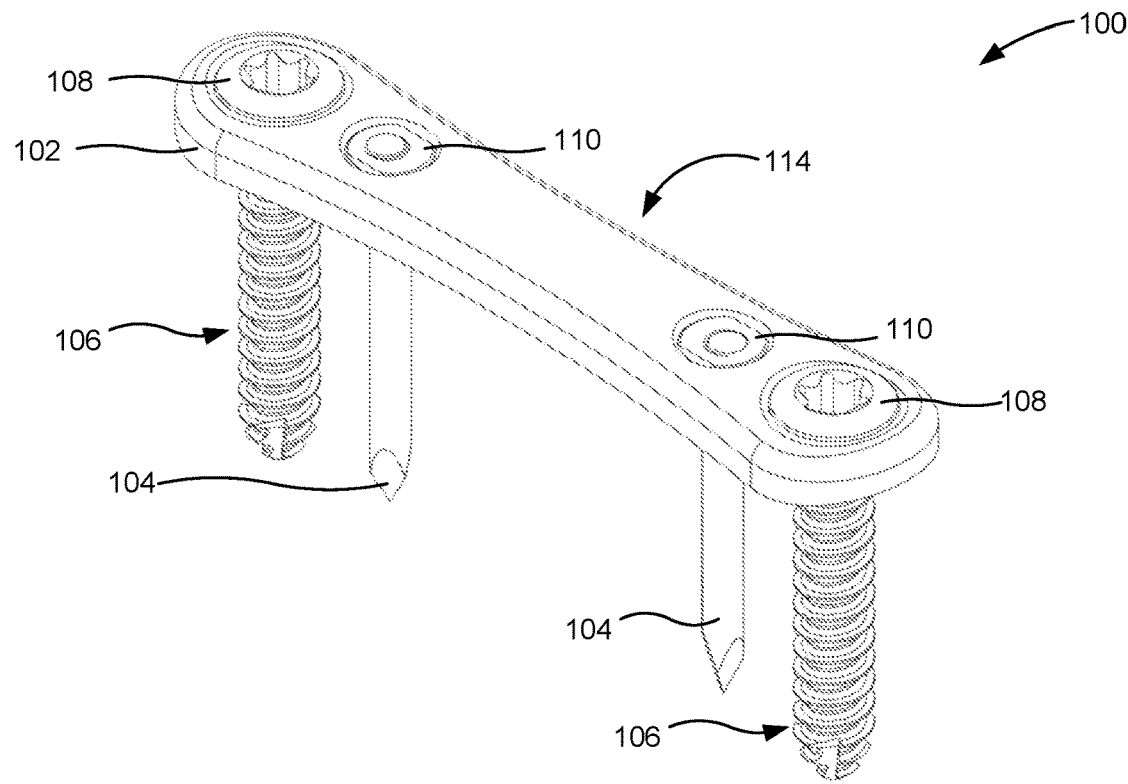
FIG. 1 is a top, oblique view of an assembly with a bone plate, wires, and screws.
Figure 2:
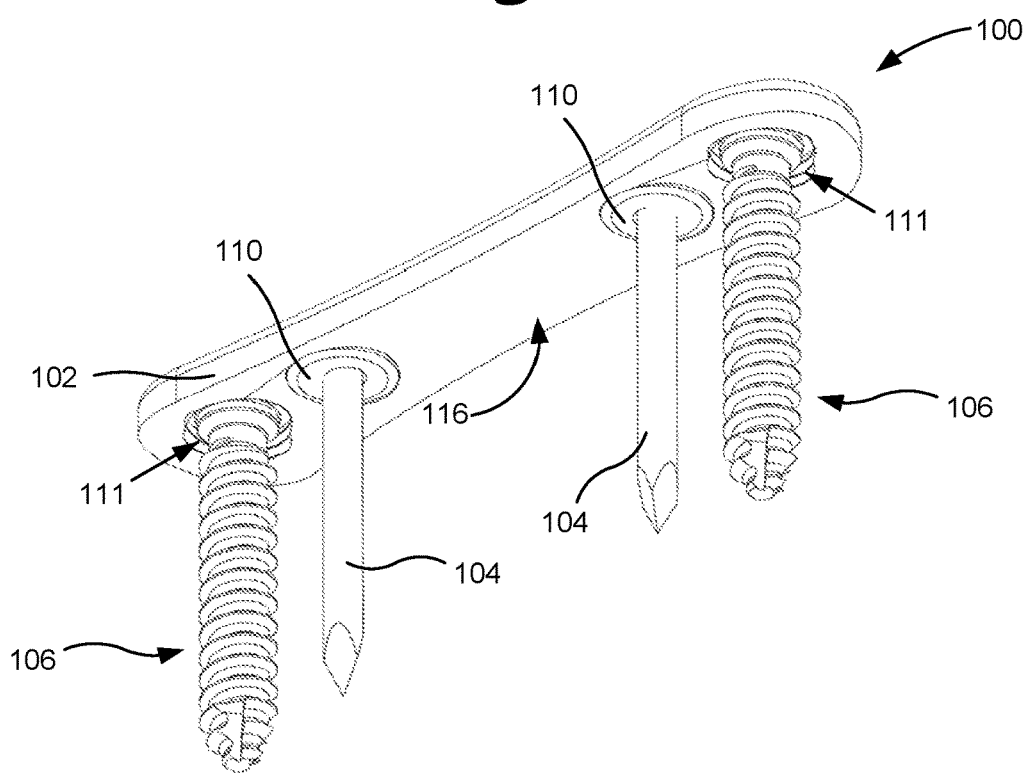
FIG. 2 is a bottom, oblique view of an assembly with a bone plate, wires, and screws.
Figure 3:
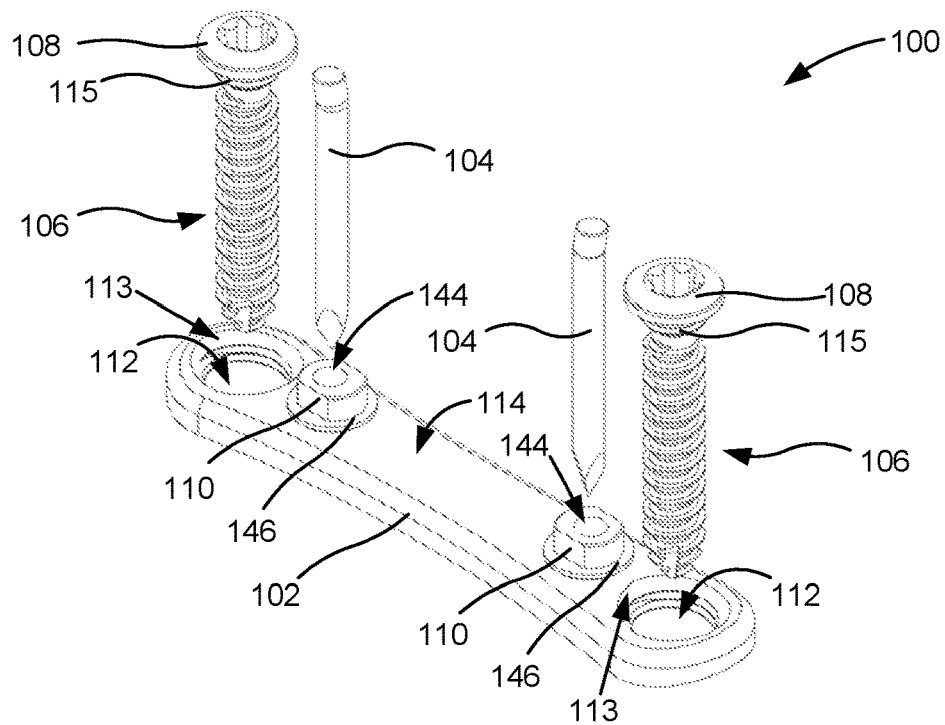
FIG. 3 is a top, oblique, exploded view of an assembly with a bone plate, wires, and screws.
Figure 4:
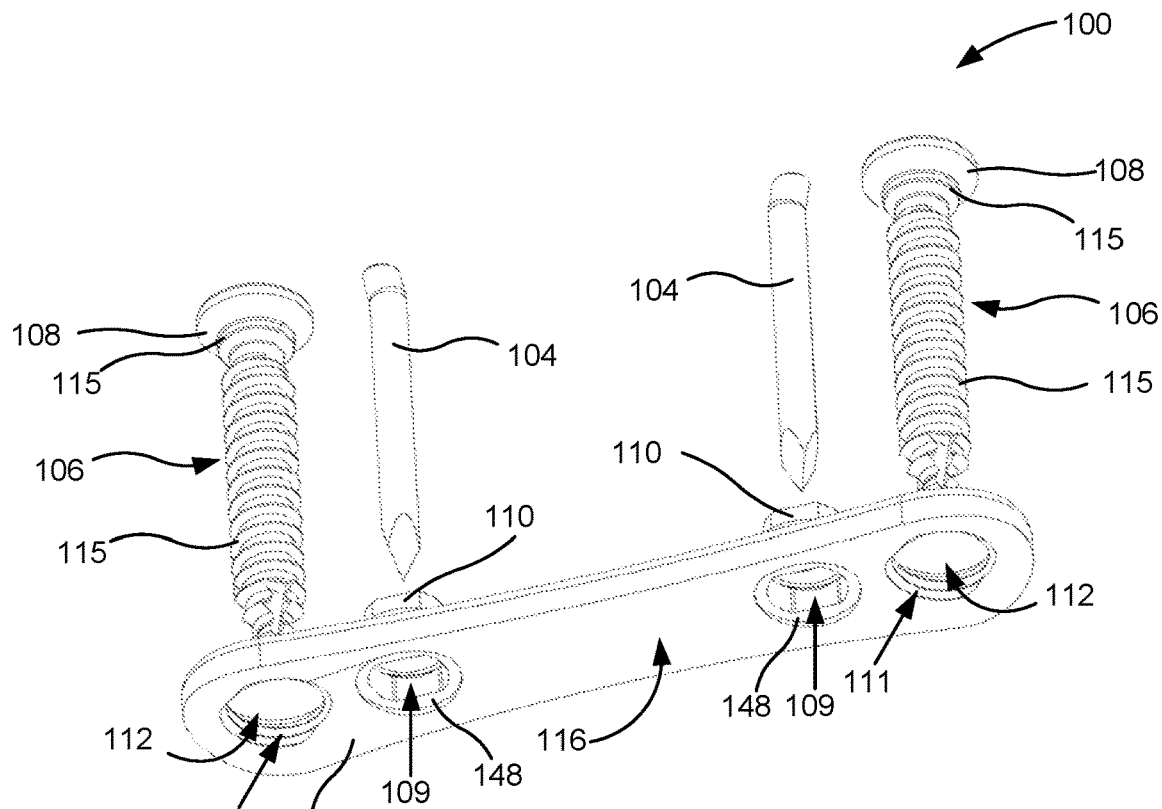
FIG. 4 is a bottom, oblique, exploded view of an assembly with a bone plate, wires, and screws.

Exemplary embodiments of the technology will be best understood by reference to the drawings, wherein like parts are designated by like numerals throughout. It will be readily understood that the components of the technology, as generally described and illustrated in the figures herein, could be arranged and designed in a wide variety of different configurations. Thus, the following more detailed description of the embodiments of the apparatus, system, and method is not intended to limit the scope of the invention, as claimed, but is merely representative of exemplary embodiments of the technology.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

Standard medical planes of reference and descriptive terminology are employed in this specification. While these terms are commonly used to refer to the human body, certain terms are applicable to physical objects in general.

A standard system of three mutually perpendicular reference planes is employed. A sagittal plane divides a body into right and left portions. A coronal plane divides a body into anterior and posterior portions. A transverse plane divides a body into superior and inferior portions. A mid-sagittal, mid-coronal, or mid-transverse plane divides a body into equal portions, which may be bilaterally symmetric. The intersection of the sagittal and coronal planes defines a superior-inferior or cephalad-caudal axis. The intersection of the sagittal and transverse planes defines an anterior-posterior axis. The intersection of the coronal and transverse planes defines a medial-lateral axis. The superior-inferior or cephalad-caudal axis, the anterior-posterior axis, and the medial-lateral axis are mutually perpendicular.

Anterior means toward the front of a body. Posterior means toward the back of a body. Superior or cephalad means toward the head. Inferior or caudal means toward the feet or tail. Medial means toward the midline of a body, particularly toward a plane of bilateral symmetry of the body. Lateral means away from the midline of a body or away from a plane of bilateral symmetry of the body. Axial means toward a central axis of a body. Abaxial means away from a central axis of a body. Ipsilateral means on the same side of the body. Contralateral means on the opposite side of the body. Proximal means toward the trunk of the body. Proximal may also mean toward a user or operator. Distal means away from the trunk. Distal may also mean away from a user or operator.

In this specification, standard tissue anatomical terms are employed with their ordinary and customary meanings.

Referring to FIGS. 1-5, an assembly 100 may include a stabilizing member, a dynamic element, and one or more fasteners. In the assembly 100, the stabilizing member may be a bone plate 102, the dynamic element may be a wire 104 or a set of wires 104, and the fasteners may be screws 106. In an embodiment, the screws 106 of the assembly 100 may include locking screws, non-locking screws, fixed angle screws, bone screws, or poly-axial screws. Although the embodiments described herein show specific features and elements, these specific features and elements are not meant to limit the aspects of those embodiments. The present specification describes a means for accepting a dynamic element at a bone plate in order to impart a force in a direction relative to the plate and the present specification contemplates that other designed elements and features may be used to accomplish this purpose without departing from the scope of the present specification.

The bone plate 102 has an obverse side 114 and a reverse side 116. When the bone plate 102 is implanted or otherwise attached to a tissue (e.g., bone), the obverse side 114 faces away from the tissue portions and the reverse side 116 faces toward and/or abuts the tissue portions. The bone plate 102 may be made of a medical grade metal or plastic that allows for implantation into the human body. In an embodiment, the bone plate 102 may be made of a bendable material that is capable of deformation to fit across a portion of tissue within the human body. In a specific embodiment, the bone plate 102 may be deformed to conform against a broken bone such as a foot bone within the human body.

In an embodiment, the bone plate 102 may include one or more fastener holes referred herein as screw holes 112 which extend through the obverse side 114 and reverse side 116. Although the present specification describes these fastener holes as screw holes 112, the present specification contemplates that because any type of fastener may be used to secure the bone plate 102 to the tissue, any type of fastener hole may be formed through the bone plate 102 to facilitate this function. Alternatively, the pins 104 may be the only components fastening the bone plate to the tissue. For ease of understanding in certain embodiments, these fastener holes are referred to as screw holes 112. Two screw holes 112 are illustrated in FIGS. 1-5, although any number of screw holes 112 may be present in the bone plate 102. In an embodiment, a single screw hole 112 may be formed. In some embodiments, the size of the bone plate 102 may be sized to fit across any portion of tissue including any bone or cartilage within the human body. In these embodiments, the size of the bone plate 102 to be used on a femur bone may be relatively larger than a bone plate 102 used to be used on a bone within the foot such as a cuneiform bone. The bone plate 102 may have an elongated, generally oval shape as shown, or any other shape or contour suited to its intended implantation site. The present specification contemplates, however, that the bone plate 102 may not include any fastener holes relying on the wires described herein to secure the bone plate to the tissue. For ease of explanation of the drawings presented herein, the bone plate is described as including at least one fastener hole or more.

In an embodiment, each screw hole 112 formed through the bone plate 102 may include an internally threaded portion 111 and a nonthreaded portion 113 so that each screw hole 112 accepts either one of a locking screw or a non-locking screw (among other types of screws including bone screws). In an embodiment, an internal threaded portion 111 of the screw hole 112 may engage corresponding threads 115 formed on the screw head 108 in order to lock the screw 106 to the bone plate 102. In this embodiment, the screw 106 may be locked into the screw hole 112 when the screw 106 is fully seated into the screw hole 112. In an embodiment, the screw 106 is not a locking screw (such as a bone screw) such that the screw holes 112 of the bone plate 102 do not include a threaded portion or the threaded portions 111 are not used to seat the non-locking screw into the bone plate. Whether the fastener is a locking screw or a non-locking screw, however, these fasteners may be removable once the tissue has recuperated (e.g., bone has fused together).

In an embodiment, the screw 106 may include a screw head 108 with an exterior surface that fits within the screw hole 112 such that the screw head 108 at least partially sunk into the bone plate 102. The exterior surface may be convex, spherical, or conical. In an embodiment, the placement of the screw head 108 relative to the bone plate 102 may be such that the screw head 108 does not protrude beyond a top plane on the obverse side 114 of the bone plate 102. This may prevent tissues within the body from rubbing against the screw head 108. In a specific embodiment, the screw 106 may have a 3.5 mm diameter and lengths from 8 mm to 30 mm in 2 mm increments. In an embodiment, the threads of the screw 106 formed below the screw head 108 may have a pitch and thread height sufficient to hold the bone plate 102 to the tissue when the screw 106 is fully sunk into the tissue. In an embodiment, the screw head 108 may include any type of screw drive that allows a clinician to interface a screwdriver with the screw drive in order to drive the screw 106 into the tissue.

The bone plate 102 of the assembly 100 may further include one or more draw holes 144 through which a wire may be passed. In an embodiment, the draw hole 144 may be a hole formed from an obverse side 114 of the bone plate 102 to the reverse side 116 of the bone plate 102 as shown in, for example, in FIGS. 28 through 30. In another embodiment, the draw holes 144 may be formed through each of one or more draw plugs 110. In this embodiment, the draw plugs 110 may be formed into or placed within the body of the bone plate 102. In an embodiment, the draw plugs 110 may be coupled to the body of the bone plate 102. For example, where the draw plugs 110 are formed into the body of the bone plate 102, each draw plug 110 may be welded into or otherwise affixed within a draw plug hole 109 formed through the bone plate 102. In the embodiments shown in FIGS. 1-5, the draw plugs 110 are placed into draw plug holes 109 which extend through the obverse side 114 to the reverse side 116. When the draw plugs 110 are inserted into the draw plug holes 109, a decision as to whether to permanently weld them or affix them into the draw plug holes 109 may be made here.

In an embodiment, the draw plug holes 109 formed through the bone plate 102 may have an interior surface that interfaces with an exterior surface of the draw plug 110 such that when the draw plug 110 is installed into the draw plug holes 109, the draw plug 110 is prevented from rotating within the draw plug holes 109. In the embodiments presented herein, the interior surfaces of any of the draw plug holes 109 may have any number of surfaces that create a fit (e.g., interference fit, clearance fit, transition fit among others) with the exterior surfaces of the draw plugs 110 to prevent the draw plug 110 from rotating within the draw plug holes 109 such as any non-circular cross-section shape. Hex, hexalobe, square, D-shaped, and other non-circular shapes are contemplated for the interior surfaces of the draw plug holes 109 and the exterior surfaces of the draw plugs 110. The non-circular shapes may permit a draw plug 110 to be inserted into a draw plug hole 109 in a single orientation (i.e., D-shape) or multiple orientations (i.e., hex or multi-lobe shapes) thereby changing the direction of resultant compression in the final construct. Additionally, the non-circular shapes of the draw plugs 110 interfacing with the non-circular cross-sectional internal surface prevent the draw plug 110 from rotating within the draw plug hole 109.

Figure 28:
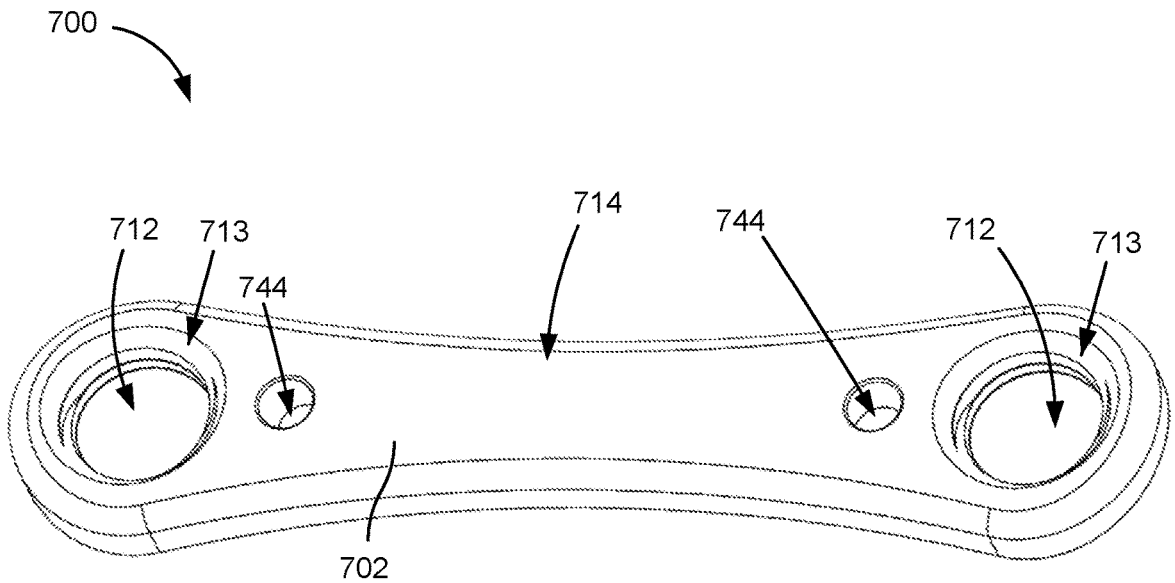
FIG. 28 is a top, oblique view of a bone plate.
Figure 29:
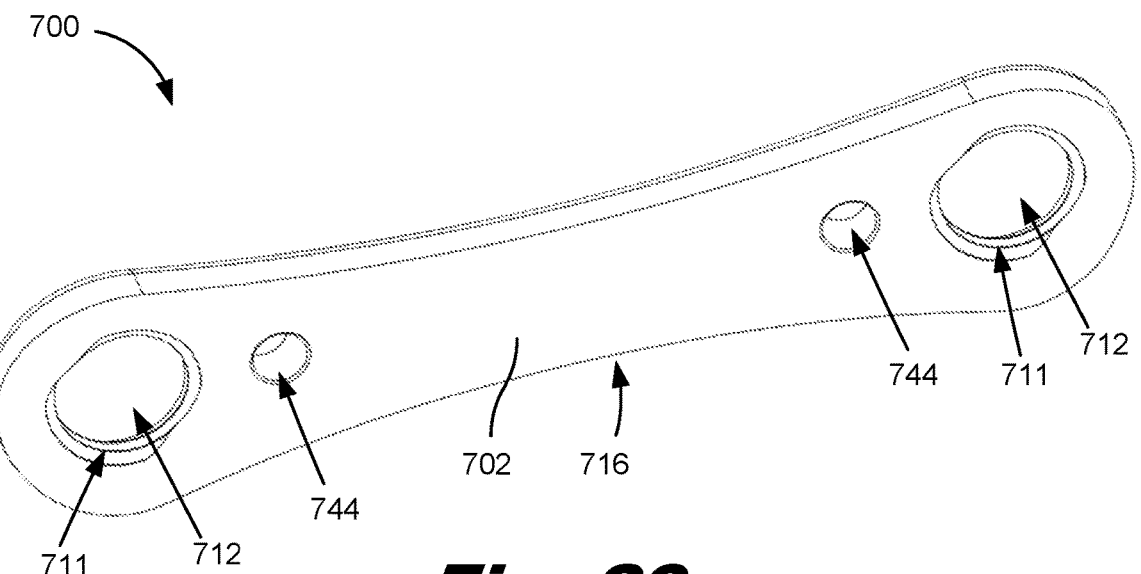
FIG. 29 is a bottom, oblique view of a bone plate.
Figure 30:
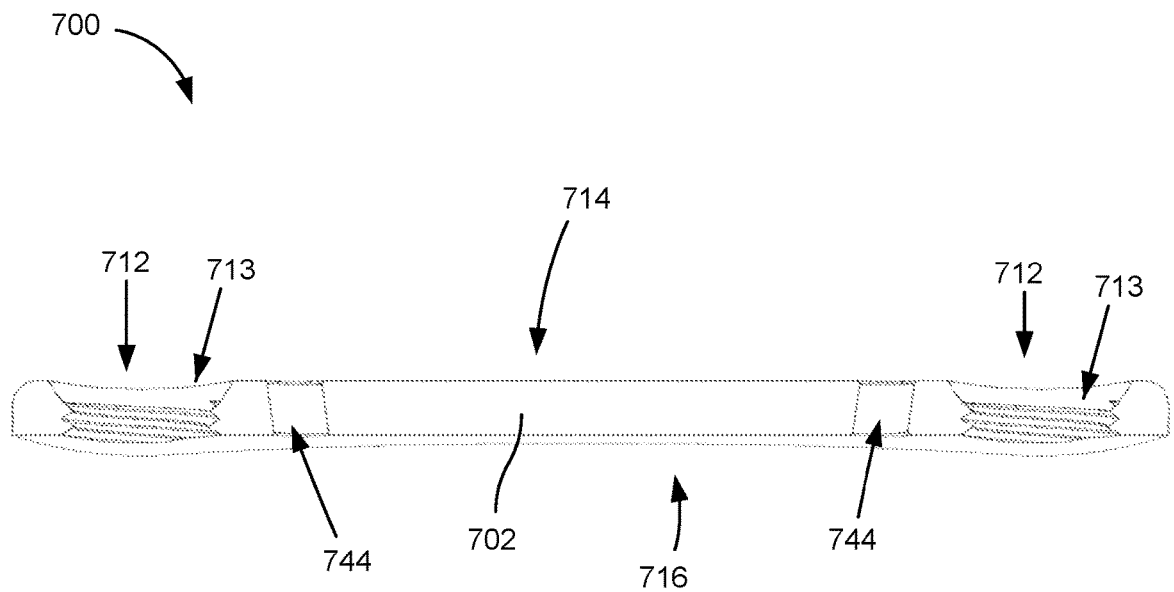
FIG. 30 is a longitudinal cross-section of a bone plate.
Figure 31:
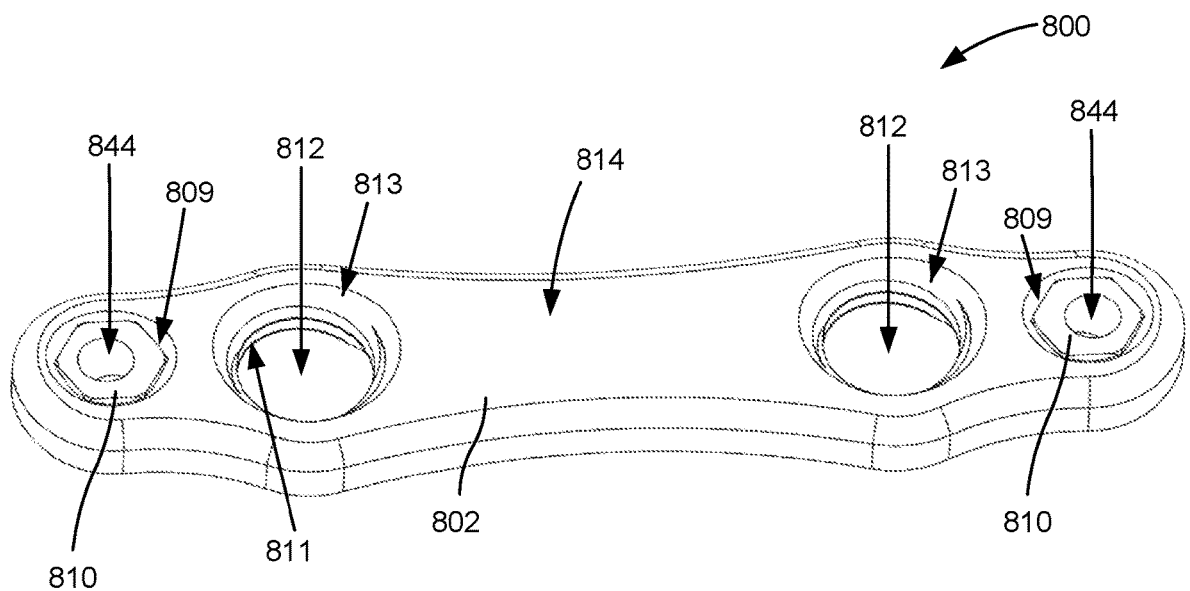
FIG. 31 is a top, oblique view of an assembly with a bone plate and draw plugs.
Figure 32:
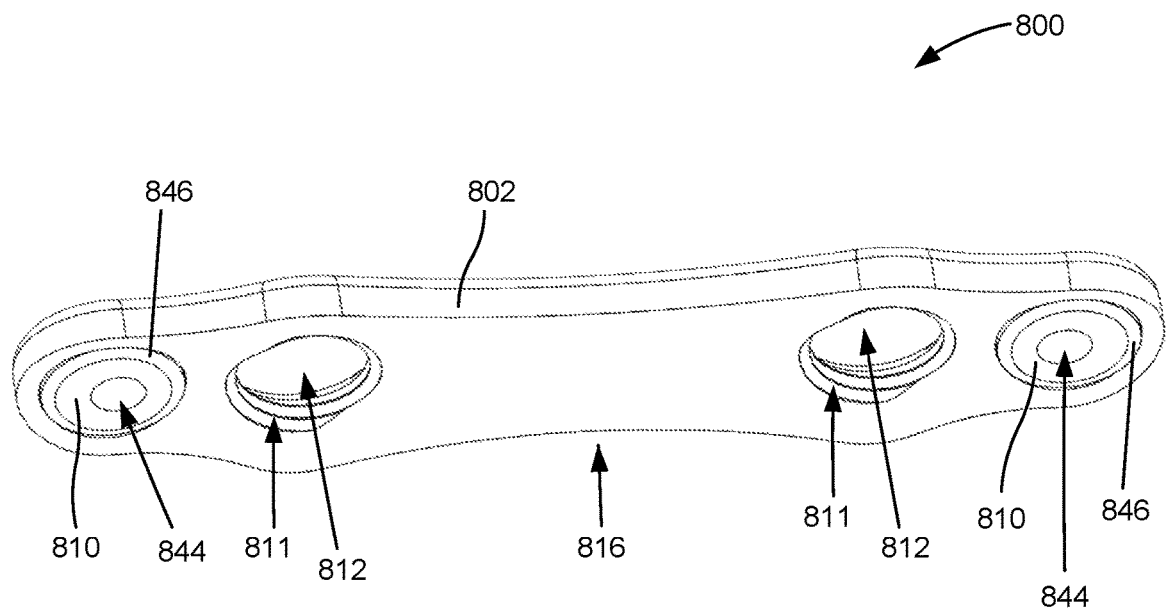
FIG. 32 is a bottom, oblique view of an assembly with a bone plate and draw plugs.
Figure 33:
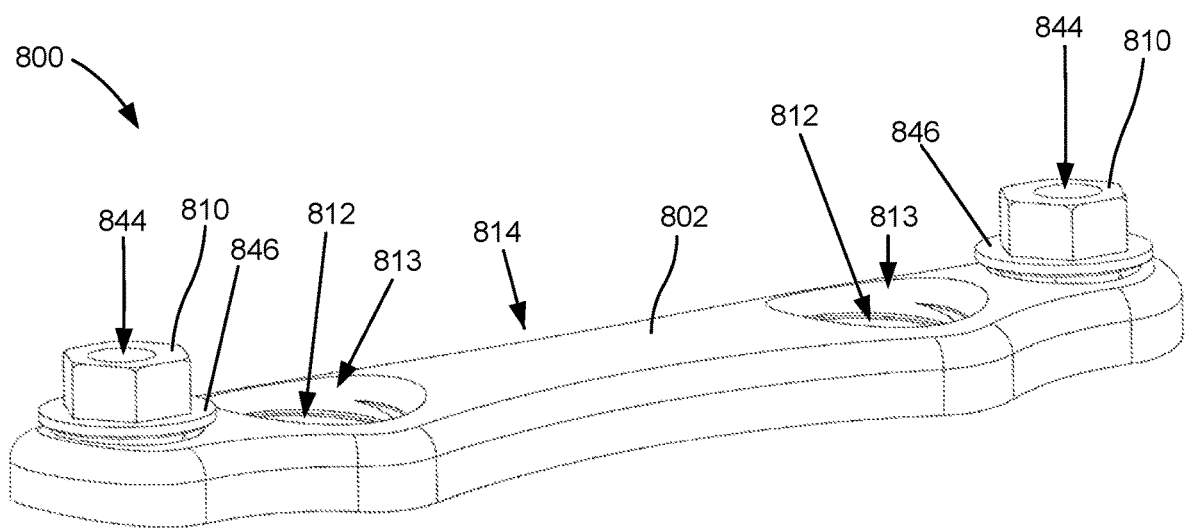
FIG. 33 is a top, oblique, exploded view of an assembly with a bone plate and draw plugs.

In another embodiment, the draw plug holes 109 may be formed through the bone plate 102 as described herein and in more detail in connection with FIGS. 28-30. In this embodiment, the separate draw plugs 110 may be eliminated reducing the component parts of the assembly 100. In this specific embodiment, the draw hole 144 formed through the bone plate 102 is not perpendicular to a top surface of the bone plate 102. As is described herein, the angle of the draw hole 144 may be set such that, as wires 104 are passed through the draw hole 144, the wire 104 is biased or bent so as to bring two individual pieces of tissue together. Although the elimination of the draw plugs 110 in this embodiment reduces the number of components of the assembly 100, the ability to orient the angles of the draw holes 144 relative to the tissue is reduced. In these embodiments, the angle of the draw hole 144 may be formed such that it imparts the same or similar moment on the wire 104 as the draw plug imparts and an elastic moment on the tissue in the alternative embodiments described herein. In the embodiments described herein, the draw plug 110 may or may not be included as a separate part of the assembly 100 and the present specification contemplates these alternative embodiments.

In addition to the exterior surfaces of the draw plug 110 that match with the interior surfaces of the draw plug holes 109, the draw plug 110 may include a lip 146 that interfaces with a circular recess 148 formed on the bone plate 102 in an embodiment. The circular recess 148 and lip 146 may prevent the draw plug 110 from exiting the draw plug hole 109 and the bone plate 102 by interfacing the lip 146 with the circular recess 148 formed on the reverse side 116 of the bone plate 102. Consequently, when the assembly 100 is affixed to the tissue as described herein, the lip 146 may be trapped between the tissue and the reverse side 116 of the bone plate 102 and within the circular recess 148 so that the draw plug 110 cannot be removed from the assembly 100. In another example, the draw plugs 110 may be retained to the bone plate 102 by welding the draw plugs 110 to the bone plate or via another bonding method or via mechanical interconnection between the exterior of the draw plug 110 and the interior of the draw plug hole 109.

Figure 5:
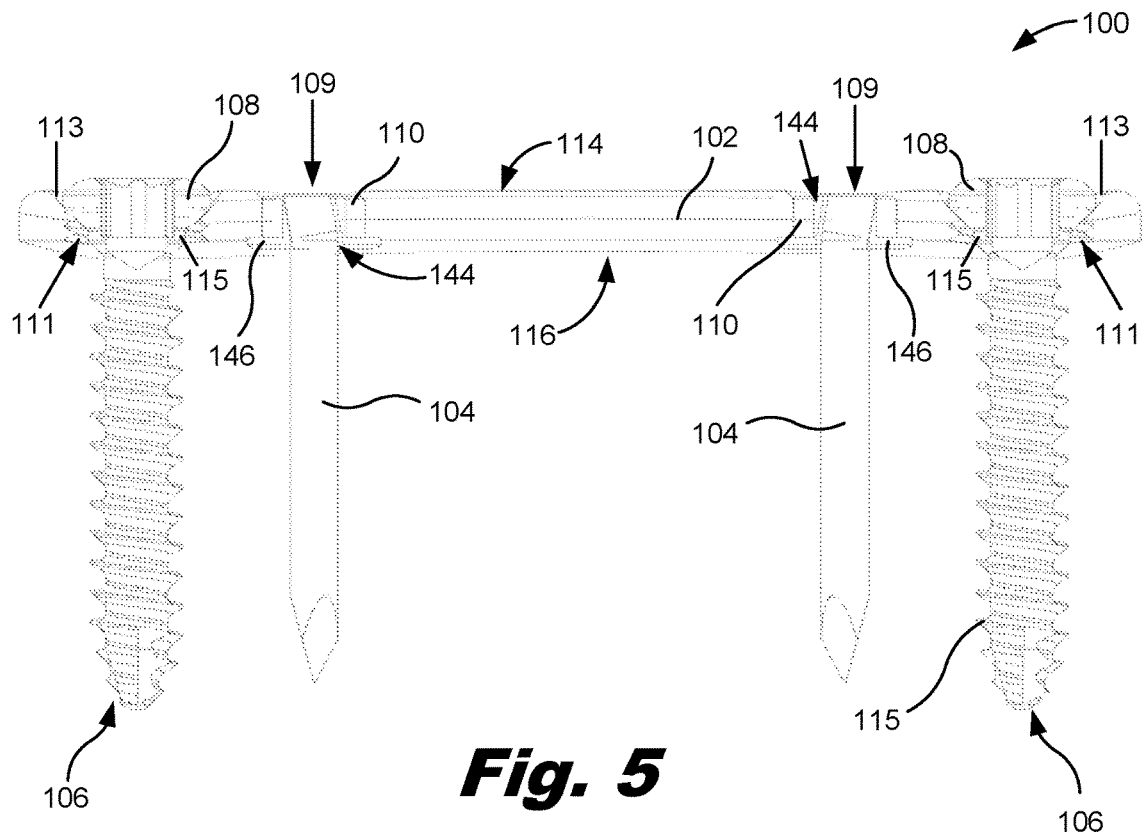
FIG. 5 is a longitudinal cross-section of an assembly with a bone plate, wires, and screws.

The draw plugs 110 include a draw hole 144 through which a wire 104 may be passed during assembly of the assembly 100 and coupling to the tissue as described herein. This draw hole 144 in FIG. 5 shows a longitudinal cross-section of an assembly 100 with the bone plate 102, wires 104, and screws 106. The draw hole 144 formed through the draw plug 110 may be formed at an oblique angle relative to, for example, a pilot hole formed in the tissue. That is, the draw hole 144 formed through the draw plug 110 is not perpendicular to a top surface of the draw plug 110 such that the wire 104 is biased or bent when the bone plate 102 is coupled thereto.

In another embodiment, the draw hole 144 may be formed in the draw plug 110 (or directly through the plate 102 in alternative embodiments) in a non-perpendicular or oblique direction relative to the top surface of the bone plate 102. In this embodiment, the initial placement of the wires 104 may be such that the distal ends of the wires 104 are diverging. This embodiment achieves a similar result of the other embodiments described herein by creating a moment on the wires 104 which would result in the compression of the tissue.

During installation of the assembly 100, the wire 104 may be previously inserted into a bone or other tissue of the body such that when the wire 104 is inserted through the draw hole 144, the wire 104 is biased or bent. By inserting the wires 104 through the draw hole 144 and pressing the bone plate 102 towards the tissue, a force (e.g., compression force) is applied to the tissue as described herein. In a specific example, the oblique angle of the draw hole 144 provides compression to be placed on neighboring pieces of tissue such that, during installation, the wires 104 cause the tissue pieces to be brought together. In these embodiments, the angles of the draw holes 144 in the draw plugs 110 (or any other draw hole 144) may cause the individual wires 104 to be moved together such that as the wires 104 that had been inserted into the tissue compress the tissue together as the bone plate 102 is pressed towards the tissue. In an embodiment, the draw plug 110 may be made of polyether ether ketone (PEEK), or another implantable polymer so that as the wires 104 are passed through the draw holes 144 the friction between the draw plugs 110 and the wires 104 is reduced.

The assembly 100 may also include a number of wires 104 as described. The wires 104 may each be made of a highly elastic material or metal such as nitinol or surgical stainless steel. The wires 104 may include a sharpened distal tip used to pass the wires 104 a distance into a tissue such as bone. In an embodiment, the tissue may be pre-drilled prior to insertion of the wires 104 into the tissue to prevent the tissue from splitting as the wires 104 are passed into the tissue. In alternative embodiments, the tissue is not pre-drilled such that the wires 104 may be made relatively more permanent within the tissue such that the coefficient of friction produced between the tissue and the wires 104 is relatively higher.

As described herein, the wires 104 may be used to provide compression against the tissue as the wires 104 interface with the bone plate 102. The wires 104 provide this compression force by being biased towards each other as a result of being passed through the draw holes 144 formed through the draw plugs 110 or the bone plate 102. Because of this difference between the angle of the draw holes 144 (e.g., oblique angle through the obverse side 114 to the reverse side 116) and the angle of the wires 104, the wires 104, when embedded into the tissue, may cause the tissue to be compressed as the bone plate 102 is coupled to the wires 104.

Turning now to FIGS. 6-11, an exemplary process of installing the assembly 200 on a tissue 226 is described. At FIG. 6, an oblique view of a placement of a wire template 218 relative to a tissue 226 is shown. For ease of understanding, the tissue 226 may be described or referred to as a bone. However, it is understood that the assembly 200 may be used on any types of tissue and such examples are not meant to be limiting.

The installation process of the assembly 200 may include, in one embodiment, placing the template 218 at a location along the tissue 226. In the embodiment shown in FIG. 6, the template 218 is placed at a location along the tissue where a break, osteotomy, or other discontinuity has occurred. In this embodiment shown in FIG. 6, a reference paddle 224 may be placed within the break to arrange the template 218 at a location where the compression of the tissue 226 would close the break. In an alternative embodiment, the template 218 may not include a reference paddle 224 allowing for relatively more freedom of placement of the template relative to a joint or break in the tissue 226. In the embodiment shown in FIG. 6, however, the reference paddle 224 may be used as a reference geometry to appropriately place the wires at as set distance from the break. As such, the main body of the template 218 may be placed, in this embodiment, to traverse the break. In an embodiment, the width of the paddle 224 may be sized to create a specific gap between the two pieces of tissue 226.

The template 218 may be placed so that any number of wires 204 may be arranged at and inserted into the tissue 226. In some embodiments, the bone plate 202 may be situated such that at least one wire 204 is inserted into each side of the break. In some embodiments, the bone plate 202 may be situated such that both of the wires 204 are inserted into one side of the break or joint as long as the bone plate 202 is held firmly (e.g., via one or more fasteners or screws) to the tissue to provide the required counter torque to result in fusion-site compression. The placement of the template 218 may ensure that the placement of the wires 204 are set at a proper distance from the break or joint in order to avoid over compression or under compression during installation of the assembly 200 as described herein. In alternative embodiments, the assembly 200 may implement a single wire 204 or more than two wires 204 depending on the feature size of the draw plugs 210.

Figure 6:
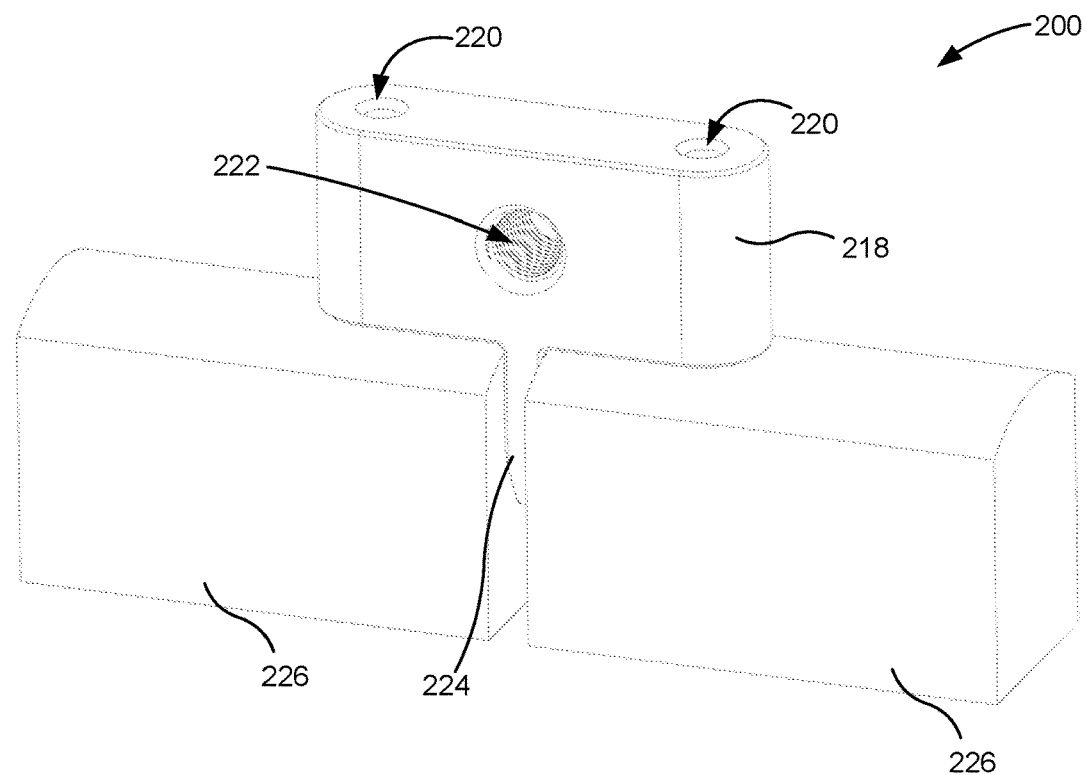
FIG. 6 is an oblique view of a placement of a wire template relative to a tissue.

In order to properly align the wires 204 at the locations along the surface of the tissue 226, the template 218 may include any number of guide holes 220. In an embodiment, the guide holes may be used to direct a drill or other device that may prepare the location of the wires 204 for insertion of those wires 204 into the tissue 226. Although the template 218 in FIG. 6 shows two guide holes 220, the present specification contemplates that any number of guide holes 220 may be used to insert any number of wires into one or both of the pieces of tissue 226. Additionally, the guide holes 220 may be non-parallel (e.g., divergent at distal ends of the guide holes 220) such that if a plate 202 with perpendicular draw holes 244 is placed over the wires 204, the moment created on the wires 204 results in compression.

In an embodiment, the template 218 may further include a stabilizing hole 222. The stabilizing hole 222 may be used by a clinician to stabilize the template 218 relative to the tissue 226 while the clinician places the wires 204 (and, in some embodiments, drills pilot holes) into the tissue 226 via the guide holes 220. In an embodiment, the stabilizing hole 222 may include threads that interface with any tool (e.g., a handle) that may be used to hold the template 218 while the wires 204 are placed and/or the predrill holes are drilled. As the template 218 is maintained against the tissue 226, a clinician may perform certain preparation work to prepare the tissue to receive wires 204 therein such as drilling holes at the guide holes 220 and/or placing a leg into the drilled holes.

Figure 7:
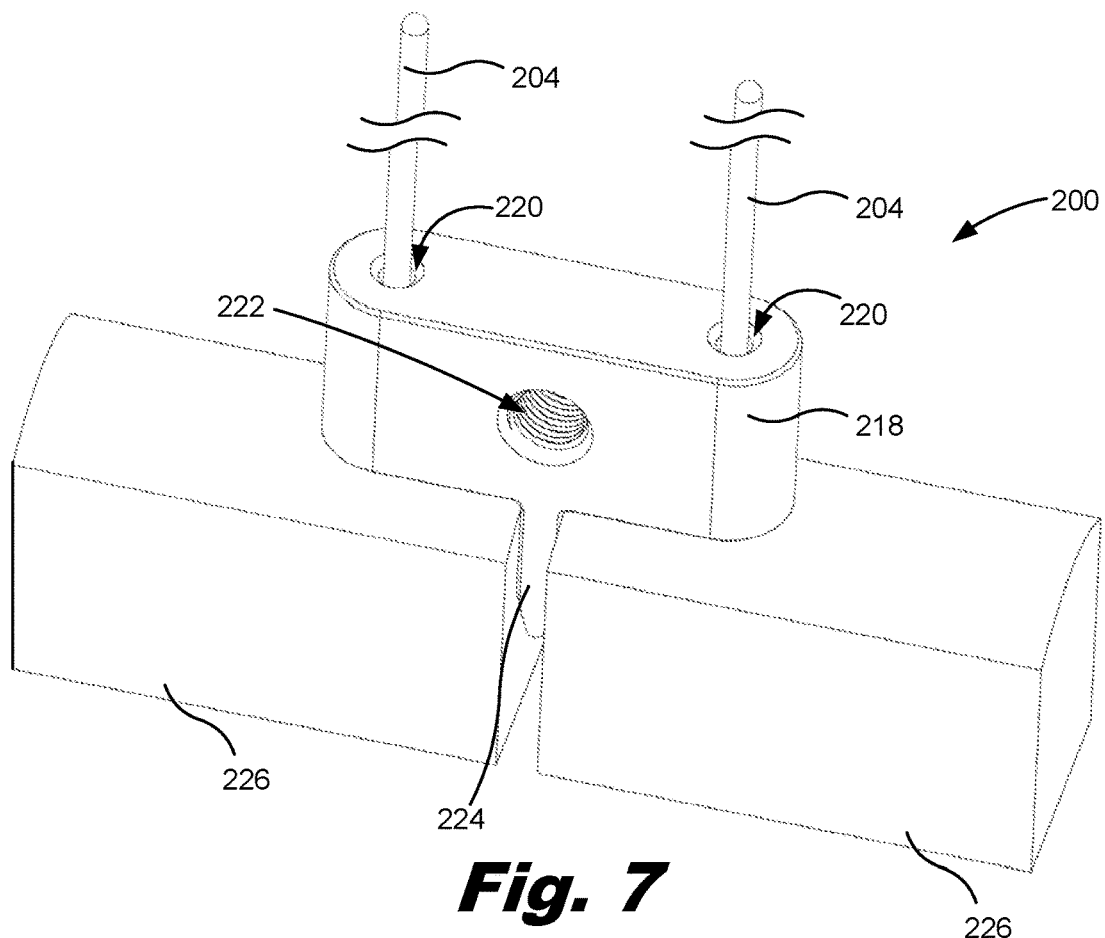
FIG. 7 is an oblique view of a placement of a wire template relative to a tissue with wires placed through the guide holes.

FIG. 7 is an oblique view of a placement of a wire template 218 relative to the tissue 226 with wires 204 placed through the guide holes 220. As described, in some embodiments, the guide holes 220 may have been used by the clinician to drill pilot holes within the tissue 226 to secure the wires 204 therein. In this embodiment, these pilot holes may have an internal diameter smaller than the internal diameter of the guide holes 220 and smaller in diameter than the wires 204. By making the pilot holes smaller than the diameter of the wires 204, placement of the wires 204 through the guide holes 220 and into the tissue 226 may not split the tissue while also allowing a certain level of friction between the tissue 226 and the wires 204. This may secure the wires 204 into the tissue 226 so that the wires are not easily removed from the tissue 226. In an embodiment, the pilot holes may be formed into the tissue relatively parallel to each other. In another embodiment, the pilot holes may be formed into the tissue oblique to each other. In either of these embodiments, the draw holes 244 used to draw the wires 204 therethrough may be at an angle different than that of the pilot holes within the tissue. In an embodiment, the guide holes 220 are formed through the template 218 so that a specific angle of the pilot hole is formed into the tissue. As described herein, prior to insertion of the wires 204 into the tissue 226, a leg (not shown) may be placed within the pilot holes drilled into the tissue 226. This leg may mate with the wire 204 and secure the wire into the tissue 226. In an embodiment, the leg may include retention features used to produce friction between the leg and the tissue.

The guide holes 220, in some embodiments described herein, are used to guide the placement of the wires 204 into the tissue 226. Again, in an embodiment, no pilot holes may be drilled and, instead, the wires 204 are forced into the tissue 226 thereby increasing the friction coefficient between the tissue 226 and the wires 204.

The wires 204 are shown as being relatively perpendicular to the tissue 226 in FIG. 7. However, similar tissue compression may be achieved by placing the wires 204 at divergent angles relative to the tissue 226 so that the distal tips are closer together than the proximal ends. Additionally, as will be discussed herein, the wires 204 may eventually be bent via one or more draw holes so that a compression force may be applied against the tissue 226 so as to close the break or joint in the tissue 226.

Figure 8:
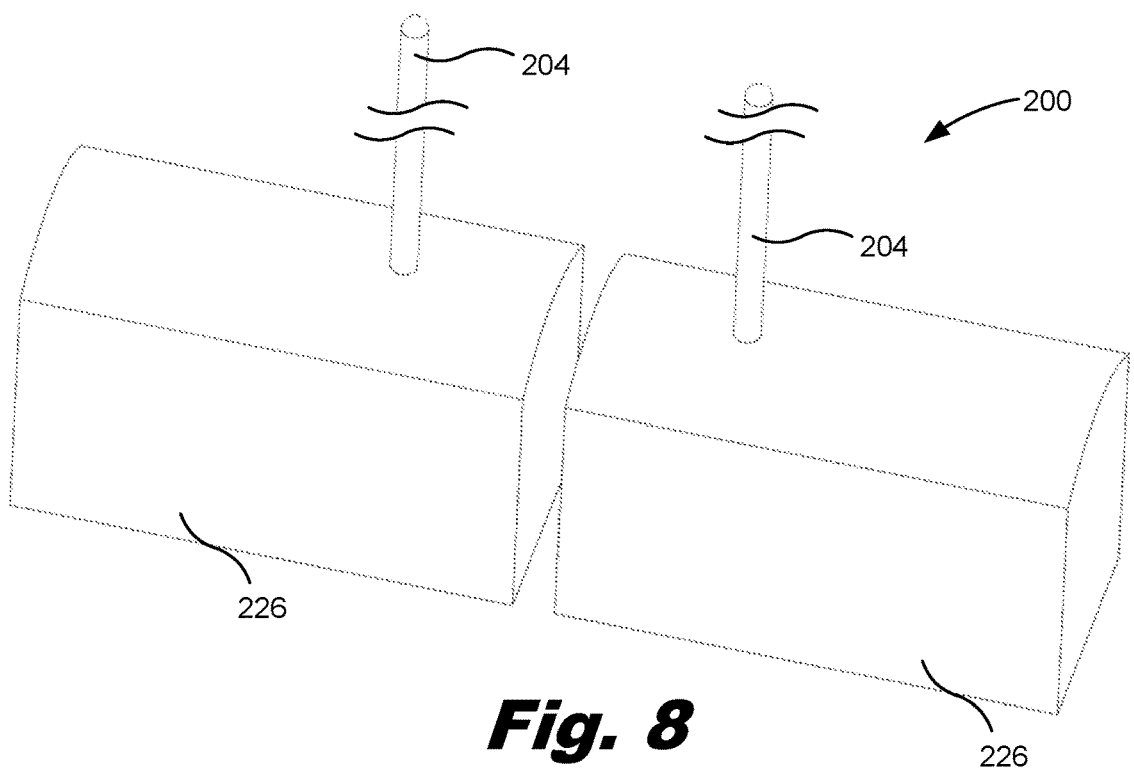
FIG. 8 is an oblique view of a placement of wires relative to a tissue.

FIG. 8 is an oblique view of a placement of wires 204 relative to a tissue 226. In FIG. 8 the template 218 shown in FIG. 7 has been removed from the wires 204. In an embodiment, the template 218 may be removed by sliding the template 218 upwards and away from the tissue 226 until the ends of the wires 204 are clear from the guide holes 220 formed through the template 218. As the template 218 is removed, the reference paddle 224 is also removed from in between the break in the tissue 226.

Figure 9:
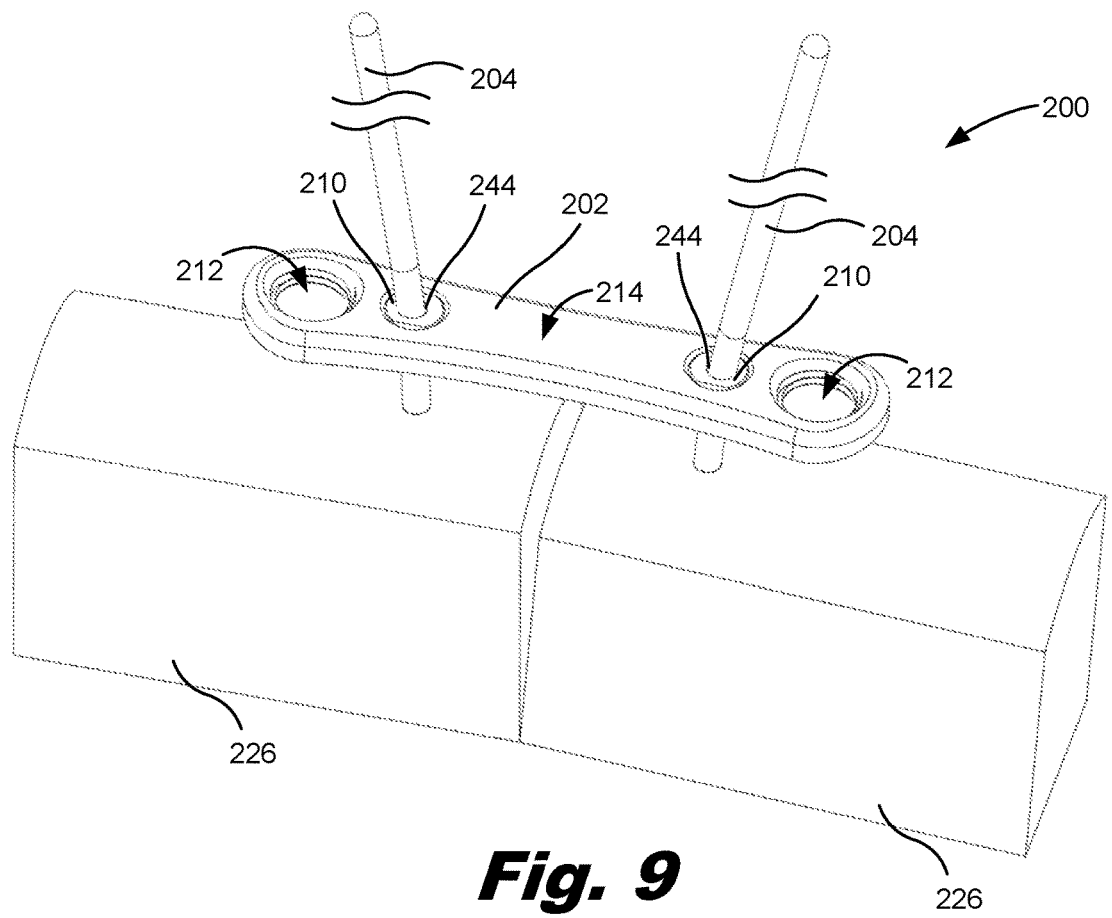
FIG. 9 is an oblique view of an installation of a bone plate relative to wires placed within a tissue.

FIG. 9 is an oblique view of an installation of a bone plate 202 relative to wires 204 placed within a tissue 226 from FIG. 8. As described herein, the installation of the bone plate 202 relative to the wires 204 includes passing a terminal and proximal end of each of the wires 204 through a draw hole 244. As described herein, in an embodiment the draw hole 244 may be formed through a draw plug 210. These draw plugs 210 may be inserted into a draw plug hole (e.g., similar to element 109 in FIG. 4) formed through the bone plate 202 from an obverse side 214 to a reverse side (e.g., similar to element 116 in FIG. 4). As the wires 204 are passed through their respective draw plugs 210 and the bone plate 202 is moved towards the surface of the tissue 226 in this embodiment, the wires may be distorted or bent due to the oblique draw holes 244 formed through those draw plugs 210.

In the specific example shown in FIG. 9, because the angle of the oblique draw holes 244 in the draw plugs 210 converge together at a reverse side of the bone plate 202, the proximal ends of the wires 204 are drawn apart. Concurrently, the distal ends of the wires 204 embedded into the tissue 226 may be drawn together causing the break in the tissue 226 to converge and a level of compression between the pieces of the tissue 226 to be realized. The level of compression placed between the pieces of the tissue 226 may be dependent on a number of factors including the oblique angle of the draw hole or holes formed in the draw plug 210 or draw plugs 210, the rigidity/elasticity of the wires 204, the distance of the draw plug holes 109 from each other, the distance between the draw plug holes 109 in the bone plate 202 relative to the distance between the guide holes 220 of the template 218, among other factors. Each of these features may be altered to achieve a specific compression at the break between the pieces of tissue 226 and the elements of the assembly 200 may be selected from a plurality of similar elements during the processes described herein in connection with FIGS. 6-11. Where beneficial to the care of the patient, the compression direction produced by the herein-described assembly 200, may be out of plane of with the plate 202 and may be either compressed towards/across a break or towards an adjacent tissue to correct a deformity, for example.

FIG. 9 shows the bone plate 202 at an intermediate location along the wires 204 such that the bone plate 202 is not in contact with the tissue 226. As the bone plate 202 is moved closer to the tissue 226, the force required to place the reverse side of the bone plate 202 against the tissue 226 may increase as the wire 204 is being bent in the oblique draw holes 244 formed through the draw plugs 210. Concurrently, compression of the pieces of the tissue 226 may also increase.

Figure 10:
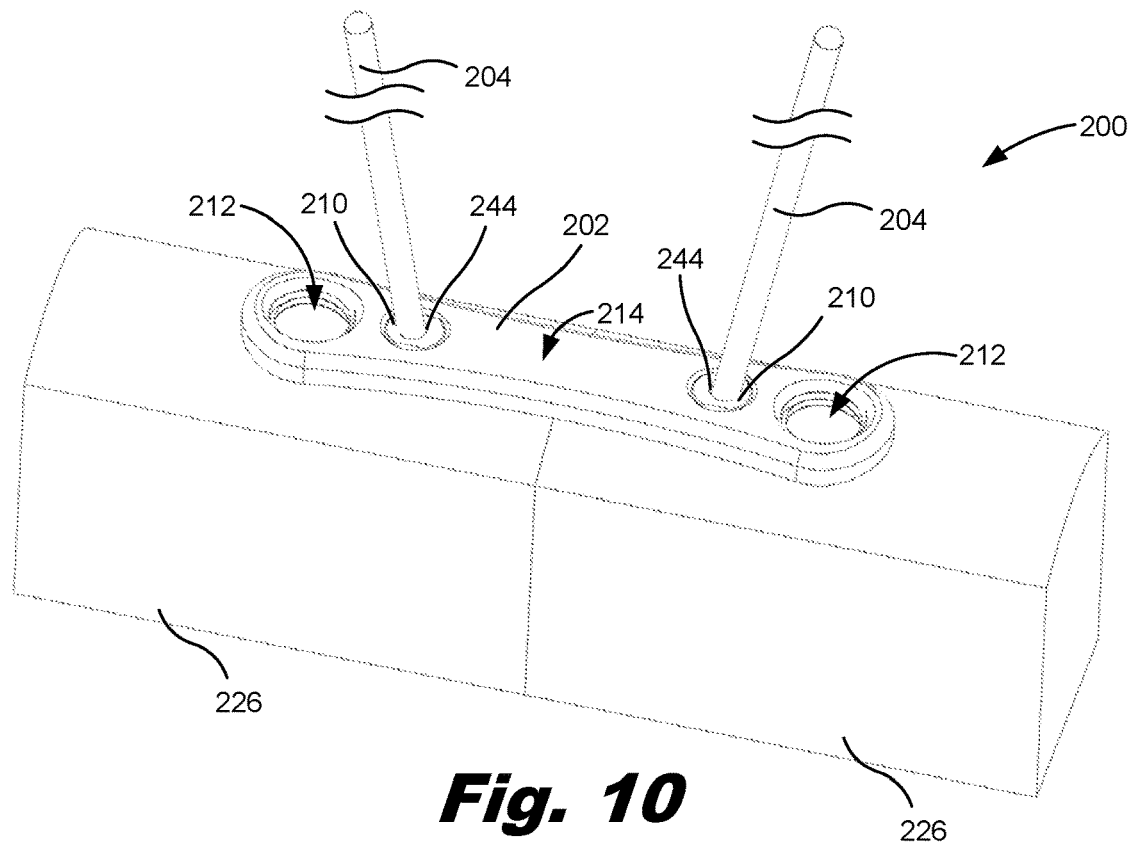
FIG. 10 is an oblique view of placement of a bone plate against a tissue and coupled to wires within a tissue.

FIG. 10 is an oblique view of placement of the bone plate 202 against the tissue 226 and coupled to the wires 204 within the tissue 226. FIG. 10 shows that the reverse side of the bone plate 202 has made contact with the surface of the tissue 226 thereby securing a final position of the wires 204 within the bone plate 202 and tissue 226. Additionally, as the reverse side of the bone plate 202 contacts the tissue 226, a maximum compression of the pieces of tissue 226 against each other is realized. FIG. 10 shows that this compression between pieces of tissue 226 causes the break in the tissue 226 to disappear and the bone plate 202 and wires 204 are now maintaining the position of the pieces of tissue 226.

FIG. 10 also shows that the clinician may now access the surface of the tissue 226 via the screw holes 212 formed from the obverse side 214 of the bone plate 202 to the reverse side (not shown) of the bone plate 202. At this point, a type of fastener such as a screw (not shown), staple, bone screw, or locking screw may be selected based on a number of factors. These factors may include the type of tissue 226 into which the screws are passed into, whether the screws are to be locking screws or not, the diameter of the screw holes 212, the screw drive to be used, among other factors. For ease of understanding, the description here may describe these fasteners as locking screws. However, the present specification contemplates that any type of fastener may be used to further secure the bone plate 202 to the tissue 226 as described herein.

Figure 11:
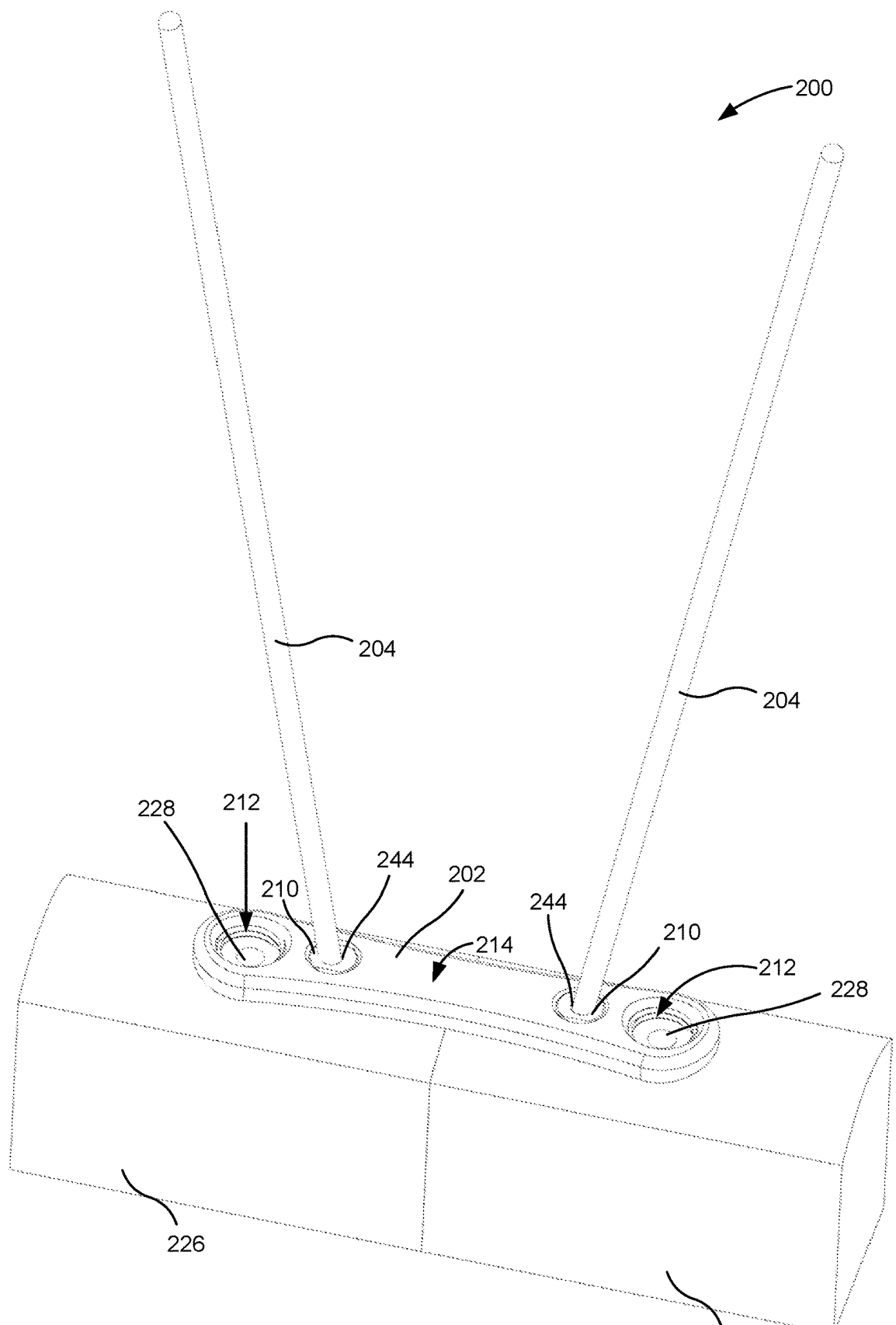
FIG. 11 is an oblique view of the formation of pilot holes into a tissue and with the bone plate against that tissue.

FIG. 11 is an oblique view of the formation of pilot holes 228 into the tissue 226 and placement of the bone plate 202 against that tissue 226. Similar to the pilot holes drilled for the wires 204 as described in connection with FIG. 6, the pilot holes 228 formed at the screw holes 212 may be used to allow the fasteners, staples, bone screws, or other types of screws to pass through the screw holes 212 and into the tissue 226. The pilot holes 228 may be drilled by a clinician so as to prevent any splitting of the tissue 226 as the screws are driven into the tissue 226. In a specific embodiment, the internal diameter of the pilot holes 228 may be smaller than the shaft diameter of the screws so that a level of friction may be realized between the internal surface of the pilot holes 228 and the outer surfaces of the screws used to secure the bone plate 202 to the tissue 226.

In an embodiment, a drill guide may be used to direct the direction and depth of the drill into the tissue 226 so as to accurately guide a drill to make the pilot holes 228 in the tissue 226. In this embodiment, the drill guide may be secured to the screw holes 212 via the threads formed in the screw holes 212 and complementary threads on the drill guide. The drill guide may also include a depth indicator and a viewable internal channel through which a drill bit may pass during formation of the pilot holes 228. By accurately securing the direction and depth of the pilot holes 228, a clinician may more accurately place the screws within the tissue 226 as described herein. After use, the drill guide may be removed for preparation of the screw holes 212 to receive the screws.

Figure 12:
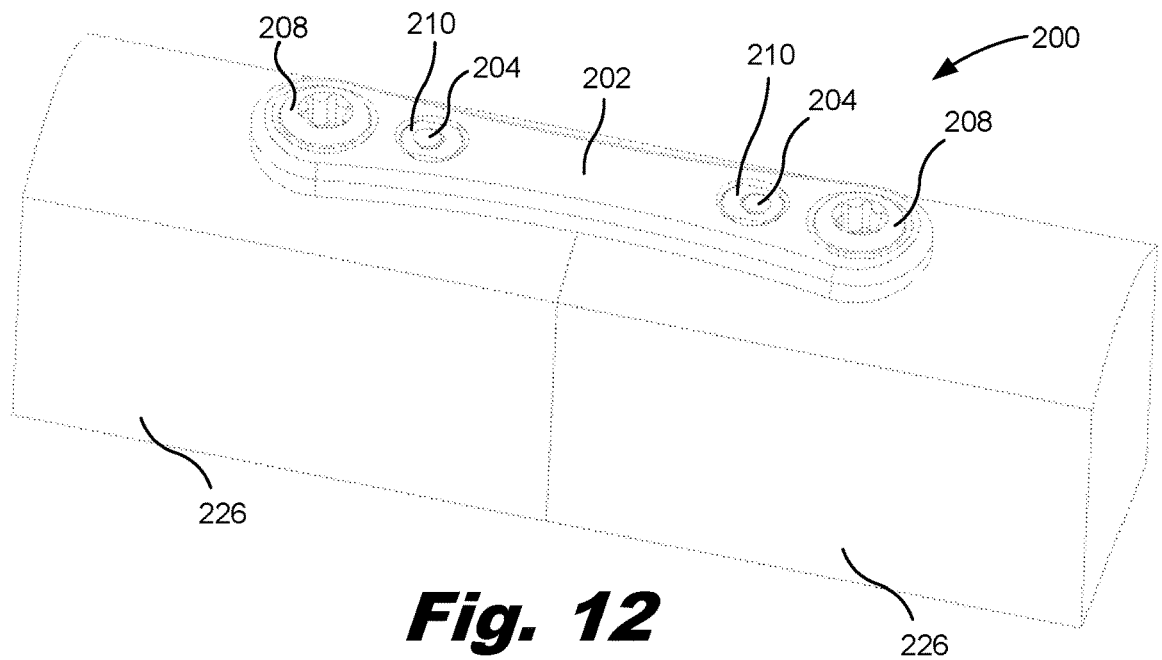
FIG. 12 is an oblique view of the placement of screws into a tissue and through a bone plate.

FIG. 12 is an oblique view of the placement of screws into a tissue 226 and through the bone plate 202. In FIG. 12, the screws are shown to have been seated into the pilot holes 228 descried in FIG. 11 with the screw heads 208 being sunk into the bone plate 202 as described herein. The securing of the screws into the bone plate 202 and tissue 226 provides additional and complementary stability of the bone plate 202 to the tissue 226 as that stability provided by the wires 204 as described herein. As described herein, the locking screw may include a first set of threads located at a proximal end of the locking screw below the screw heads 208. This first set of threads may interface with threads formed on the inside surface of the screw holes 212. A second set of threads formed along a shaft of the locking screw may interface with the tissue 226 in order to seat the locking screw into the tissue 226 and create friction between the fastener screw and the tissue 226.

FIG. 12 also shows that the wires 204 have been trimmed to be flush with a top surface of the draw plugs 210 so that the wires 204 do not protrude from the obverse side 214 of the bone plate 202. In an embodiment, a cutting tool may be used to trim the wires 204 flush with the top surface of the draw plugs 210. In another embodiment, a pair of wire or pin cutters may be used to trim the wires 204 flush with the top surface of the draw plugs 210. In an embodiment, a cam-screw cap or other anti-backout device may be used to cover the exposed end of the wires 204 thereby keeping the wires 204 from backing out of the bone plate 202 after being installed.

FIG. 12 shows, in an embodiment, a complete installation of the assembly 200 according to the processes described in connection with FIGS. 6-12. However, the process described in connection with FIGS. 6-12 of using the assembly 200 may include any combination of the processes described herein in any order to achieve that assembly 200 as shown in FIG. 12.

Figure 13:
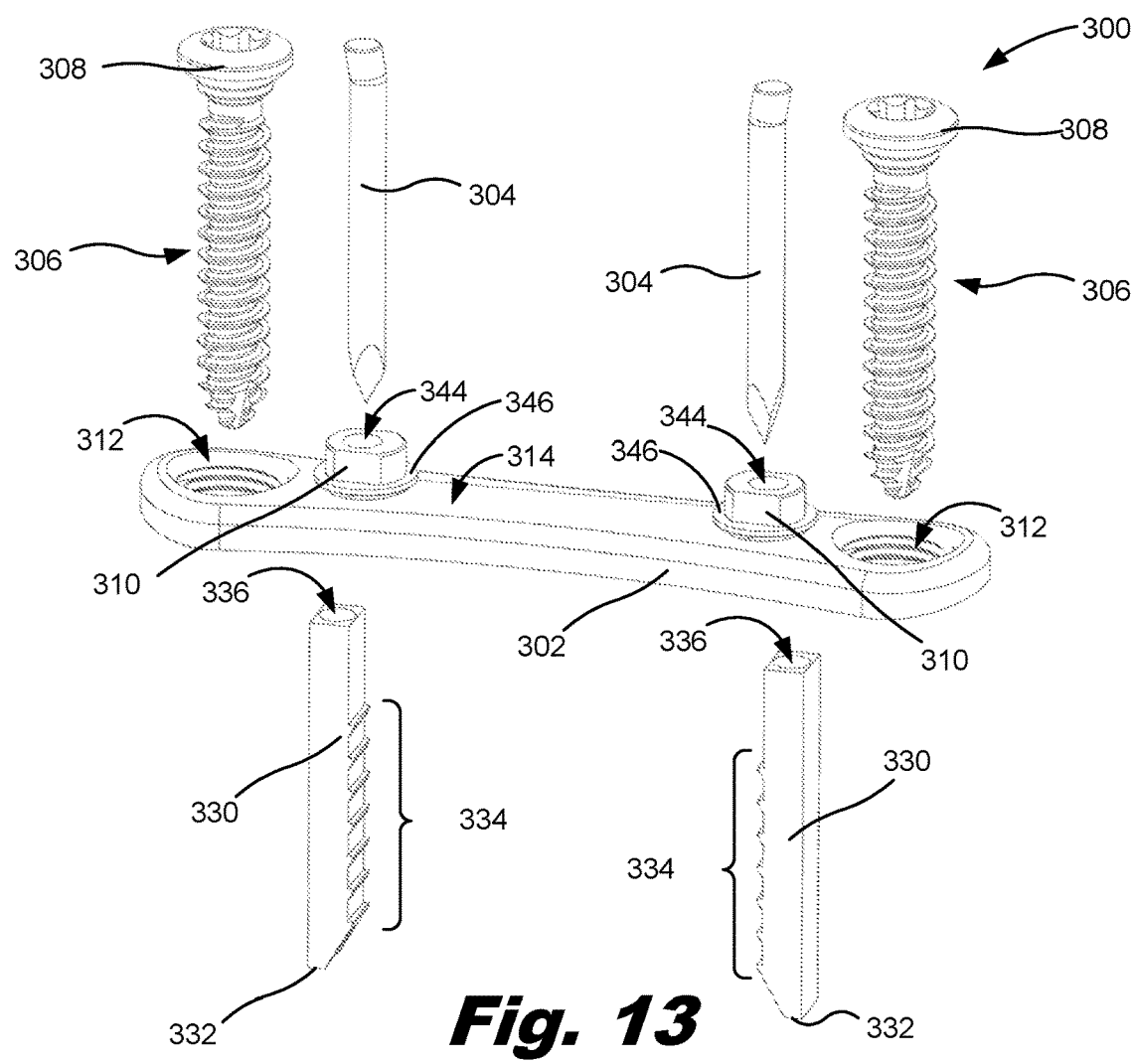
FIG. 13 is a top, oblique, exploded view of an assembly with a bone plate, wires, legs, and screws.
Figure 14:
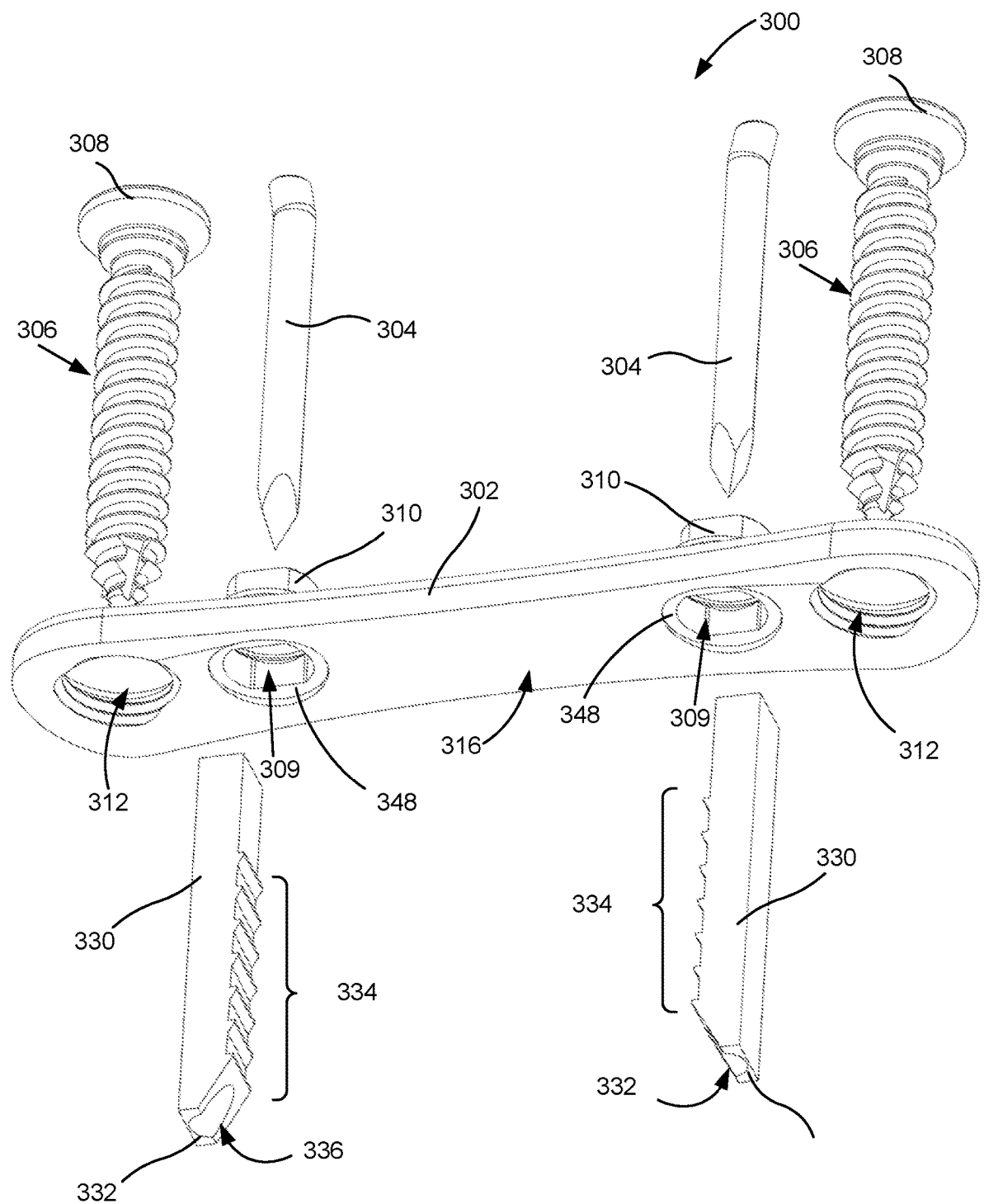
FIG. 14 is a bottom, oblique, exploded view of an assembly with a bone plate, wires, legs, and screws.

Now turning to FIGS. 13 and 14, another embodiment of an assembly 300 is shown to include, among other elements, a leg 330. FIG. 13 is a top, oblique, exploded view of an assembly 300 with a bone plate 302, wires 304, screws 306, and legs 330. The assembly 300 shown in FIG. 13 may be similar to that shown in FIGS. 1-4 with the inclusion of a leg 330.

In the assembly 300, the stabilizing member may be a bone plate 302, the dynamic element may be a wire 304 or a set of wires 304, and the fasteners may be screws 306. In an embodiment, the screws 306 of the assembly 300 may include locking screws or non-locking screws.

The bone plate 302 has an obverse side 314 and a reverse side 316. When the bone plate 302 is implanted or otherwise attached to a tissue (e.g., bone), the obverse side 314 faces away from the tissue portions and the reverse side 316 faces toward the tissue portions. The bone plate 304 may be made of a medical grade metal or plastic that allows for implantation into the human body. In an embodiment, the bone plate 302 may be made of a bendable material that is capable of deformation to fit across a portion of tissue within the human body. In a specific embodiment, the bone plate 302 may be deformed or bent to conform against a broken bone such as a foot bone within the human body.

The bone plate 302 may include several screw holes 312 which extend through the obverse side 314 and reverse side 316. Two screw holes 312 are illustrated in FIGS. 13 and 14, although any number of screw holes 312 may be present in the bone plate 302. In some embodiments, the size of the bone plate 302 may be sized to fit across any portion of tissue including any bone or cartilage within the human body. In these embodiments, the size of the bone plate 302 to be used on a femur bone may be relatively larger than a bone plate 302 used to be used on a bone within the foot such as a cuneiform bone.

In an embodiment, each screw hole 312 formed through the bone plate 302 may include an internally threaded portion and a nonthreaded portion so that each screw hole 312 accepts either one of a locking screw or a non-locking screw. In an embodiment, an internal threaded portion of the screw hole 312 may engage corresponding threads formed on the screw head 308 in order to serve as a locking screw system. In this embodiment, the screw 306 may be locked into the screw hole 312 when the screw 306 is fully seated into the screw hole 312. In an embodiment, the screw 306 is not a locking screw such that the bone plate 302 may be removed after, for example, the tissue has recuperated (e.g., bone has fused together).

In an embodiment, the screw 306 may include a screw head 308 with an exterior surface that fits within the screw hole 312 such that the screw head 308 at least partially sunk into the bone plate 302. The exterior surface may be convex, spherical, or conical. In an embodiment, the placement of the screw head 308 relative to the bone plate 302 may be such that the screw head 308 does not protrude beyond a top plane on the obverse side 314 of the bone plate 302. This may prevent tissues within the body from rubbing against the screw head 308 when a surgical incision has been made to access the surface of the tissue and upon closure of that surgical incision. In a specific embodiment, the screw 306 may have a 3.5 mm diameter and lengths from 8 mm to 30 mm in 2 mm increments. In an embodiment, the threads of the screw 306 formed below the screw head 308 may have a pitch and thread height sufficient to hold the bone plate 302 to the tissue when the screw 306 is fully sunk into the tissue. In an embodiment, the screw head 308 may include any type of screw drive that allows a clinician to interface a screwdriver with the screw drive in order to drive the screw 306 into the tissue.

The bone plate 302 of the assembly 300 may further include a number of draw plugs 310 formed into or placed within the body of the bone plate 302. In the embodiments shown in FIGS. 13 and 14, the draw plugs 310 are placed into draw plug holes 309 which extend through the obverse side 314 to the reverse side 316. As described herein, the bone plate 302 of the assembly 300 may further include one or more draw holes 344 through which a wire may be passed. In an embodiment, the draw hole 344 may be a hole formed from an obverse side 314 of the bone plate 302 to the reverse side 316 of the bone plate 302 as shown in, for example, in FIGS. 28 through 30. In another embodiment, the draw holes 344 may be formed through each of one or more draw plugs 310 as shown in the embodiment of FIGS. 13 and 14 (among other figures).

In an embodiment, draw plugs 310 may be formed into or placed within the body of the bone plate 302. In an embodiment, the draw plugs 310 may be coupled to the body of the bone plate 302. For example, where the draw plugs 310 are formed into the body of the bone plate 302, each draw plug 310 may be welded into or otherwise affixed within a draw plug hole 309 formed through the bone plate 302.

In an embodiment where the draw plugs 310 are insertable into the draw plug holes 309, the draw plug holes 309 formed through the bone plate 302 may have an interior surface that interfaces with an exterior surface of the draw plug 310 such that when the draw plug 310 is installed into the draw plug holes 309, the draw plug 310 is prevented from rotating within the draw plug holes 309. In the embodiments presented herein, the interior surfaces of each of the draw plug holes 309 and have any number of surfaces that create a fit (e.g., interference fit, clearance fit, transition fit among others) with the exterior surfaces of the draw plugs 310 to prevent the draw plug 310 from rotating within the draw plug holes 309. In an embodiment, the fit between the interior surface of the draw plug holes 309 and the exterior surface of the draw plugs 310 may include any non-circular cross-section shape. Hex, hexalobe, square, D-shaped, and other non-circular shapes are contemplated for the interior surfaces of the draw plug holes 309 and the exterior surfaces of the draw plugs 310.

In addition to the surfaces of the draw plug 310 that match with the interior surfaces of the draw plug holes 309, the draw plug 310 may include a lip 346 that interfaces with a recess 348 (e.g., a circular recess) formed on the bone plate 302 in some embodiments. The circular recess 348 in the embodiment shown in FIG. 14 may prevent the draw plug 310 from exiting the draw plug hole 309 and the bone plate 302 by interfacing the lip 346 with the circular recess 348 formed on the reverse side 316 of the bone plate 302. Consequently, when the assembly 300 is affixed to the tissue as described herein, the lip 346 may be sandwiched between the tissue and the reverse side 316 of the bone plate 302 and within the circular recess 348 so that the draw plug 310 is not removed from the assembly 300 when assembled.

The draw plugs 310 may include one or more draw holes 344 through which a wire 304 may be passed during assembly of the assembly 300 and coupling to the tissue as described herein. These draw holes 344 may be shown specifically in FIG. 13. The draw holes 344 formed through the draw plug 310 may be formed at an oblique angle. That is, the draw holes 344 formed through the draw plug 310 is not perpendicular to a top surface of the draw plug 310 such that the wire 304 is biased or bent when the bone plate 302 is coupled thereto. As described herein, the oblique angle of the draw holes 344 provides compression to be placed on neighboring pieces of tissue such that, during installation, the wires 304 cause the bone to be brought together. In these embodiments, the angles of the draw holes 344 in the draw plugs 310 may cause the individual wires 304 to be moved together such that as the wires 304 are inserted into the tissue, the tissue is compressed together. In an embodiment, the draw plug 310 may be made of polyether ether ketone (PEEK) so that as the wires 304 are passed through the 344 the friction between the draw plugs 310 and the wires 304 is reduced.

The assembly 300 may also include a number of wires 304 as described. The wires 304 may each be made of a highly elastic material or metal such as nitinol or surgical stainless steel. In some embodiments the wires 304 may be threaded to interface with any other threading device associated with the assembly 300, or the wires may be non-threaded. The wires 304 may also have any diameter sufficient to accomplish the function of the assembly 300 described herein. The wires 304 may include a sharpened distal tip used to pass the wires 304 a distance into a tissue such as bone. In an embodiment, the tissue may be pre-drilled prior to insertion of the wires 304 into the tissue to prevent the tissue from splitting as the wires 304 are passed into the tissue. As described herein, the wires 304 may be used to provide compression against the tissue as the wires 304 interface with the bone plate 302. The wires 304 provide this compression by being biased towards each other as a result of being passed through the draw holes 344 formed through the draw plugs 310. Because of this oblique angle of the draw holes 344, the wires 304, when embedded into the tissue, may cause the tissue to be compressed as the bone plate 302 is coupled to the wires 304.

The assembly 300 may also include a leg 330. The leg 330 may be a reinforcement element that, in some embodiments, prevents the wires 304 from forcing their way through poor quality cancellous tissue (e.g., bone) when the tissue is being compressed as described herein. The leg 330 accomplishes this reinforcement purpose by distributing the compressive forces produced by the assembly 300 over a greater surface area.

In an embodiment, the leg 330 includes an insertion tip 332 at a distal end of the leg 330 that is made to initiate insertion into a tissue. The insertion tip 332 may be sharpened or otherwise pointed to provide for easier insertion into the tissue as the assembly 300 is coupled to the tissue as described herein. In an embodiment, the leg 330 may be inserted into a pilot hole drilled by a template such as that described in connection with FIG. 7.

In an embodiment, the leg 330 may also include retention features 334. In an embodiment, the retention feature 334 may be formed on one or more sides of the leg 330. In an embodiment, the retention features may protrude outward from a longitudinal axis of the leg 330. The retention features 334 may increase the friction between the tissue and the leg 330. An increase in friction may prevent removal of the leg 330 while also distributing the compressive forces over a greater surface area on the tissue. In an embodiment, the retention features 334 may be in the form of a plurality of saw-toothed shaped bumps on the surface of the leg 330. These saw-toothed-shaped bumps may bias for the insertion of the leg 330 while preventing the removal of the leg 330 from the tissue.

In an embodiment, the leg 330 may include a wire channel 336 formed through a longitudinal axis of the leg 330 from a proximal end of the leg 330 to the distal end of the leg 330. In a specific embodiment, the wire channel 336 may be threaded to interface with, for example a threaded portion of the wires 304 as described herein. In other embodiments, any mechanical connection or locking feature may be formed at the leg 330 such as a spring feature, an elastic or plastic deformation, or a keyway, among others, that interfaces the leg 330 with the wire 304 that resists migration of the leg relative to the wire 304. The wire channel 336 may receive the wire 304 therethrough during assembly so that the compressive forces produced by the assembly 300 are distributed over a greater surface area of the tissue. In an embodiment, the leg 330 may be placed deeper in the tissue than the wires 304 to allow the wires 304 to move within the leg 330 and apply the forces to the interior surface of the leg 330 as described herein. In an embodiment, the leg 330 may be placed within the tissue at a location shallower than the distal end of the wire 304. In this embodiment, the wire 304 may place the compressive forces against the tissue as well as on the interior surface of the wire channel 336 of the leg 330.

Turning now to FIGS. 15-20, an exemplary process of installing the assembly 400 on a tissue 426 is described. In an embodiment, the process for installing the assembly 400 described herein may be similar to the process described in connection with FIGS. 6 and 7. Here, a tissue 426 may be exposed via, for example, an incision by a clinician. In this embodiment, the installation process of the assembly 400 may include placing a template (not shown) at a location along the tissue 426 in a manner similar to, or identical to, that shown in FIGS. 6 and 7. The template is placed at a location along the tissue where, for example, a break has occurred. A reference paddle may be placed within the break to arrange the template at a location where the compression of the tissue 426 would close the break. As such, the template may be placed, in an embodiment, to traverse the break. The template may be placed so that that a number of wires 404 may be arranged at and inserted into the tissue 426. In some embodiments, the bone plate 402 may be situated such that both of the wires 404 are inserted into one side of the break or joint as long as the bone plate 402 is held firmly to the tissue to provide the required counter torque to result in fusion-site compression. In an embodiment, the processes and methods may include a single wire 404 that secures the bone plate 402 to a first portion of the tissue 426 while a fastener such as a screw or locking screw is used to secure the bone plate 402 to a second portion of the tissue 426. For ease of understanding, however, the methods and processes described in connection with FIGS. 15-20 are described as having a wire 404 and a fastener (e.g., screw 408) used to secure the bone plate 402 to the first portion of the tissue 426 as well as a wire 404 and fastener (e.g., screw 408) used to secure the bone plate 402 to the second portion of the tissue 426.

In another embodiment, the process and method may include the insertion of a plurality of wires into the tissue without the use of any fasteners to secure the bone plate 402 to the tissue 426. In this embodiment, the template may be used to form pilot holes 424 into the tissue 426. As described herein, these wires may be passed through a number of draw holes (either formed in the bone plate 402 or through a draw plug) and the bone plate 402 may be forced towards the tissue 426. As the bone plate 402 is forced towards the tissue 426, the wires 404 may be bent causing the tissue 426 to be compressed. In this embodiment, the forces associated with this compression may cause the bone plate 402 to be secured to the tissue 426 without the use of a fastener.

In order to properly align the wires 404 at the locations along the surface of the tissue 426, the template may include any number of guide holes. The guide holes may be used to direct a drill or other device that may prepare the location of the wires 404 for insertion of those wires 404 into the tissue 426.

Figure 15:
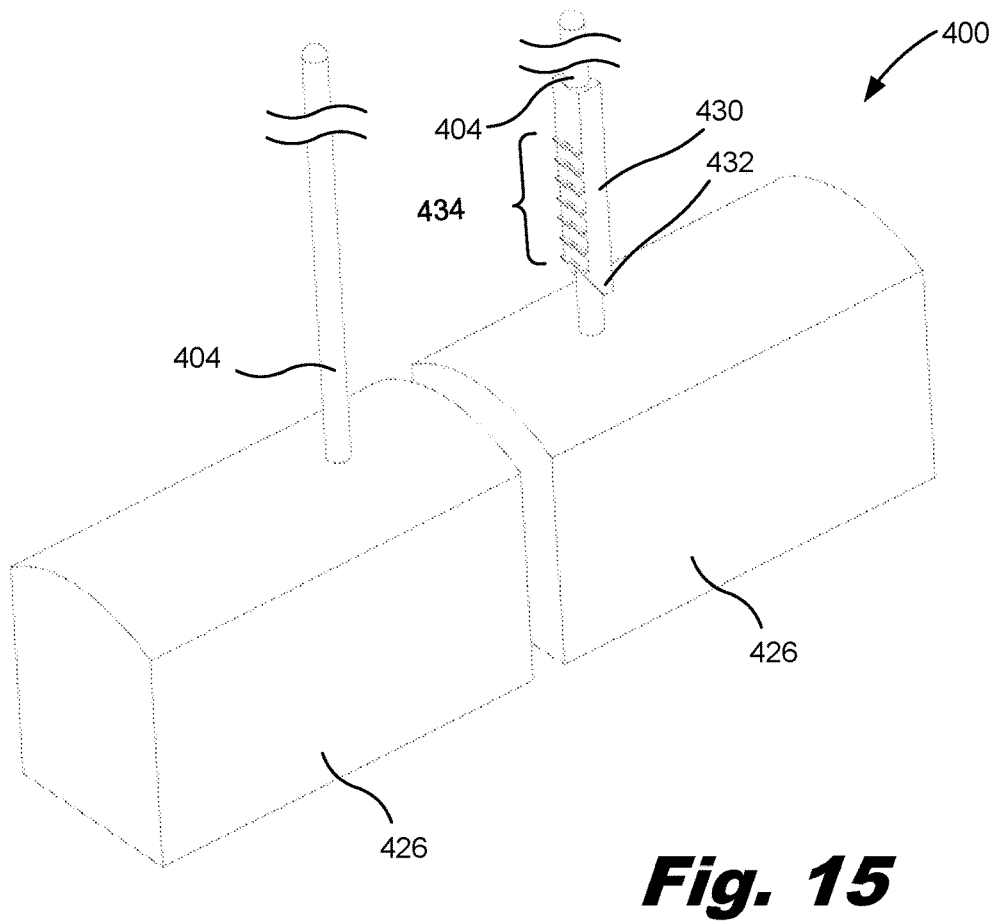
FIG. 15 is an oblique view of a placement of wires and a leg relative to a tissue.

In an embodiment and prior to the orientation shown in FIG. 15, the clinician may utilize a stabilizing hole formed into the template. The stabilizing hole may be used by a clinician to stabilize the template relative to the tissue 426 while the clinician drills pilot holes 424 into the tissue 426 via the guide holes. In an embodiment, the stabilizing hole may include threads that interface with any tool that may be used to secure the template to the tissue 426 such as a clamp. As the template is maintained against the tissue 426, a clinician may perform certain preparation work to prepare the tissue to receive wires 404 therein such as drilling holes at the guide holes.

As described, the guide holes may have been used by the clinician to drill pilot holes 424 within the tissue 426 to secure the wires 404 therein. In an embodiment, these pilot holes 424 may have an internal diameter smaller than the internal diameter of the guide holes and smaller in diameter of the wires 404. By making the pilot holes 424 smaller than the diameter of the wires 404 and legs 430, placement of the wires 404 and legs 430 through the guide holes and into the tissue 426 may not split the tissue while also allowing a certain level of friction between the tissue 426 and the wires 404 and/or legs 430. This may secure the wires 404 into the tissue 426 and/or legs 430 so that the wires are not easily removed from the tissue 426. In an embodiment, the legs 430 may also each include an insertion tip 432 at a distal end of the leg 430 that is made to initiate insertion into a tissue. The insertion tip 432 may be sharpened or otherwise pointed to provide for easier insertion into the tissue as the assembly 400 is coupled to the tissue as described herein.

In an embodiment, the leg 430 may also include retention features 434. In an embodiment, the retention feature 434 may be formed on one or more sides of the leg 430. In an embodiment, the retention features may protrude outward from a longitudinal axis of the leg 430. The retention features 434 may increase the friction between the tissue and the leg 430.

At FIG. 15 the proximal end of the wire 404 is passed into the distal end of the leg 430 after the wires 404 had been implanted into the tissue 426 as described herein. Although FIG. 15 shows a single leg 430 being passed over a single wire 404, the present specification contemplates that a leg 430 may be matched with any of the wires 404 implanted into the tissue 426. In an embodiment, the pilot holes 424 drilled into the tissue 426 for the wires 404 may be sized to also fit the leg 430 therein so that the tissue 426 will not split when both the wire 404 and leg 430 are driven into the tissue 426. In an alternative embodiment, the pilot holes 424 may be drilled and the legs 430 may initially be passed into those pilot holes 424. In this embodiment, the leg 430 may include any threaded portion or retention feature that receives a distal end of the wires 404 into the wire channel (e.g., element 336, FIG. 14) and retains the wires 404 therein.

Figure 16:
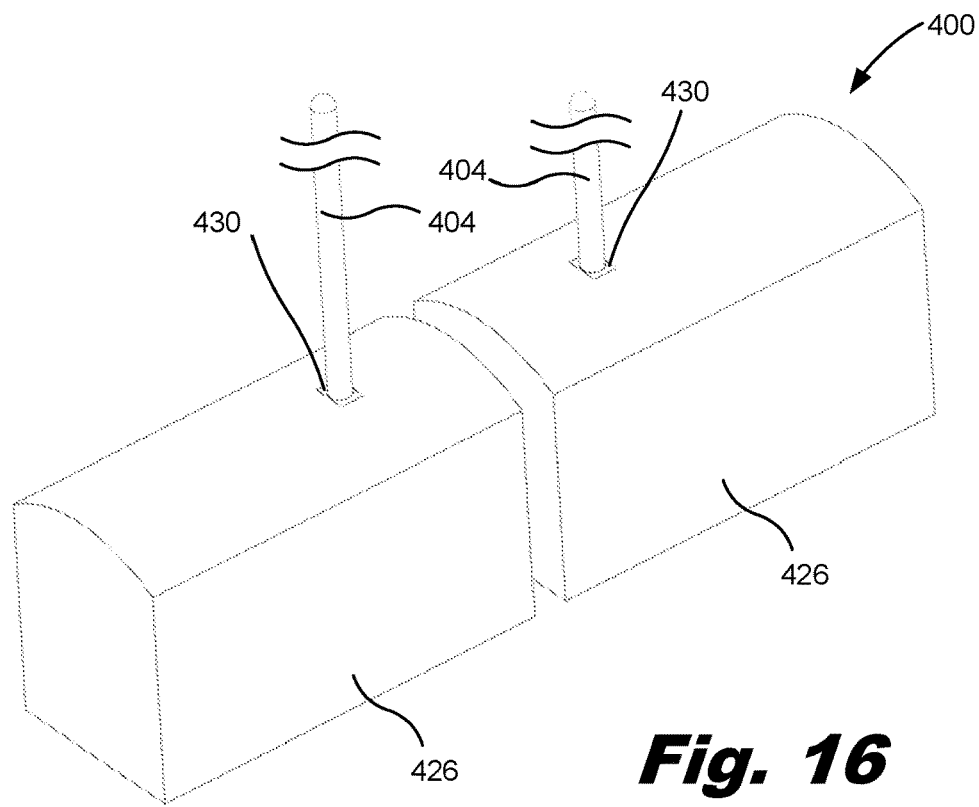
FIG. 16 is an oblique view of a placement of wires and a leg relative to a tissue.

FIG. 16 is an oblique view of a placement of wires 404 and the leg 430 relative to a tissue 426. FIG. 16 shows two leg 430 and wire 404 sets have been seated into the tissue 426. Again, the leg 430 may be a reinforcement element that, in some embodiments, prevents the wires 404 from forcing their way through poor quality cancellous tissue (e.g., bone) when the tissue is being compressed as described herein. The leg 430 accomplishes this reinforcement purpose by distributing the compressive forces produced by the assembly 400 over a greater surface area. In an embodiment, the leg 430 includes an insertion tip (not shown) that is made to initiate insertion into a tissue allowing for it being seated into the tissue 426. The insertion tip may be sharpened or otherwise pointed to provide for easier insertion and seating into the tissue as the assembly 400 is coupled to the tissue as described herein.

Figure 17:
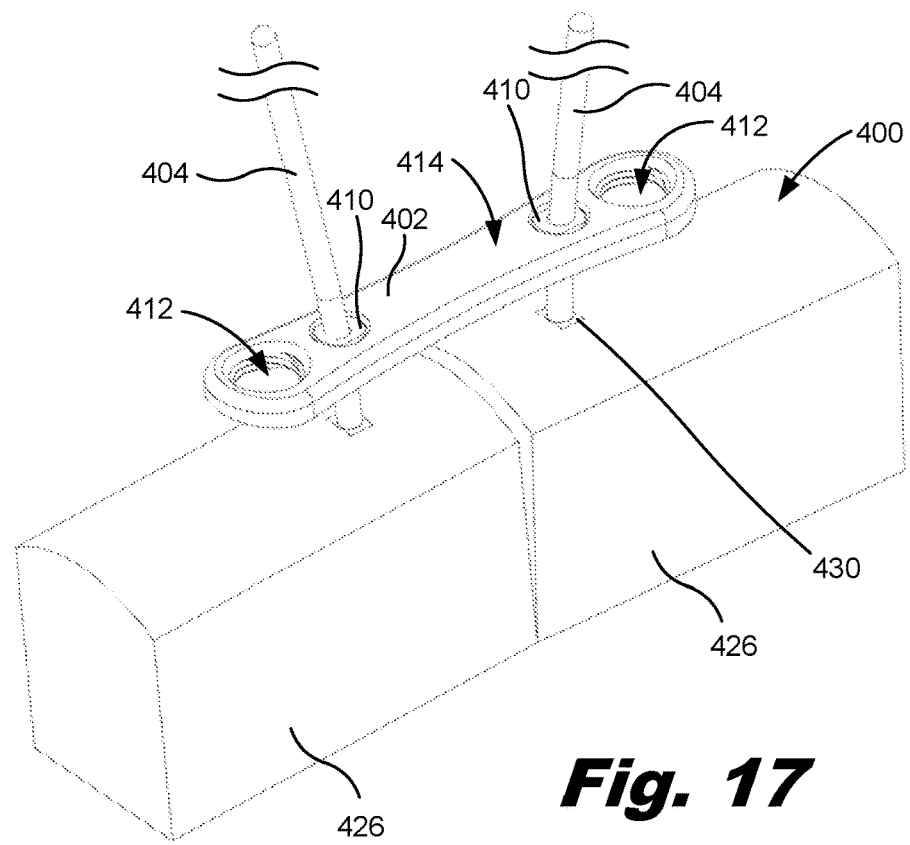
FIG. 17 is an oblique view of an installation of a bone plate relative to wires placed within a tissue.

FIG. 17 is an oblique view of an installation of a bone plate 402 relative to wires 404 placed within the tissue 426 is shown. As described herein, the installation of the bone plate 402 relative to the wires 404 includes passing a terminal and proximal end of each of the wires 404 through a draw hole formed in a draw plug 410. As the wires 404 are passed through their respective draw plugs 410, the wires may be distorted due to the oblique draw hole formed through the draw plugs 410.

In the example shown in FIG. 17, because the angle of the oblique draw holes in the draw plugs 410 converge together at a reverse side of the bone plate 402, the proximal ends of the wires 404 are drawn apart. Concurrently, the distal ends of the wires 404 embedded into the tissue 426 may be drawn together causing the break in the tissue 426 to converge and a level of compression between the pieces of the tissue 426 to be realized. The level of compression placed between the pieces of the tissue 426 may be dependent on a number of factors including the oblique angle of the draw hole or holes formed in the draw plug 410 or draw plugs 410, the distance between the draw plug holes in the bone plate 402 relative to the distance between the guide holes of the template, the rigidity/elasticity of the wires 404, the distance of the draw plug holes from each other, among other factors. The draw plugs 410 may be inserted into the draw plug holes in multiple orientations to generate compression/wire force in different directions relative to the bone plate 402. Each of these features may be altered to achieve a specific compression at the break between the pieces of tissue 426 and the elements of the assembly 400 may be selected from a plurality of similar elements during the processes described herein in connection with FIGS. 15-20.

FIG. 17 shows the bone plate 402 at an intermediate location along the wires 404 such that the bone plate 402 is not in contact with the tissue 426. As the bone plate 402 is moved closer to the tissue 426, the force required to place the reverse side of the bone plate 402 against the tissue 426 may increase as the wire 404 is being bent in the oblique draw holes in the draw plugs 410 and compression of the pieces of the tissue 426 increases.

Figure 18:
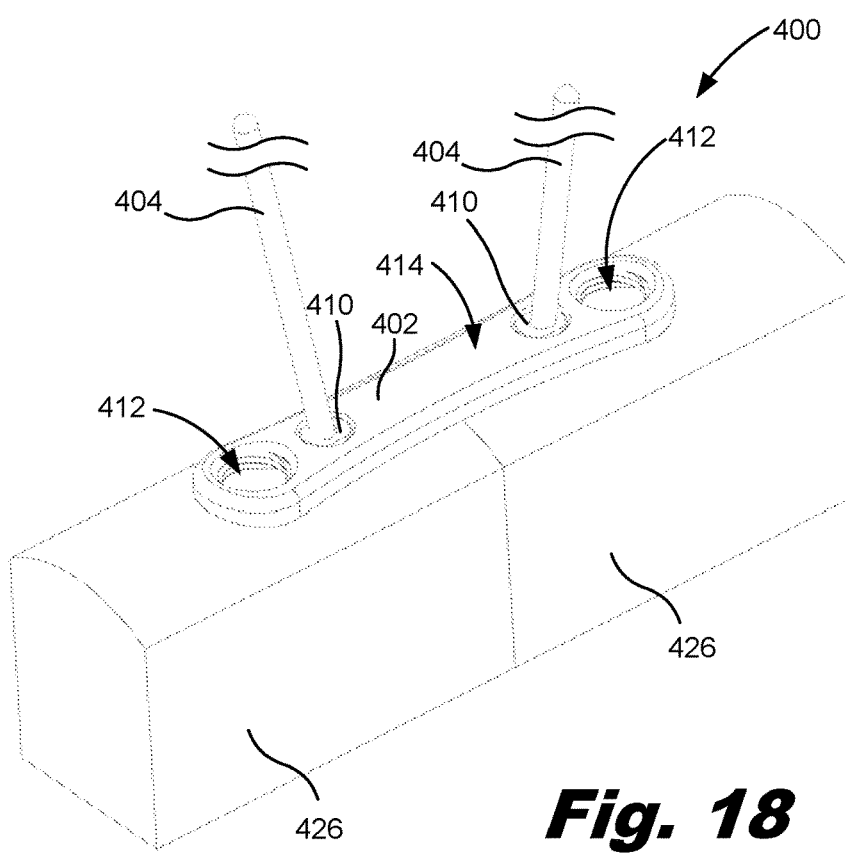
FIG. 18 is an oblique view of placement of a bone plate against a tissue and coupled to wires within a tissue.

FIG. 18 is an oblique view of placement of a bone plate 402 against a tissue 426 and coupled to wires 404 within the tissue 426. FIG. 18 shows that the reverse side of the bone plate 402 has made contact with the surface of the tissue 426 thereby securing a final position of the wires 404 within the bone plate 402 and tissue 426. Additionally, as the reverse side of the bone plate 402 contacts the bone plate 402, a maximum compression of the pieces of tissue 426 against each other accomplishable by the bone plate 402 and assembly 400 is realized. FIG. 18 shows that this compression between pieces of tissue 426 causes the break in the tissue 426 to disappear and the bone plate 402 and wires 404 are now maintaining the position of the pieces of tissue 426.

FIG. 18 also shows that the clinician may now access the surface of the tissue 426 via the screw holes 412 formed from the obverse side 414 of the bone plate 402 to the reverse side (not shown) of the bone plate 402. At this point, a type of screw (not shown) may be selected based on a number of factors. These factors may include the type of tissue 426 into which the screws are passed into, whether the screws are to be locking screws or not, the diameter of the screw holes 412, the screw drive to be used, among other factors.

Figure 19:
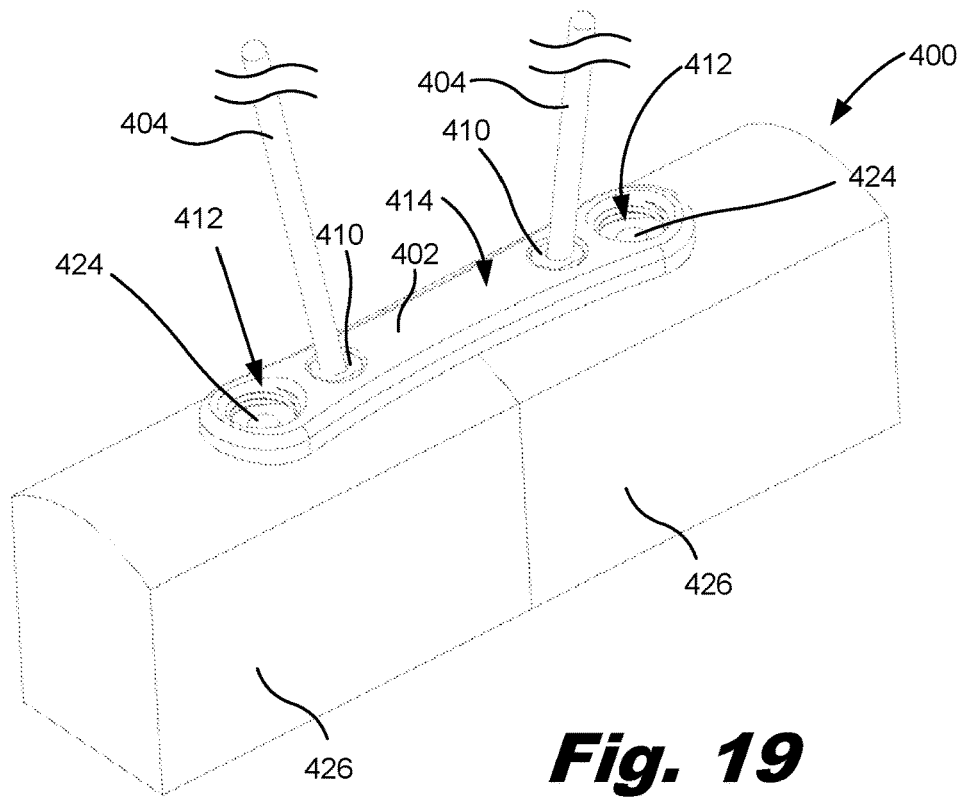
FIG. 19 is an oblique view of the formation of holes into a tissue and placement of a plate against that tissue.

FIG. 19 is an oblique view of the formation of pilot holes 424 into the tissue 426 and placement of the bone plate 402 against that tissue 426. Similar to the pilot hole 424 drilled for the wires 404, the pilot holes 424 formed at the screw holes 412 may be used to allow the screws to pass through the screw holes 412 and into the tissue 426. The pilot holes 424 may be drilled by a clinician so as to prevent any splitting of the tissue 426 as the screws are driven into the tissue 426. In a specific embodiment, the internal diameter of the pilot hole 424 may be smaller than the shaft diameter of the screws so that a level of friction may be realized between the internal surface of the pilot holes 424 and the outer surfaces of the screws used to secure the bone plate 402 to the tissue 426.

In an embodiment, a drill guide may be used to direct the direction and depth of the drill into the tissue 426 so as to accurately guide a drill to make the pilot holes 424 in the tissue 426. In this embodiment, the drill guide may be secured to the screw holes 412 via the threads formed in the screw holes 412 and complementary threads formed on the screw guide. The screw guide may also include a depth indicator and a viewable internal channel through which a drill bit may pass during formation of the pilot holes 424. By accurately securing the direction and depth of the pilot holes 424, a clinician may more accurately place the screws within the tissue 426 as described herein. After use, the drill guide may be removed for preparation of the screw holes 412 to receive the screws.

Figure 20:
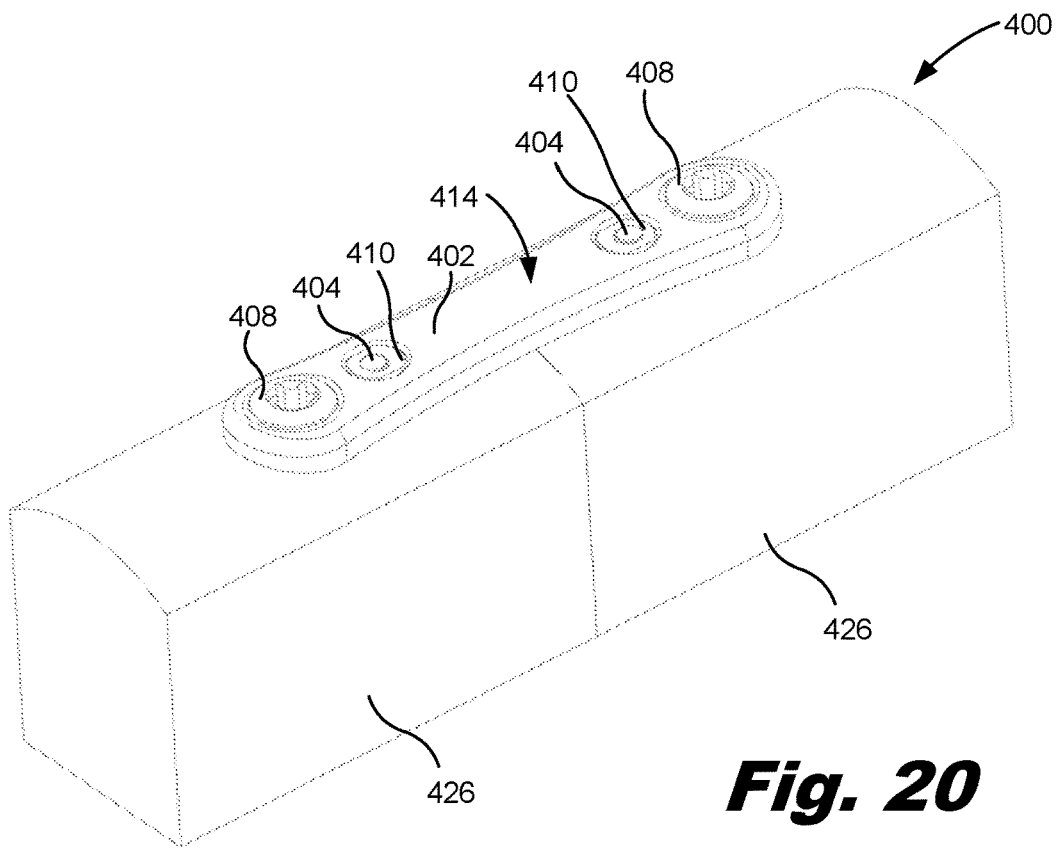
FIG. 20 is an oblique view of the placement of screws into a tissue and through a bone plate.

FIG. 20 is an oblique view of the placement of screws into a tissue 426 and through the bone plate 402. In FIG. 20, the screws 408 are shown to have been seated into the pilot holes 424 with the heads of the screws 408 being sunk into the bone plate 402 as described herein. The securing of the screws 408 into the bone plate 402 and tissue 426 provides additional and complementary stability of the bone plate 402 to the tissue 426 as that stability provided by the wires 404 as described herein.

FIG. 20 also shows that the wires 404 have been trimmed to be flush with a top surface of the draw plugs 410 so that the wires 404 do not protrude from the obverse side 414 of the bone plate 402. In an embodiment, a saw may be used to trim the wires 404 flush with the top surface of the draw plugs 410. In another embodiment, a pair of snips may be used to trim the wires 404 flush with the top surface of the draw plugs 410.

FIG. 20 shows, in an embodiment, a complete installation of the assembly 400 according to the processes described in connection with FIGS. 15-20. However, the process described in connection with FIGS. 15-20 of using the assembly 400 may include any combination of the processes described herein in any order to achieve that assembly 400 as shown in FIG. 20. The present specification further contemplates that the processes and methods described in connection with FIGS. 6-12 as described herein may also be used in conjunction with the processes described in connection with FIGS. 15-20 based on the medical needs of any given patient. For example, a leg 430 may be used to secure one wire 404 into a first portion of the tissue 426 while a second portion of the tissue 426 does not include the installation of a leg 430. This may be due to the location and differing conditions of the tissue 426 at these two portions of the tissue 426.

Figure 21:
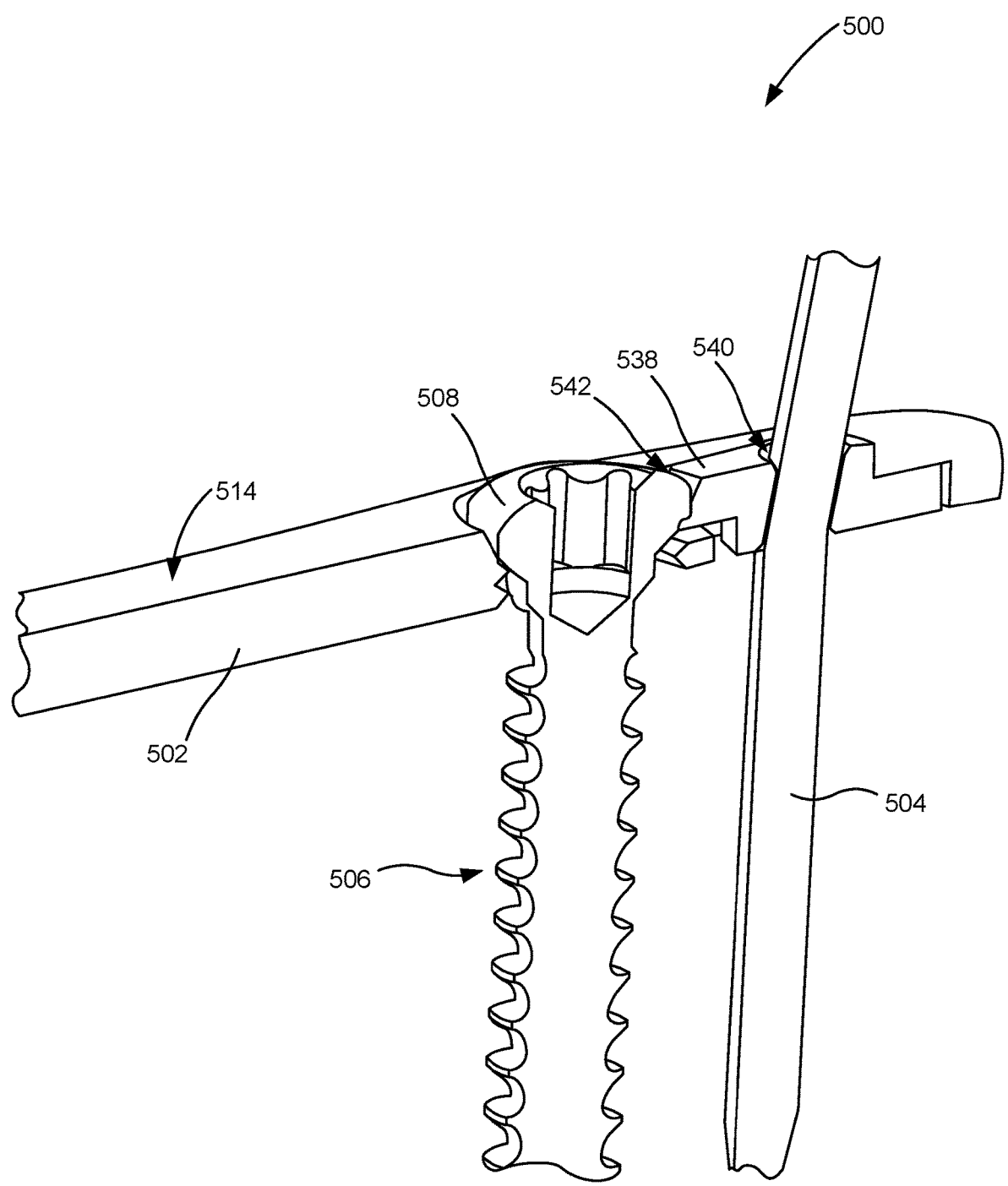
FIG. 21 is a longitudinal cross-section of an assembly with a bone plate, wires, slide, and screws.
Figure 22:
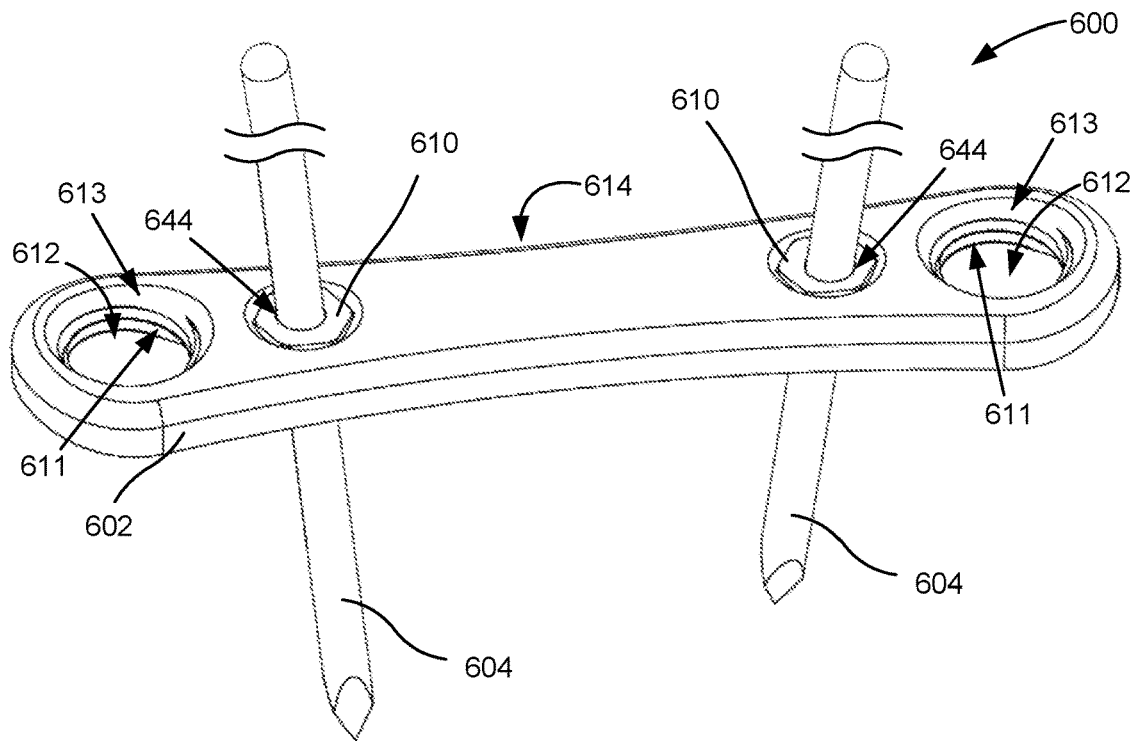
FIG. 22 is a top, oblique view of an assembly with a bone plate, draw plugs, and wires.
Figure 23:
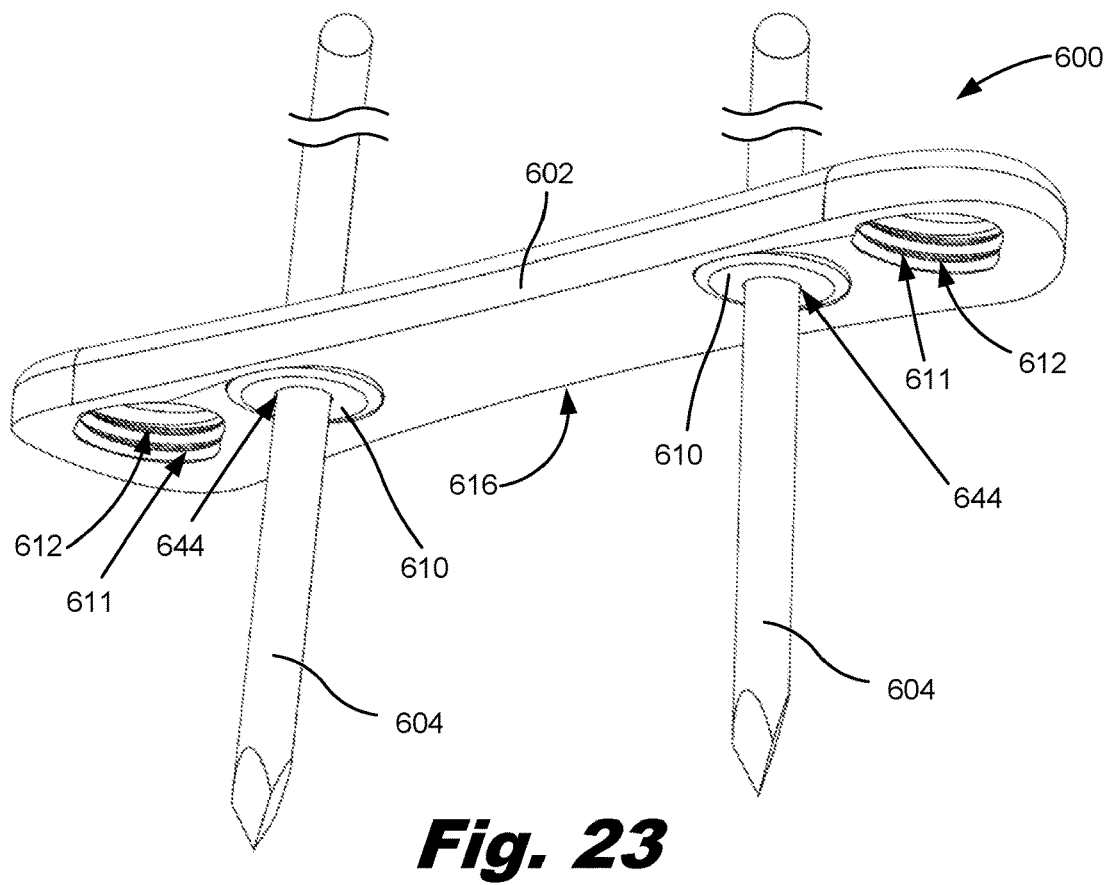
FIG. 23 is a bottom, oblique view of an assembly with a bone plate, draw plugs, and wires.
Figure 24:
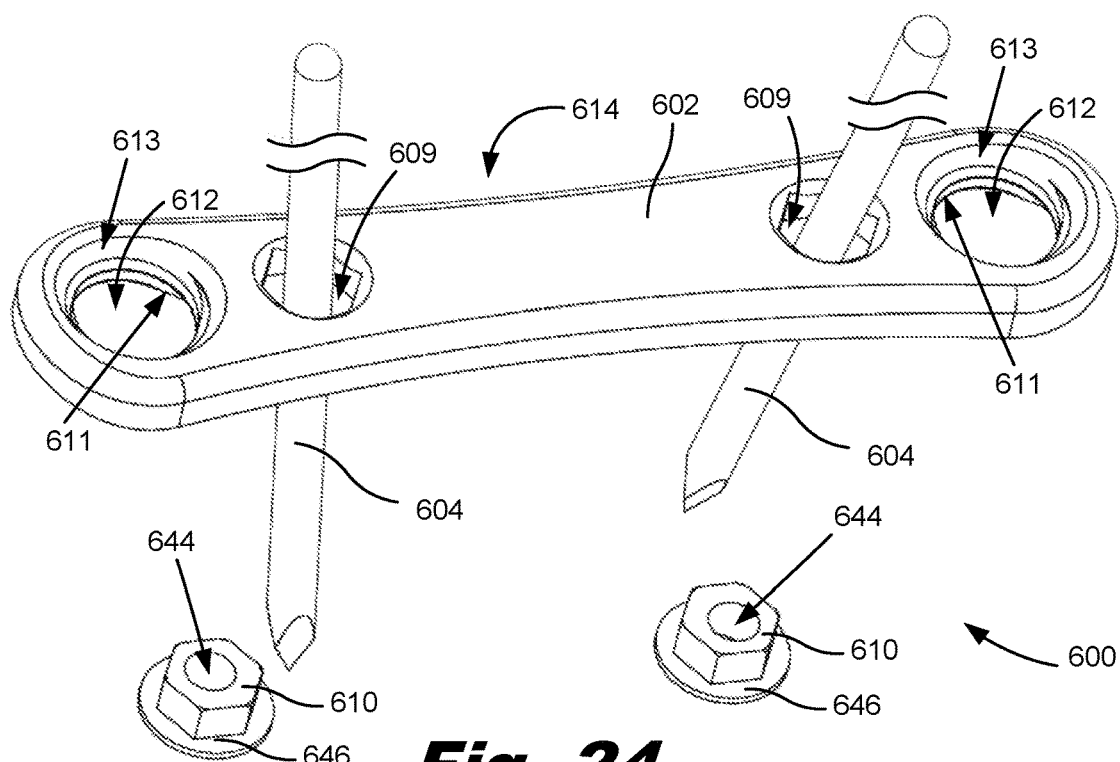
FIG. 24 is a top, oblique, exploded view of an assembly with a bone plate, draw plugs, and wires.
Figure 25:
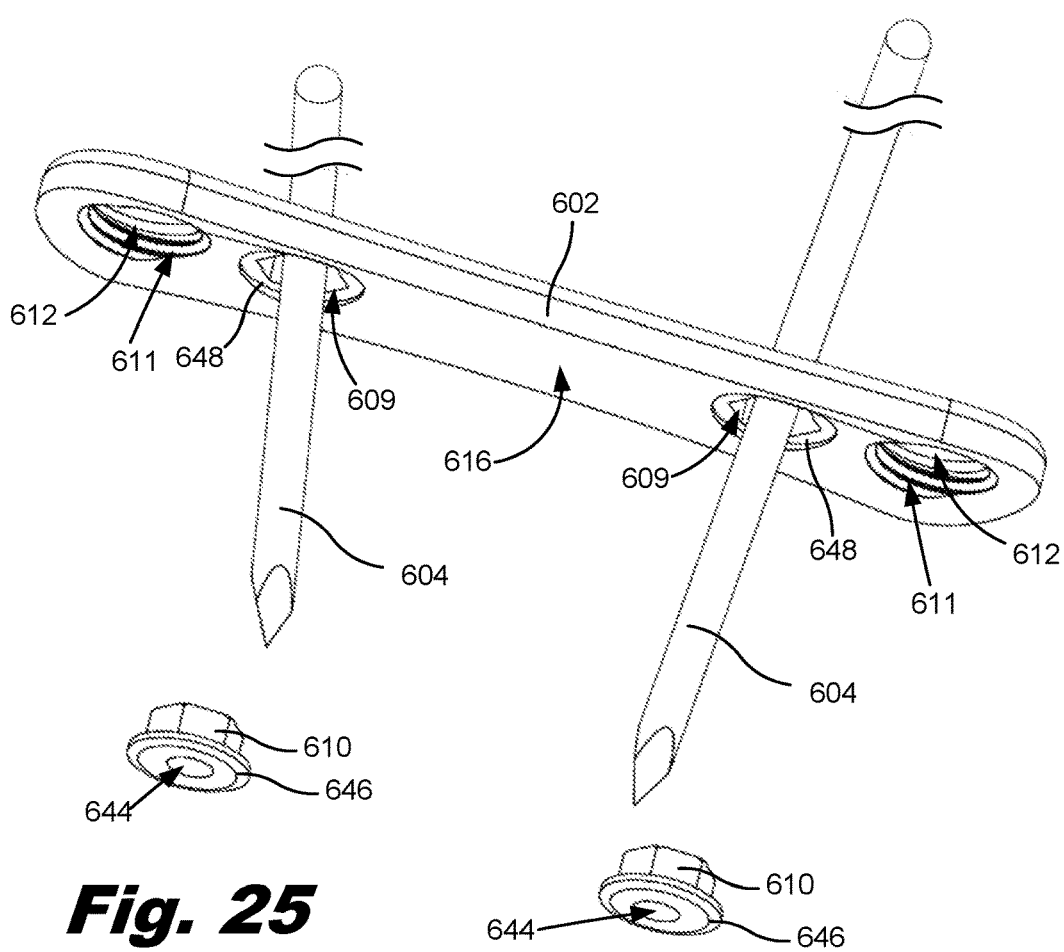
FIG. 25 is a bottom, oblique, exploded view of an assembly with a bone plate, draw plugs, and wires.

FIG. 21 is a longitudinal cross-section of an assembly 500 with a bone plate 502, wires 504, slide 538, and screws 506. In contrast to other embodiments described herein, the assembly 500 may include a wire 504 that is placed closer to an end of the bone plate 502 relative to the screw 506. However, the orientation of the wires 504 relative to the screw 506 may be opposite than that as shown in FIG. 21. The bone plate 502 has an obverse side 514 and a reverse side opposite the obverse side 514. When the bone plate 502 is implanted or otherwise attached to a tissue (e.g., bone), the obverse side 514 faces away from the tissue portions and the reverse side faces toward or abuts the tissue portions.

FIG. 21 is an embodiment of a bone plate 502 that accepts a slide 538 that secures the wires 504 after the bone plate 502 has been secured to the tissue. In an embodiment, technique, the bone plate 502 would be secured to the tissue and then the wire 504 may be placed using a drill guide and drill as described herein. This may ensure proper positioning of the wire 504 through a slide hole 540 formed through the slide 538 placed within the bone plate 502. In an embodiment, the bone plate 502 may, initially, be secured to the tissue using the screws 506 to provisionally place the bone plate 502 at the location along the tissue.

When the wire 504 is placed, the slide 538 may be assembled to the plate by passing the slide 538 over the wire 504 via the slide hole 540 and into the respective geometry within the bone plate 502. In some embodiments, the screw head 508 may be positioned such that when fully seated in the plate, it captures a portion of the slide 538, which prevents the slide 538 from being removed from the bone plate 502. The slide 538 may impart a similar biasing angle to the wire 504 resulting in the convergent-driven compression as described in other embodiments herein. In some embodiments, the exterior geometry of the slide 538 may match an interior surface of a slide hole formed in the bone plate 502 so that the slide 538 may not shift or rotate upon insertion of the slide 538 into the bone plate 502. The slide 538 may be inserted into the slide hole in a single orientation or multiple orientations.

In another embodiment, the method of installation may include implementing the template described herein to first insert the wire 504 into the tissue. When the wires 504 have been inserted into the tissue, the bone plate 502 may be slipped over the wire 504 with the wire 504 passing through the slide hole 540 of the slide 538. Once the bone plate 502 and slide 538 are in position, the screw 506 (e.g., bone screw, set screw threading into the bone plate 502, a locking screw, among other types of fasteners) may be inserted into the screw hole formed into the bone plate 502. In this embodiment, as the screw 506 is seated, the slide 538 may abut the wire 504 creating an interface 542 that causes the distal ends of the wire 504 to be drawn together creating the compression forces against the tissue as described herein.

In an embodiment, the method of installation may include initially placing the bone plate 502 on the tissue such as a bone. The screw 506 may be provisionally placed in preparation for the screw 506 to be finally seated into position. In this embodiment shown in FIG. 21, the final seating of the screw 506 is done after the wires 504 are placed thereby allowing for a full insertion and compression potential of the wires 504 to be realized prior to the bone plate 502 being completely set against the tissue using the screw 506.

This method may continue with placing the wires 504 at a strategic location and direction through the feature formed in the bone plate 502 used to receive the slide 538. In this embodiment, a drill guide or wire guide may be used to assist in the proper placement of the wires 504. The method may continue with placing the slide 538 over the wire 504 with the wire 504 being bent in order for the slide 538 to be properly placed within the feature formed in the bone plate 502. Again, the exterior surface of the slide 538 may match the interior surface of the feature formed in the bone plate 502 such that the features in not allowed to rotate about the wire 504 and specifically in a counter-clockwise rotational direction the slide 538 may encounter due to the type of wire 504 used. When the slide 538 is fully seated, the screw 506 may be fully seated or tightened in order to "lock-out" the slide 538.

Referring to FIGS. 22-27 an assembly 600 may include a stabilizing member, a dynamic element, and one or more fasteners. In the assembly 600, the stabilizing member may be a bone plate 602, the dynamic element may be a wire 604 or a set of wires 604, and the fasteners may be screws (not shown). In the embodiments presented herein, the screws may be similar to those presented and described in connection with FIGS. 1-5. In the embodiment of FIGS. 22-27, the screws of the assembly 600 may include locking screws, non-locking screws, fixed angle screws, or poly-axial screws. Although the embodiments described herein show specific features and elements, these specific features and elements are not meant to limit the aspects of those embodiments.

The bone plate 602 has an obverse side 614 and a reverse side 616. When the bone plate 602 is implanted or otherwise attached to a tissue (e.g., bone), the obverse side 614 faces away from the tissue portions and the reverse side 616 faces toward the tissue portions. The bone plate 602 may be made of a medical grade metal or plastic that allows for implantation into the human body. In an embodiment, the bone plate 602 may be made of a bendable material that is capable of deformation to fit across a portion of tissue within the human body. In a specific embodiment, the bone plate 602 may be deformed to conform against a broken bone such as a foot bone within the human body.

The bone plate 602 may include several screw holes 612 which extend through the obverse side 614 and reverse side 616. Two screw holes 612 are illustrated in FIGS. 22-27, although any number of screw holes 612 may be present in the bone plate 602. In some embodiments, the size of the bone plate 602 may be sized to fit across any portion of tissue including any bone or cartilage within the human body. In these embodiments, the size of the bone plate 602 to be used on a femur bone may be relatively larger than a bone plate 602 used to be used on a bone within the foot such as a cuneiform bone.

In an embodiment, each screw hole 612 formed through the bone plate 602 may include an internally threaded portion 611 and a nonthreaded portion 613 so that each screw hole 612 accepts either one of a locking screw or a non-locking screw. In an embodiment, an internal threaded portion 611 of the screw hole 612 may engage corresponding threads formed on the screw head in order to lock the screw to the bone plate 602. In this embodiment, the screw may be locked into the screw hole 612 when the screw is fully seated into the screw hole 612. In an embodiment, the screw is not a locking screw such that the bone plate 602 may be removed after, for example, the tissue has recuperated (e.g., bone has fused together).

Similar to the other embodiments described herein, a screw for purposes of this embodiment, may include a screw head with an exterior surface that fits within the screw hole 612 such that the screw head at least partially sunk into the bone plate 602. The exterior surface may be convex, spherical, or conical. In an embodiment, the placement of the screw head relative to the bone plate 602 may be such that the screw head does not protrude beyond a top plane on the obverse side 614 of the bone plate 602. This may prevent tissues within the body from rubbing against the screw head. In a specific embodiment, the screw may have a 3.5 mm diameter and lengths from 8 mm to 30 mm in 2 mm increments. In an embodiment, the threads of the screw formed below the screw head may have a pitch and thread height sufficient to hold the bone plate 602 to the tissue when the screw is fully sunk into the tissue. In an embodiment, the screw head may include any type of screw drive that allows a clinician to interface a screwdriver with the screw drive in order to drive the screw into the tissue.

The bone plate 602 of the assembly 600 may further include a number of draw plugs 610 formed into or placed within the body of the bone plate 602. In an embodiment, the draw plugs 610 may be coupled to the body of the bone plate 602. In the embodiments shown in FIGS. 22-27, the draw plugs 610 are placed into draw plug holes 609 which extend through the obverse side 614 to the reverse side 616. In an embodiment, the draw plug holes 609 formed through the bone plate 602 may have an interior surface that interfaces with an exterior surface of the draw plug 610 such that when the draw plug 610 is installed into the draw plug holes 609, the draw plug 610 is prevented from rotating within the draw plug holes 609. In the embodiments presented herein, the interior surfaces of any of the draw plug holes 609 may have any number of surfaces that create a fit (e.g., interference fit, clearance fit, transition fit among others) with the exterior surfaces of the draw plugs 610 to prevent the draw plug 610 from rotating within the draw plug holes 609.

In the specific embodiments shown in FIGS. 22-27, the draw plug 610 includes a plurality of surfaces forming the draw plug 610 into a hexagonal shape. Each surface (e.g., side) of the hexagonal shaped draw plug 610 may interface with an internal surface of the draw plug holes 609 creating a fit (e.g., interference fit, clearance fit, transition fit among others) between these surfaces. Unlike other embodiments described herein, however, the draw plug 610 may be rotated a certain degree and placed within the draw plug holes 609. Because each of the draw plug holes 609 also includes a draw plug 610 with a draw hole 644 formed therethrough, the radial orientation of the draw plug 610 within the draw hole 644 may be adjusted by radially adjusting the placement of the draw plug 610 within the draw plug hole 609. As described herein, the draw hole 644 formed through the draw plug 610 is not perpendicular to a top surface of the draw plug 610 such that a wire, when passed through the draw hole 644, is biased or bent when the bone plate 602 is coupled thereto. In an alternative embodiment, the draw hole 644 formed through the draw plug 610 is perpendicular to a top surface of the draw plug 610 with any pilot hole formed into the tissue being oblique to a central axis of the draw hole 644. In this embodiment, when the wire is passed through the draw hole 644, the wires may be bent when the bone plate 602 is forced against the tissue.

In the embodiments shown in FIGS. 22-27, because the draw hole 644 may be rotated due to the selective rotation of the draw plug 610 before interfacing within the draw plug hole 609, the direction of the bending or biasing of the wire forced through the draw hole 644 may also be selected. For example, the radial orientation of the draw hole 644 in the draw plug 610 may be set to bend the wire a direction away from a longitudinal axis of the bone plate 602. This is shown specifically in FIG. 26 which is a cross-section view of the assembly 600 showing the draw plugs 610 oriented so that the wires 604 extend obliquely across a longitudinal midplane of the bone plate 602, i.e., obliquely relative to the cross-section plane or the page. In other embodiments, the draw plug 610 may have more or less exterior surfaces than what is shown in FIGS. 22-27 so as to increase or decrease the incremental selective rotation of the draw plug 610 prior to insertion into the draw plug hole 609. This results in the selective biasing of the tissue when the wires 604 are inserted into the tissue when the bone plate 602 is placed over the wires 604.

In addition to the exterior surfaces of the draw plug 610 that match with the interior surfaces of the draw plug holes 609, the draw plug 610 may include a lip 646 that interfaces with a circular recess 648 formed on the bone plate 602 in some embodiments. The circular recess 648 may prevent the draw plug 610 from exiting the draw plug hole 609 and the bone plate 602 by interfacing the lip 646 with the circular recess 648 formed on the reverse side 616 of the bone plate 602. Consequently, when the assembly 600 is affixed to the tissue as described herein, the lip 646 may be sandwiched between the tissue and the reverse side 616 of the bone plate 602 and within the circular recess 648 so that the draw plug 610 cannot be removed from the assembly 600. In another example, the draw plugs 610 may be retained to the bone plate 602 by welding the draw plugs 610 to the bone plate or via another bonding method or via mechanical interconnection between the exterior of the draw plug 610 and the interior of the draw plug hole 609.

As described, the draw plugs 610 may include a draw hole 644 through which a wire 604 may be passed during assembly of the assembly 600 and coupling to the tissue as described herein. This draw hole 644 may be shown specifically in FIG. 26 which shows a longitudinal cross-section of an assembly 600 with the bone plate 602 and wires 604. The draw hole 644 formed through the draw plug 610 may be formed at an oblique angle. That is, the draw hole 644 formed through the draw plug 610 is not perpendicular to a top surface of the draw plug 610 such that the wire 604 is biased or bent when the bone plate 602 is coupled thereto as described. Although the embodiments descried herein show a specific oblique angle of the draw hole 644, this is meant merely as an example and the present specification contemplates that this angle may be relative more or less oblique in order to achieve the purposes of the bone plate 602 as described herein.

In another embodiment, the draw hole 644 may be formed in the draw plug 610 (or directly through the plate 602 in alternative embodiments) perpendicular to the top surface of the bone plate 602. In this embodiment, the initial placement of the wires 604 may be such that the distal ends of the wires 604 are diverging. This embodiment achieves a similar result of the other embodiments described herein by creating a moment on the wires 604 which would result in the compression of the tissue.

During installation of the assembly 600, the wire 604 may be previously inserted into a bone or other tissue of the body such that when the wire 604 is inserted through the draw hole 644, the wire 604 is biased or bent such that a force is applied to the tissue as described herein. In a specific example, the oblique angle of the draw hole 644 provides compression to be placed on neighboring pieces of tissue such that, during installation, the wires 604 cause the tissue pieces to be brought together. In these embodiments, the angles of the draw holes 644 in the draw plugs 610 may cause the individual wires 604 to be moved together (or apart) such that as the wires 604 are inserted into the tissue, the tissue is compressed together (or apart). In the embodiments described herein, the draw plug 610 may be made of polyether ether ketone (PEEK) so that as the wires 604 are passed through the draw holes 644 the friction between the draw plugs 610 and the wires 604 is reduced.

The assembly 600 may also include a number of wires 604 as described. The wires 604 may each be made of a highly elastic material or metal such as nitinol or surgical stainless steel. The wires 604 may include a sharpened distal tip used to pass the wires 604 a distance into a tissue such as bone. In an embodiment, the tissue may be pre-drilled prior to insertion of the wires 604 into the tissue to prevent the tissue from splitting as the wires 604 are passed into the tissue. In alternative embodiments, the tissue is not pre-drilled such that the wires 604 may be made relatively more permanent within the tissue such that the coefficient of friction produced between the tissue and the wires 604 is relatively higher.

As described herein, the wires 604 may be used to provide compression against the tissue as the wires 604 interface with the bone plate 602 in some embodiments. The wires 604 provide this compression by being biased towards each other as a result of being passed through the draw holes 644 formed through the draw plugs 610. Because of this difference between the angle of the draw holes 644 and the angle of the wires 604, the wires 604, when embedded into the tissue, may cause the tissue to be compressed as the bone plate 602 is coupled to the wires 604.

Figure 26:
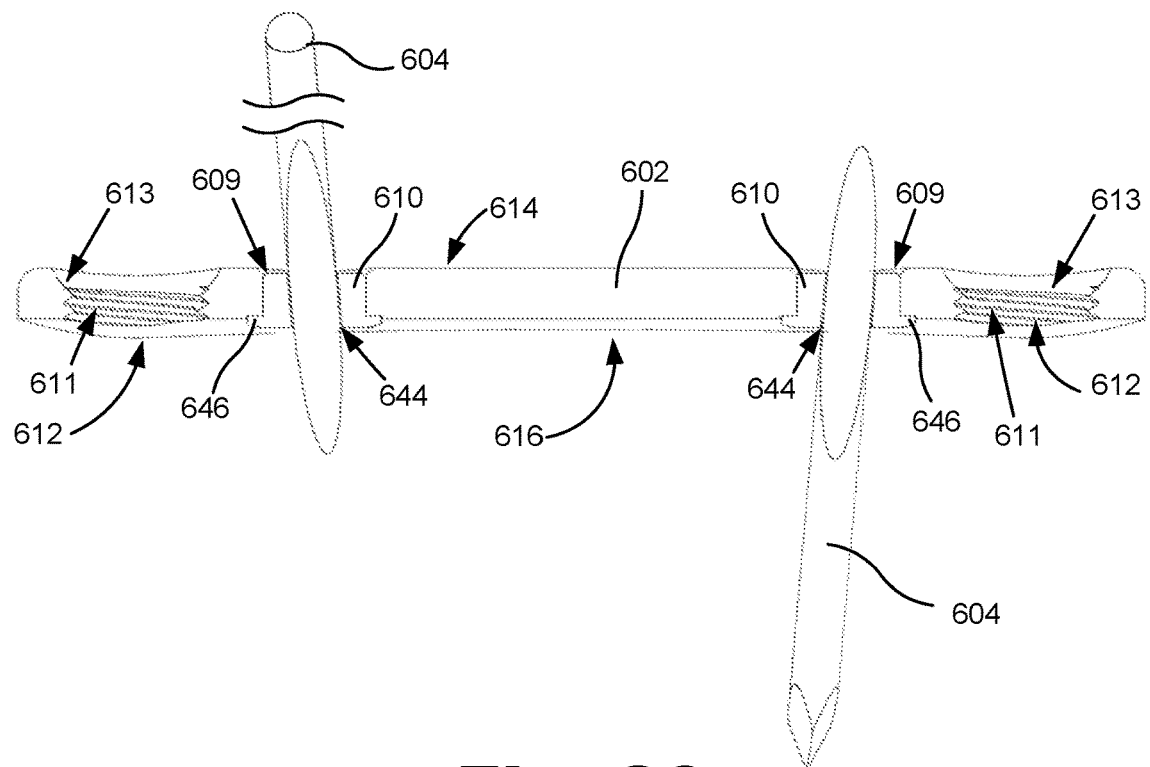
FIG. 26 is a longitudinal cross-section of an assembly with a bone plate, draw plugs, and wires.
Figure 27:
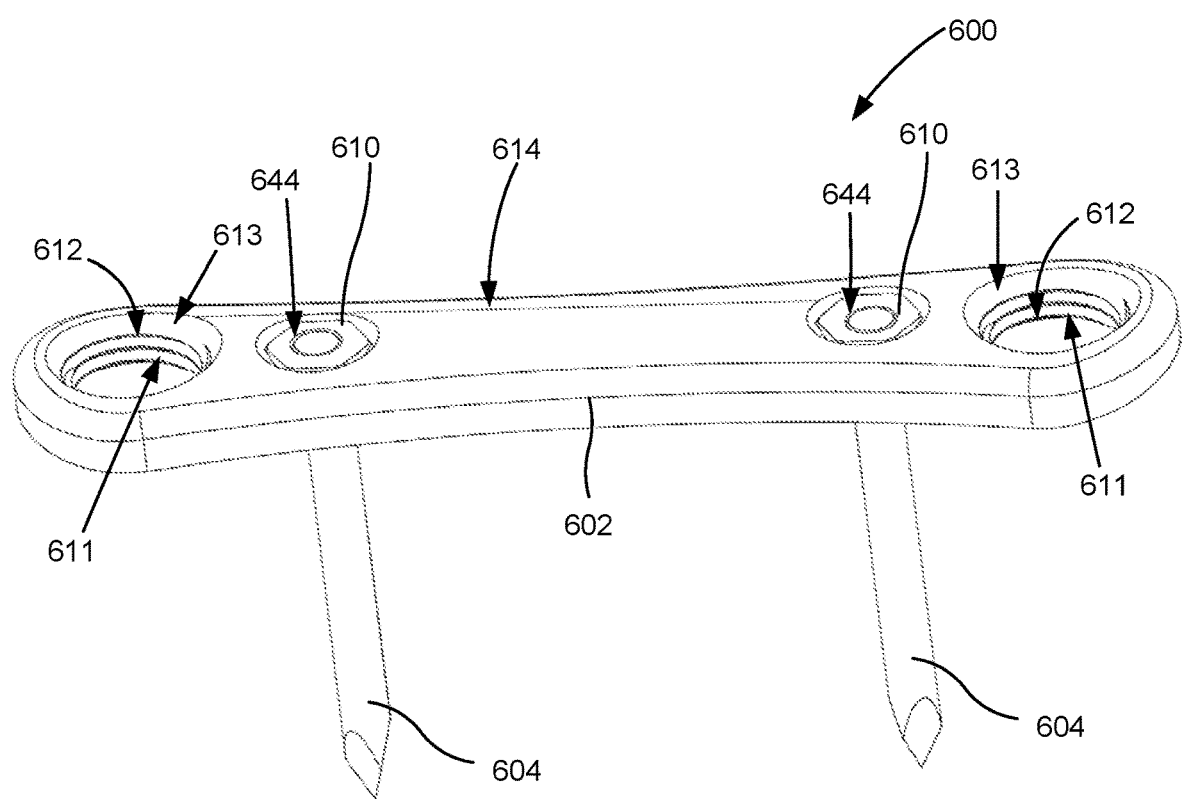
FIG. 27 is an oblique view of the placement of wires through a bone plate and draw plugs with the wires trimmed.

In other embodiments as shown in FIG. 26, the wires 604 may be used to align or otherwise reorient a first piece of tissue relative to a second piece of tissue. In this embodiment, the draw plugs 610 have been radially oriented within the draw plug holes 609 such that as the wires 604 are forced therethrough and bent, the wires 604 are bent to the left or right of the bone plate 602 based on the specific radial orientation of the draw hole 644 of the draw plug 610. This may cause one piece or multiple pieces of tissue to either diverge away from each other or align with each other in some way beneficial to the anatomy of the patient. Once the wires are in place and the bone plate 602 has been placed over the wires 604, the portions of the wires protruding beyond the surface of the obverse side 614 may be trimmed flush with the top of the draw plugs 610.

Although FIGS. 23-27 show a draw plug 610 having six sides (e.g., a hexagonal shape), the exterior surface may be varied to include three or more sides (a triangle, a square, a pentagon, a hexagon, etc.). Again, an increase in the number of sides may result in an increase in the number of radial orientations of the draw plug 610 within the draw plug holes 609. This results in as many radial orientations of wires passed through the draw hole 644 formed in the draw plug 610. With this increase in potential orientations of the wires, the ability to align, compress, dilate, or misalign two or more pieces of tissue.

Referring to FIGS. 28-30, in some embodiment assemblies 700, the bone plate 702 may have any number of draw holes 744 formed from the obverse side 714 to the reverse side 616. Again, an assembly 700 may include a stabilizing member, a dynamic element, and one or more fasteners. In the assembly 700, the stabilizing member may be a bone plate 702, the dynamic element may be a wire (not shown) or a set of wires, and the fasteners may be screws (not shown). In the embodiments presented herein, the screws may be similar to those presented and described in connection with FIGS. 1-5. In the embodiment of FIGS. 28-30, the screws of the assembly 700 may include locking screws non-locking screws, fixed angle screws, or poly-axial screws. Although the embodiments described herein show specific features and elements, these specific features and elements are not meant to limit the aspects of those embodiments.

The bone plate 702 has an obverse side 714 and a reverse side 716. When the bone plate 702 is implanted or otherwise attached to a tissue (e.g., bone), the obverse side 714 faces away from the tissue portions and the reverse side 716 faces toward the tissue portions. The bone plate 702 may be made of a medical grade metal or plastic that allows for implantation into the human body. In an embodiment, the bone plate 702 may be made of a bendable material that is capable of deformation to fit across a portion of tissue within the human body. In a specific embodiment, the bone plate 702 may be deformed to conform against a broken bone such as a foot bone within the human body.

The bone plate 702 may include several screw holes 712 which extend through the obverse side 714 and reverse side 716. Two screw holes 712 are illustrated in FIGS. 28-30, although any number of screw holes 712 may be present in the bone plate 702. In some embodiments, the size of the bone plate 702 may be sized to fit across any portion of tissue including any bone or cartilage within the human body. In these embodiments, the size of the bone plate 702 to be used on a femur bone may be relatively larger than a bone plate 702 used to be used on a bone within the foot such as a cuneiform bone.

In an embodiment, each screw hole 712 formed through the bone plate 702 may include an internally threaded portion 711 and a nonthreaded portion 713 so that each screw hole 712 accepts either one of a locking screw or a non-locking screw. In an embodiment, an internal threaded portion 711 of the screw hole 712 may engage corresponding threads formed on the screw head in order to lock the screw to the bone plate 702. In this embodiment, the screw may be locked into the screw hole 712 when the screw is fully seated into the screw hole 712. In an embodiment, the screw is not a locking screw such that the bone plate 702 may be removed after, for example, the tissue has recuperated (e.g., bone has fused together).

Similar to the other embodiments described herein, a screw for purposes of this embodiment, may include a screw head with an exterior surface that fits within the screw hole 712 such that the screw head at least partially sunk into the bone plate 702. The exterior surface may be convex, spherical, or conical. In an embodiment, the placement of the screw head relative to the bone plate 702 may be such that the screw head does not protrude beyond a top plane on the obverse side 714 of the bone plate 702. This may prevent tissues within the body from rubbing against the screw head. In a specific embodiment, the screw may have a 3.5 mm diameter and lengths from 8 mm to 30 mm in 2 mm increments. In an embodiment, the threads of the screw formed below the screw head may have a pitch and thread height sufficient to hold the bone plate 702 to the tissue when the screw is fully sunk into the tissue. In an embodiment, the screw head may include any type of screw drive that allows a clinician to interface a screwdriver with the screw drive in order to drive the screw into the tissue.

As shown in FIGS. 28-30 and specifically in FIG. 30, a number of draw holes 744 may be formed through the bone plate 702 that may have similar functions as those draw holes formed through the draw plugs in some of the other embodiments described herein. In the specific embodiments shown in FIGS. 28-30, the angle of the draw hole 744 may be set such that, as wires are passed through the draw hole 744, the wires are biased or bent so as to bring two individual pieces of tissue together. The elimination of the draw plugs in this embodiment reduces the number of components of the assembly 700. In these embodiments shown in FIGS. 28-30, the angle of the draw hole 744 may be formed such that it imparts the same or similar moment on the wire as the draw plug imparts and an elastic moment on the tissue in the alternative embodiments described herein.

Referring to FIGS. 31-34, the placement of the draw hole 844/draw plug 810 relative to the screw hole 812 in the assembly 800 may be reversed relative to the positions of those elements shown in other embodiments described herein. Again, an assembly 800 may include a stabilizing member, a dynamic element, and one or more fasteners. In the assembly 800, the stabilizing member may be a bone plate 802, the dynamic element may be a wire (not shown) or a set of wires, and the fasteners may be screws (not shown). In the embodiments presented herein, the screws may be similar to those presented and described in connection with FIGS. 1-5. In the embodiment of FIGS. 31-34, the screws of the assembly 800 may include locking screws non-locking screws, fixed angle screws, or poly-axial screws. Although the embodiments described herein show specific features and elements, these specific features and elements are not meant to limit the aspects of those embodiments.

The bone plate 802 has an obverse side 814 and a reverse side 816. When the bone plate 802 is implanted or otherwise attached to a tissue (e.g., bone), the obverse side 814 faces away from the tissue portions and the reverse side 816 faces toward the tissue portions. The bone plate 802 may be made of a medical grade metal or plastic that allows for implantation into the human body. In an embodiment, the bone plate 802 may be made of a bendable material that is capable of deformation to fit across a portion of tissue within the human body. In a specific embodiment, the bone plate 802 may be deformed to conform against a broken bone such as a foot bone within the human body.

The bone plate 802 may include several screw holes 812 which extend through the obverse side 814 and reverse side 816. Two screw holes 812 are illustrated in FIGS. 31-34, although any number of screw holes 812 may be present in the bone plate 802. In some embodiments, the size of the bone plate 802 may be sized to fit across any portion of tissue including any bone or cartilage within the human body. In these embodiments, the size of the bone plate 802 to be used on a femur bone may be relatively larger than a bone plate 802 used to be used on a bone within the foot such as a cuneiform bone.

In an embodiment, each screw hole 812 formed through the bone plate 802 may include an internally threaded portion 811 and a nonthreaded portion 813 so that each screw hole 812 accepts either one of a locking screw or a non-locking screw. In an embodiment, an internal threaded portion 811 of the screw hole 812 may engage corresponding threads formed on the screw head in order to lock the screw to the bone plate 802. In this embodiment, the screw may be locked into the screw hole 812 when the screw is fully seated into the screw hole 812.

Similar to the other embodiments described herein, a screw for purposes of this embodiment, may include a screw head with an exterior surface that fits within the screw hole 812 such that the screw head at least partially sunk into the bone plate 802. The exterior surface may be convex, spherical, or conical. In an embodiment, the placement of the screw head relative to the bone plate 802 may be such that the screw head does not protrude beyond a top plane on the obverse side 814 of the bone plate 802. This may prevent tissues within the body from rubbing against the screw head. In a specific embodiment, the screw may have a 3.5 mm diameter and lengths from 8 mm to 30 mm in 2 mm increments. In an embodiment, the threads of the screw formed below the screw head may have a pitch and thread height sufficient to hold the bone plate 802 to the tissue when the screw is fully sunk into the tissue. In an embodiment, the screw head may include any type of screw drive that allows a clinician to interface a screwdriver with the screw drive in order to drive the screw into the tissue.

In an embodiment, the draw plug holes formed through the bone plate 802 may have an interior surface that interfaces with an exterior surface of the draw plug 810 such that when the draw plug 810 is installed into the draw plug holes 809, the draw plug 810 is prevented from rotating within the draw plug holes 809. In the embodiments presented herein, the interior surfaces of any of the draw plug holes 809 may have any number of surfaces that create a fit (e.g., interference fit, clearance fit, transition fit among others) with the exterior surfaces of the draw plugs 810 to prevent the draw plug 810 from rotating within the draw plug holes 809 such as any non-circular cross-section shape. Hex, hexalobe, square, D-shaped, and other non-circular shapes are contemplated for the interior surfaces of the draw plug holes 809 and the exterior surfaces of the draw plugs 810. The non-circular shapes may permit a draw plug 810 to be inserted into a draw plug hole 809 in a single orientation (i.e., D-shape) or multiple orientations (i.e., hex or multi-lobe shapes) thereby changing the direction of resultant compression in the final construct. Additionally, the non-circular shapes of the draw plugs 810 interfacing with the non-circular cross-sectional internal surface prevent the draw plug 810 from rotating within the draw plug hole 809.

In addition to the exterior surfaces of the draw plug 810 that match with the interior surfaces of the draw plug holes 809, the draw plug 810 may include a lip 846 that interfaces with a circular recess formed on the bone plate 802 in an embodiment. The circular recess and lip 846 may prevent the draw plug 810 from exiting the draw plug hole 809 and the bone plate 802 by interfacing the lip 846 with the circular recess formed on the reverse side 816 of the bone plate 802. Consequently, when the assembly 800 is affixed to the tissue as described herein, the lip 846 may be sandwiched between the tissue and the reverse side 816 of the bone plate 802 and within the circular recess so that the draw plug 810 cannot be removed from the assembly 800. In another example, the draw plugs 810 may be retained to the bone plate 802 by welding the draw plugs 810 to the bone plate or via another bonding method or via mechanical interconnection between the exterior of the draw plug 810 and the interior of the draw plug hole 809.

Figure 34:
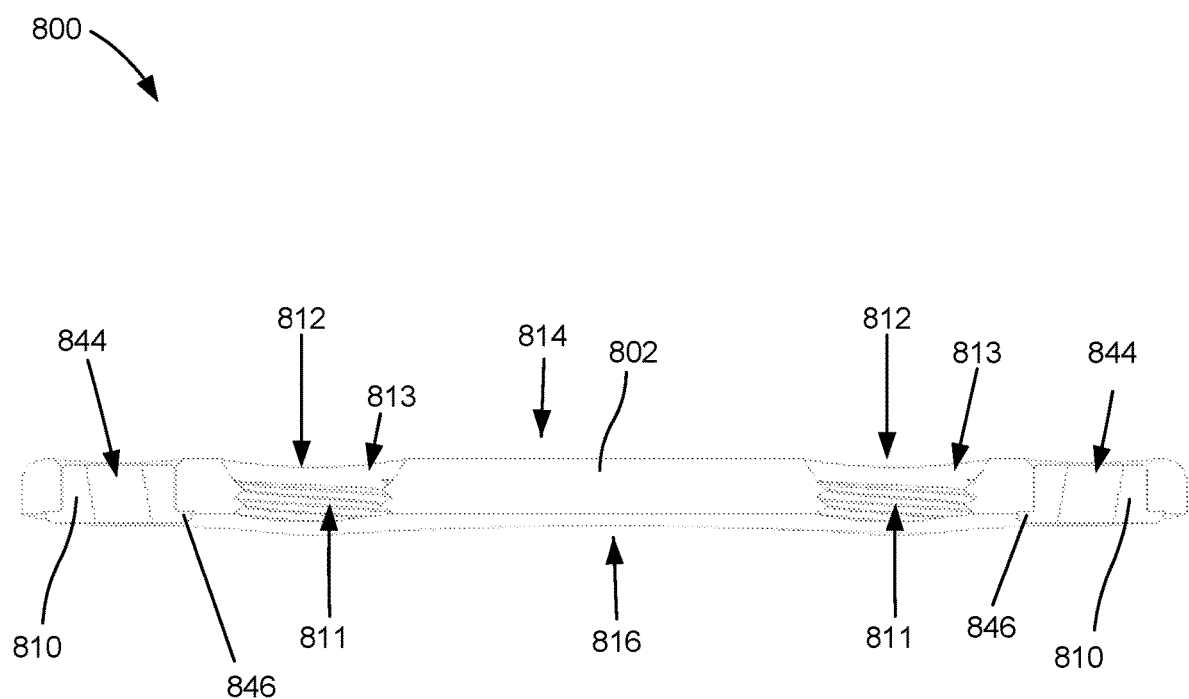
FIG. 34 is a longitudinal cross-section of an assembly with a bone plate and draw plugs.

As mentioned, the position of the screw holes 812 relative to the draw plug 810/draw plug holes 809/draw hole 844 may be switched. As shown in FIG. 34 (and FIGS. 31-33) the screw holes 812 may be placed relatively closer to the center of the bone plate 802 than the draw plug 810/draw plug holes 809/draw hole 844 assembly. The relative distances and placements of the screw holes 812 and the draw plug 810/draw plug holes 809/draw hole 844 assemblies may vary based on intended use of the assembly 800, anatomical placement of the bone plate 802 on a tissue, and the available surface area on the tissue on which the bone plate 802 is to be affixed, among other factors. Indeed, the present specification contemplates that the arrangements of the draw plug 810/draw plug holes 809/draw hole 844 assemblies, the size of the bone plates 802, and the arrangement of the screw holes 812, however the number, may vary depending on a plurality of factors each influenced by the anatomy onto which the assembly 800 is to be affixed. The present specification further contemplates that the shape and contours of the bone plate 802 in any embodiment described herein may be varied to, again, satisfy a plurality of factors each influenced by the anatomy onto which the assembly 800 is to be affixed.

Figure 35:
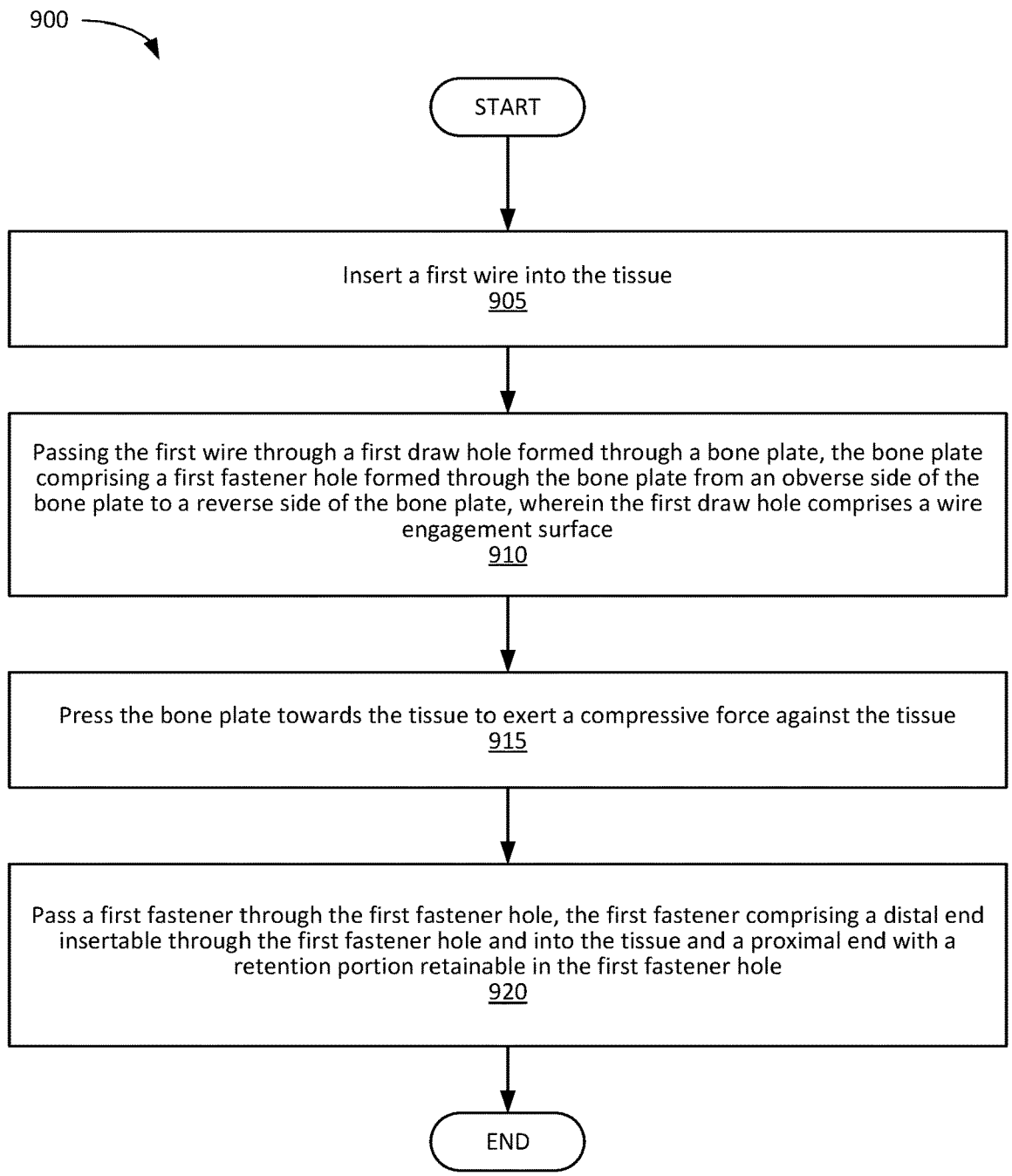
FIG. 35 is a flowchart illustrating a method of assembling a bone plate assembly to be coupled to a tissue according to an embodiment of the present disclosure.

FIG. 35 is a flowchart illustrating a method 900 of assembling a bone plate assembly to be coupled to a tissue according to an embodiment of the present disclosure. The methods described here may provide additional details to the assembly and use of the assembly as described in connection with FIGS. 1-5, FIGS. 6-11, FIGS. 12-20, FIG. 21, FIGS. 22-27, FIGS. 28-30, and FIGS. 31-34 may provide different embodiments based on the needs of a patient's care, for example. The present specification contemplates certain components of the methods and assemblies described herein may be incorporated into any individual method of assembly of a bone plate assembly without going beyond the principles described herein.

It is appreciated as well that the method of assembling a bone plate assembly to be coupled to a tissue may initially require the preparation of a patient into whose body this bone plate assembly is to be placed. The preparation of the patient may include certain other medical procedures may be completed such as local or general anesthesia, creating an incision in the patient's body to access a tissue where the bone plate assembly is to be coupled, and sanitization of the operating room, tools, and bone plate assembly, among other procedures.

The method 900 may include, in an embodiment, inserting a first wire into the tissue at block 905. In an embodiment, a template may be placed at a location along the tissue where a break, osteotomy, or other discontinuity has occurred. In an embodiment, a reference paddle of the template may be placed within the break to arrange the template at a location where the compression of the tissue would close the break. In an alternative embodiment, the template may not include a reference paddle allowing for relatively more freedom of placement of the template relative to a joint or break in the tissue. This template may be placed so that any number of wires may be arranged at and inserted into the tissue and ensure that the placement of the wires is set at a proper distance from the break or joint in order to avoid over compression or under compression during installation of the assembly as described herein. Any number of guide holes may be formed in this template that may be used to direct a drill or other device that may be used to form pilot holes at the location where the wire is to be inserted into the tissue.

The template may be placed so that any number of wires may be arranged at and inserted into the tissue. In some embodiments, the bone plate may be situated such that at least one wire is inserted into each side of the break. In some embodiments, the bone plate may be situated such that both of the wires are inserted into one side of the break or joint as long as the bone plate is held firmly (e.g., via one or more fasteners or screws or the wires alone) to the tissue to provide the required counter torque to result in fusion-site compression. The placement of the template may ensure that the placement of the wires is set at a proper distance from the break or joint in order to avoid over compression or under compression during installation of the assembly as described herein. In alternative embodiments, the assembly may implement a single wire or more than two wires depending on the feature size of the draw holes.

In order to properly align the wires at the locations along the surface of the tissue, the template may include any number of guide holes. In an embodiment, the guide holes may be used to direct a drill or other device that may prepare the location of the wires for insertion of those wires into the tissue. In an embodiment, the template (e.g., shown in FIG. 6) may include two guide holes. However, the present specification contemplates that any number of guide holes may be used to insert any number of wires into one or both of the pieces of tissue. Additionally, the guide holes may be non-parallel (e.g., divergent at distal ends of the guide holes) such that if a bone plate with perpendicular draw holes is placed over the wires, the moment created on the wires results in compression.

As described, in some embodiments, the guide holes may have been used by the clinician to drill pilot holes within the tissue to secure the wires therein. In this embodiment, these pilot holes may have an internal diameter smaller than the internal diameter of the guide holes and smaller in diameter of the wires. By making the pilot holes smaller than the diameter of the wires, placement of the wires through the guide holes and into the tissue may not split the tissue while also allowing a certain level of friction between the tissue and the wires. This may secure the wires into the tissue. As described herein, prior to insertion of the wires into the tissue, a leg may be placed within the pilot holes drilled into the tissue. This leg may mate with the wire and secure the wire into the tissue.

The wires may be relatively perpendicular to the tissue when inserted. However, similar tissue compression may be achieved by placing the wires at divergent angles relative to the tissue so that the distal tips are closer together than the proximal ends. Additionally, the wires may eventually be bent via one or more draw holes so that a compression force may be applied against the tissue so as to close the break or joint in the tissue.

In an embodiment, the template may be removed by sliding the template upwards and away from the tissue until the ends of the wires are clear from the guide holes formed through the template. As the template is removed, the reference paddle, where present, is also removed from in between the break in the tissue.

The method also includes, at block 910, passing the first wire through a first draw hole formed through a bone plate, the bone plate comprising a first fastener hole formed through the bone plate from an obverse side of the bone plate to a reverse side of the bone plate, wherein the first draw hole comprises a wire engagement surface. In an embodiment, the draw hole may be formed directly through the bone plate with the terminal and proximal ends of the wire passed through these draw holes during installation of the bone plate. In another embodiment, the installation of the bone plate relative to the wires includes passing a terminal and proximal ends of a plurality wires through a draw hole formed through a draw plug. In this embodiment, the draw plugs may be inserted into a draw plug hole formed through the bone plate from an obverse side to a reverse side of the bone plate.

In an embodiment, a draw hole may be formed through a draw plug. In this embodiment, the draw plug may be placed within a draw plug hole formed into the bone plate. In this specific embodiment, the draw plug includes a plurality of surfaces forming the draw plug into a non-circular shape. Each surface (e.g., side) of the non-circular shaped draw plug may interface with an internal surface of the draw plug holes creating a fit (e.g., interference fit, clearance fit, transition fit among others) between these surfaces. Unlike other embodiments described herein, however, the draw plug may be rotated a certain degree and placed within the draw plug holes. Because each of the draw plug holes also includes a draw hole, the radial orientation of the draw hole may be adjusted by adjusting the placement of the draw plug within the draw plug hole. At this point, the method 900 may end herein.

As described herein, in an embodiment the draw hole may be formed through a draw plug. These draw plugs may be inserted into a draw plug hole (e.g., similar to element 109 in FIG. 4) formed through the bone plate from an obverse side to a reverse side. As the wires are passed through their respective draw plugs in this embodiment, the wires may be distorted or bent due to the oblique draw holes formed through those draw plugs. Because the angle of the oblique draw holes in the draw plugs converge together at a reverse side of the bone plate, the proximal ends of the wires are drawn apart. Concurrently, the distal ends of the wires embedded into the tissue may be together causing the break in the tissue to converge and a level of compression between the pieces of the tissue to be realized. The level of compression placed between the pieces of the tissue may be dependent on a number of factors including the oblique angle of the draw hole or holes formed in the draw plug or draw plugs, the rigidity/elasticity of the wires, the distance of the draw plug holes from each other, the distance between the draw plug holes in the bone plate relative to the distance between the guide holes of the template, among other factors. Each of these features may be altered to achieve a specific compression at the break between the pieces of tissue and the elements of the bone plate assembly may be selected from a plurality of similar elements during the method 900. Where beneficial to the care of the patient, the compression direction produced by the herein-described assembly, may be out of plane of with the plate and may be either compressed towards/across a break or towards an adjacent tissue to correct a deformity, for example.

In an embodiment, the bone plate may not include fastener holes that receive a fastener used to secure the bone plate to the tissue. In this embodiment, the wires are used to secure the bone plate to the tissue alone. In the embodiments where the fastener holes are used, the bone plate may include one or more fastener holes to receive a fastener therein such as a locking screw, a non-locking screw, a fixed angle screw, a bone screw, a poly-axial screw, and a staple, among others. In the embodiments where the fasteners include a type of screw, the fastener holes may include an internally threaded portion and a nonthreaded portion so that each fastener hole accepts either one of a locking screw or a non-locking screw (among other types of screws including bone screws). In an embodiment, an internal threaded portion of the fastener hole may engage corresponding threads formed on the screw head in order to lock the screw to the bone plate. In this embodiment, the screw may be locked into the fastener hole when the screw is fully seated into the screw hole. In an embodiment, the fastener is not a locking screw (such as a bone screw) such that the fastener hole of the bone plate does not include a threaded portion or the threaded portions are not used to seat the non-locking screw into the bone plate.

In an embodiment, the draw holes may include a wire engagement surface used to receive a wire therein. The wire engagement surface of the one or more draw holes may be oriented obliquely such that motion of the wires through their respective draw holes exerts a compressive force against the tissue.

The method 900 may continue with pressing the bone plate towards the tissue within the patient's body at block 915. Again, the tissue may include a break over which the bone plate is to be used to draw together a first portion of the tissue and a second portion of the tissue. In these embodiments, at least one of a fastener or a wire may be secured into the first portion of the tissue while at least one of a fastener or a wire may be secured into the second portion of the tissue in order to help mend the break in the tissue and hold the bone plate to that tissue during recuperation of the that tissue.

Specific examples described herein describe that a fastener and a wire are to be inserted into the first portion of tissue and a fastener and a wire are to be inserted into the second portion of tissue. These are meant as examples only and the present specification contemplates that more than one fastener and a wire may be inserted into either of the first portion of tissue or second portion of tissue. Additional fasteners and wires may provide additional force used to secure the bone plate to the tissue so that the tissue may recuperate. As a result, the present specification contemplates any number of fastener holes and draw holes. As described herein, the bone plate may be secured to the bone plate using only the wires and, in this embodiment, the method may not include the insertion of fasteners through the bone plate.

By pressing the bone plate towards the tissue in block 915, the angle of the draw hole may be set such that, as the draw hole is passed over the wires toward the tissue, the wire is biased or bent so as to bring two individual pieces of tissue together. The angle of the draw hole may be formed such that it imparts the same or similar moment on the wire as the draw hole imparts and an elastic moment on the tissue in the alternative embodiments described herein. As the bone plate is moved closer to the tissue, the force required to place the reverse side of the bone plate against the tissue may increase as the wire may be bent in the oblique draw holes. Concurrently, compression of the pieces of the tissue may also increase. As the reverse side of the bone plate makes contact with the surface of the tissue a final position of the wires within the bone plate and tissue is realized. Additionally, as the reverse side of the bone plate contacts the tissue, a maximum compression of the pieces of tissue against each other is realized. This compression between pieces of tissue causes the break in the tissue to disappear and the bone plate and wires are now maintaining the position of the pieces of tissue.

The method 900 may further include, at block 920, passing a first fastener through the first fastener hole. In the embodiments where the bone plate includes a fastener hole to receive the first fastener, the first fastener may include a distal end insertable through the first fastener hole and into the tissue and a proximal end retainable in the first fastener hole. As described herein, the fastener may be a staple, screw, locking screw or the like that is used to secure the bone plate to the surface of the tissue. In a specific embodiment, the fastener is a locking screw. As described herein, the locking screw may include a first set of threads located at a proximal end of the locking screw below the screw heads. This first set of threads may interface with threads formed on the inside surface of the fastener holes. A second set of threads formed along a shaft of the locking screw may interface with the tissue in order to seat the locking screw into the tissue and create friction between the fastener screw and the tissue.

Again, although the method 900 describes a first fastener engaging with a first fastener hole, the present specification contemplates that the number of fasteners and fastener holes may be more than one in order to secure the bone plate to the tissue at different locations along the surface of the tissue or along the surface of a second portion of the tissue. In another embodiment, the bone plate may not include any fastener holes and instead the bone plate may be secured to the tissue via the wires alone.

In an embodiment and as the clinician may access the surface of the tissue via the screw holes when the bone plate is against the tissue. At this point, any type of fastener such as a screw, staple, or locking screw may be selected based on a number of factors. These factors may include the type of tissue into which the screws are passed, whether the screws are to be locking screws or not, the diameter of the screw holes, the screw drive to be used, among other factors.

Similar to the pilot holes drilled for the wires, pilot holes may be formed at the screw holes to be used to allow the fasteners, staples, or screws to pass through the screw holes and into the tissue. The pilot holes may be drilled by a clinician so as to prevent any splitting of the tissue as the screws are driven into the tissue. In a specific embodiment, the internal diameter of the pilot holes may be smaller than the shaft diameter of the screws so that a level of friction may be realized between the internal surface of the pilot holes and the outer surfaces of the screws used to secure the bone plate to the tissue.

At this point, the screws may be seated into the pilot holes with the screw heads being sunk into the bone plate as described herein. The wires may then be trimmed to be flush with a top surface of the draw plugs or the bone plate so that the wires do not protrude from the obverse side of the bone plate. The clinician may close up the incision and perform any post-operation processes necessary to secure the health of the patient ending the method of FIG. 35. The method 900 described in connection with the figures herein may include any combination of the processes described herein in any order to achieve that assembly of the bone plate assembly.

Any methods disclosed herein includes one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles of the technology.

While specific embodiments and applications of the present technology have been illustrated and described, it is to be understood that the technology is not limited to the precise configuration and components disclosed herein. Various modifications, changes, and variations which will be apparent to those skilled in the art may be made in the arrangement, operation, and details of the methods and systems of the present technology disclosed herein without departing from the spirit and scope of the technology.

The invention claimed is:

1. A bone plate assembly couplable to a tissue, the bone plate assembly comprising:
 a bone plate elongate along a longitudinal bone plate axis, the bone plate comprising:
  an obverse side;

a reverse side;

a fastener hole that extends through the bone plate from the obverse side to the reverse side;

a first draw hole formed at an oblique angle through the bone plate from the obverse side to the reverse side, the first draw hole comprising a pin engagement surface, wherein the first draw hole is adjacent to the fastener hole along the longitudinal bone plate axis;

a fastener comprising:
 a distal fastener end portion insertable through the fastener hole and into the tissue; and
 a proximal fastener end portion retainable in the fastener hole; and a first pin insertable into the first draw hole, the first pin extending between a proximal pin end portion and a distal pin end portion, the distal pin end portion extending along a distal pin end portion axis and anchorable in the tissue, and the proximal pin end portion having a retention portion that is retainable in the first draw hole, wherein the pin engagement surface is oriented obliquely from the obverse side to the reverse side of the bone plate, so that the retention portion extends obliquely with respect to the distal pin end portion axis when the retention portion is retained in the first draw hole, such that motion of the first pin through the first draw hole causes the distal pin end portion to exert a compressive force against the tissue.

2. The bone plate assembly of claim 1, wherein:
the fastener hole comprises a threaded portion; and
the fastener is a locking screw comprising an engagement thread at the proximal fastener end portion, wherein the engagement thread is engageable with the threaded portion.

3. The bone plate assembly of claim 1, further comprising a leg comprising:
 a distal leg end insertable into the tissue; and
 a proximal leg end comprising a channel formed from the proximal leg end toward the distal leg end;
 wherein the channel is sized to receive the distal pin end portion of the first pin.

4. The bone plate assembly of claim 3, wherein the leg further comprises:
 an insertion tip formed into a tapered shape to initiate insertion into the tissue; and
 retention features protruding outward from a longitudinal axis of the leg and shaped to increase friction between the leg and the tissue when inserted into the tissue.

5. The bone plate assembly of claim 1, wherein the first pin comprises:
 a sharpened tip at a distal end of the distal pin end portion, wherein the sharpened tip is used to pass the first pin a distance into the tissue.

6. The bone plate assembly of claim 1, wherein the bone plate further comprises:
 a second draw hole comprising a second pin engagement surface;
 wherein insertion of the first pin into the first draw hole and insertion of a second pin into a second draw hole causes the first and second pins to apply a compression force against two pieces of the tissue to urge and compress the two pieces of the tissue together.

7. The bone plate assembly of claim 1, further comprising:
a first draw plug;
wherein a first draw plug hole is formed through the bone plate from the obverse side to the reverse side to receive a first draw plug, the first draw plug comprising:
 the first draw hole formed therethrough; and
 a lip that interfaces with a recess formed on the bone plate to prevent the first draw plug from exiting the first draw plug hole when the bone plate is installed.

8. The bone plate assembly of claim 7, wherein the first draw plug further comprises:
non-circular cross-section shape that interfaces with an internal surface portion formed within the first draw plug hole to prevent the first draw plug from rotating within the first draw plug hole.

9. A bone plate assembly to be coupled to a tissue, the bone plate assembly comprising:
a bone plate elongate along a longitudinal bone plate axis, the bone plate comprising:
 an obverse side;
 a reverse side;
 a first fastener hole that extends through the bone plate from the obverse side to the reverse side;
 a second fastener hole that extends through the bone plate from the obverse side to the reverse side;
 a first draw hole formed at first oblique angle through the bone plate from the obverse side to the reverse side, the first draw hole comprising a first pin engagement surface, wherein the first draw hole is adjacent to the first fastener hole along the longitudinal bone plate axis;
 a second draw hole formed at a second oblique angle through the bone plate from the obverse side to the reverse side, the second draw hole comprising a second pin engagement surface, wherein the second draw hole is adjacent to each of the first draw hole and the second fastener hole along the longitudinal bone plate axis; and
a first fastener comprising:
 a distal first fastener end portion insertable through the first fastener hole and into the tissue; and
 a proximal first fastener end portion retainable in the first fastener hole;
a second fastener comprising:
 a distal second fastener end portion insertable through the second fastener hole and into the tissue; and
 a proximal second fastener end portion retainable in the second fastener hole;
a first pin insertable into the first draw hole, the first pin extending between a proximal first pin end portion and a distal first pin end portion, the distal first pin end portion extending along a distal first pin end portion axis and anchorable in the tissue, and the proximal first pin end portion having a first retention portion that is retainable in the first draw hole;
 a second pin insertable into the second draw hole, the second pin extending between a proximal second pin end portion and a distal second pin end portion, the distal second pin end portion extending along a distal second pin end portion axis and anchorable in the tissue, and the proximal second pin end portion having a second retention portion that is retainable in the second draw hole,
wherein first and second retention portions extend away from each other when they are retained by the first and second draw holes, respectively, such that 1) the first and second pin engagement surfaces cause the first and second retention portions to extend obliquely with respect to the distal first pin end portion and the distal second pin end portion, respectively, 2) the first pin flexes at a location between the proximal first pin end portion and the distal first pin end portion, 3) the second pin flexes at a location between the proximal second pin end portion and the distal second pin end portion, and 4) the distal first pin end portion and the distal second pin end portion exert a compressive force against the tissue.

10. The bone plate assembly of claim 9, wherein the first fastener hole comprises a first threaded portion and the second fastener hole comprises a second threaded portion; and the first fastener and the second fastener are locking screws, the first fastener comprising:

a first engagement thread at the proximal first fastener end portion; and a second engagement thread at the proximal second fastener end portion;

wherein the first engagement thread and second engagement thread engage with the first threaded portion of the first fastener hole and second threaded portion of the second fastener hole, respectively.

11. The bone plate assembly of claim 9, further comprising a leg comprising:

a distal leg end insertable into the tissue; and a proximal leg end comprising a channel formed from the proximal leg end toward the distal leg end;

wherein the channel is sized to receive one of the distal first pin end portion and the distal second pin end portion.

12. The bone plate assembly of claim 11, wherein the leg further comprises:

an insertion tip formed into a tapered shape to initiate insertion into the tissue; and retention features protruding outward from a longitudinal axis of the leg and shaped to increase friction between the leg and the tissue when inserted into the tissue.

13. The bone plate assembly of claim 9, wherein the distal second pin end portion comprise a sharpened distal tip used to pass the second wire a distance into a tissue.

14. The bone plate assembly of claim 9, further comprising:

a first draw plug;

a second draw plug;

wherein a first draw plug hole is formed through the bone plate from the obverse side to the reverse side to receive a first draw plug, the first draw plug comprising:

the first draw hole formed therethrough; and a lip that interfaces with a recess formed on the bone plate to prevent the first draw plug from exiting the first draw plug hole when the bone plate is installed; and wherein a second draw plug hole is formed through the bone plate from the obverse side to the reverse side to receive a second draw plug, the second draw plug comprising:

the second draw hole formed therethrough; and a lip that interfaces with a recess formed on the bone plate to prevent the second draw plug from exiting the second draw plug hole when the bone plate is installed.

15. The bone plate assembly of claim 14, wherein the first draw plug and a second draw plug further comprise:

a non-circular cross-sectional shape that interfaces with a non-circular cross-sectional shaped internal surface portion formed within the first draw plug hole and second draw plug hole to prevent the first draw plug and second draw plug, respectively, from rotating within the first draw plug hole and second draw plug hole.

16. A method of assembling a bone plate assembly to be coupled to a tissue, the method comprising the steps of:

inserting a first pin into the tissue so as to define a tissue hole in the tissue, the first pin having a distal pin portion and a proximal pin portion, wherein the proximal pin portion has a retention portion;

passing the first pin through a first draw hole that extends obliquely through a bone plate, the bone plate comprising a first fastener hole formed through the bone plate from an obverse side of the bone plate to a reverse side of the bone plate, wherein the first fastener hole is adjacent the first draw hole along a longitudinal axis of the bone plate, and the first draw hole comprises a wire engagement surface that is oblique to the tissue hole;

pressing the bone plate towards the tissue until the retention portion is retained in the first draw hole, which causes the wire engagement surface to exert a force onto the retention portion which causes the retention portion to extend obliquely relative to the distal pin portion, thereby causing the distal pin portion to exert a compressive force against the tissue;

passing a first fastener through the first fastener hole, the first fastener comprising:

a distal fastener end portion insertable through the first fastener hole and into the tissue; and a proximal fastener end portion with a retention portion retainable in the first fastener hole.

17. The method of claim 16, further comprising: trimming a portion of the first pin that extends above an obverse side of the bone plate.

18. The method of claim 16, further comprising:

placing a template over a discontinuity in the tissue, the template comprising a guide hole;

drilling a pilot hole at a location of the guide hole into the tissue; and using the pilot hole to pass the first pin into the tissue.

19. The method of claim 18, further comprising:

placing a leg into the pilot hole prior to passing the first pin into the tissue, the leg comprising:

a distal leg end insertable into the tissue; and a proximal leg end comprising a channel formed from the proximal leg end toward the distal leg end.

20. The method of claim 16, further comprising:

pressing the bone plate against the tissue to distort the first pin passing through the first draw hole as a result of the first draw hole being oblique to the tissue hole.

* * * * *